United States Patent
Wu

(10) Patent No.: US 10,696,642 B2
(45) Date of Patent: Jun. 30, 2020

(54) TEAD TRANSCRIPTION FACTOR AUTOPALMITOYLATION INHIBITORS

(71) Applicant: The General Hospital Corporation, Boston, MA (US)

(72) Inventor: Xu Wu, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/762,993

(22) PCT Filed: Sep. 23, 2016

(86) PCT No.: PCT/US2016/053318
§ 371 (c)(1),
(2) Date: Mar. 23, 2018

(87) PCT Pub. No.: WO2017/053706
PCT Pub. Date: Mar. 30, 2017

(65) Prior Publication Data
US 2018/0215721 A1  Aug. 2, 2018

Related U.S. Application Data

(60) Provisional application No. 62/306,421, filed on Mar. 10, 2016, provisional application No. 62/222,238, filed on Sep. 23, 2015.

(51) Int. Cl.
| | | |
|---|---|---|
| *C07D 249/12* | (2006.01) | |
| *C07D 249/14* | (2006.01) | |
| *C07D 285/125* | (2006.01) | |
| *C07D 277/74* | (2006.01) | |
| *C07D 271/113* | (2006.01) | |
| *C07D 213/82* | (2006.01) | |
| *C07D 401/12* | (2006.01) | |
| *C07D 401/14* | (2006.01) | |
| *A61P 35/00* | (2006.01) | |
| *G01N 33/68* | (2006.01) | |
| *G01N 33/50* | (2006.01) | |
| *C12Q 1/25* | (2006.01) | |

(52) U.S. Cl.
CPC ............ *C07D 249/12* (2013.01); *A61P 35/00* (2018.01); *C07D 213/82* (2013.01); *C07D 249/14* (2013.01); *C07D 271/113* (2013.01); *C07D 277/74* (2013.01); *C07D 285/125* (2013.01); *C07D 401/12* (2013.01); *C07D 401/14* (2013.01); *C12Q 1/25* (2013.01); *G01N 33/5091* (2013.01); *G01N 33/68* (2013.01)

(58) Field of Classification Search
CPC .. C07D 249/12; C07D 213/82; C07D 249/14; C07D 271/113; C07D 277/74; C07D 285/125; C07D 401/12; C07D 401/14; A61P 35/00; C12Q 1/25; G01N 33/5091; G01N 33/68

USPC ...................................................... 514/236.2
See application file for complete search history.

(56) References Cited

U.S. PATENT DOCUMENTS

| | | | | |
|---|---|---|---|---|
| 5,939,462 A | * | 8/1999 | Connell ................. | A61K 31/00 514/660 |
| 6,346,532 B1 | | 2/2002 | Maruyama et al. | |
| 7,723,369 B2 | | 5/2010 | Mjalli et al. | |
| 7,897,605 B2 | | 3/2011 | Wang et al. | |

OTHER PUBLICATIONS

Manikrao et al. Der Pharma Chemica, 2(5), p. 76-83 (Year: 2010).*
PUBCHEM: Substance Record for SID 47645506. Feb. 20, 2008. [retrieved on Oct. 24, 2016]. Retrieved from the Internet. <URL: https://pubchem.ncbi.nlm.nih.gov/substance/47645506>.
International Search Report and Written Opinion dated Feb. 16, 2017 in international application No. PCT/US2016/053318, 10 pgs.
Benhaddou et al., "Transcription factor TEA.D4 regulates expression of myogenin and the unfolded protein response genes during C2C12 cell differentiation," Cell Death Differ, 2012, 19: 220-231.
Chan et al., "A role for TAZ in migration, invasion, and tumorigenesis of breast cancer cells," Cancer Res, 2008, 68: 2592-2598.
Chan et al., "Autopalmitoylation of TEAD Proteins Regulates Transcriptional Output of Hippo Pathway," Nat Chem Biol, Apr. 2016, 12: 282-289.
Chan et al., "Supplemental Information: Autopalmitoylation of TEAD Proteins Regulates Transcriptional Output of Hippo Pathway," Nat Chem Biol, Apr. 2016, 12: 282-289.
Chandra et al., "The GDI-like solubilizing factor PDEdelta sustains the spatial organization and signalling of Ras family proteins," Nat Cell Biol, 2012, 14: 148-158.
Chen et al., "Structural basis of YAP recognition by TEAD4 in the hippo pathway," Genes Dev, 2010, 24: 290-300.
Duncan and Gilman, "Autoacylation of G protein alpha subunits," J Biol Chem, 1996, 271: 23594-23600.
Dupont et al., "Role of YAP/TAZ in mechanotransduction," Nature, 2011, 474: 179-183.
Faergeman and Knudsen, "Role of long-chain fatty acyl-CoA esters in the regulation of metabolism and in cell signaling," Biochem J, 1997, 323 (Pt1}: 1-12.
Fitamant et al., "YAP Inhibition Restores Hepatocyte Differentiation in Advanced HCC, Leading to Tumor Regression," Cell Reports, 2016.
Fukata and Fukata, "Protein palmitoylation in neuronal development and synaptic Plasticity," Nat Rev Neurosci, 2010, 11: 161-175.
Greaves and Chamberlain, "DHHC palmitoyl transferases: substrate interactions and (patho)physiology," Trends Biochem Sci, 2011, 36: 245-253.

(Continued)

*Primary Examiner* — Kristin A Vajda
(74) *Attorney, Agent, or Firm* — Fish & Richardson P.C.

(57) ABSTRACT

The present disclosure compounds, as well as their compositions and methods of use. The compounds inhibit the activity of the TEAD transcription factor, and are useful in the treatment of diseases related to the activity of TEAD transcription factor including, e.g., cancer and other diseases.

18 Claims, 40 Drawing Sheets

(56) References Cited

OTHER PUBLICATIONS

Hang and Linder, "Exploring protein lipidation with chemical biology," Chem Rev, 2011, 111: 6341-6358.
Hannoush, "Profiling cellular myristoylation and palmitoylation using omega-alkynyl fatty acids," Methods Mol Biol, 2012, 800: 85-94.
Hantschel et al., "A myristoy l/phosphotyrosine switch regulates c-Ab1," Cell, 2003, 112: 845-857.
Harvey et al., "The Hippo pathway and human cancer," Nature Reviews Cancer, 2013, 13: 246-257.
International Preliminary Report on Patentability in International Application No. PCT/US2016/053318, dated Apr. 5, 2018, 7 pages.
Ismail et al., "Arl2-GTP and Arl3-GTP regulate a GDI-like transport system for farnesylated cargo," Nat Chem Biol, 2011, 7: 942-949.
Jennings and Linder, "DHHC protein S-acyltransferases use similar ping-pong kinetic mechanisms but display different acyl-CoA specificities," J Biol Chem, 2012, 287: 7236-7245.
Jiao et al., "A peptide mimicking VGLL4 function acts as a YAP antagonist therapy against gastric cancer," Cancer Cell, 2014, 25: 166-180.
Johnson and Halder, "The two faces of Hippo: targeting the Hippo pathway for regenerative medicine and cancer treatment," Nature Reviews. Drug Discovery, 2014, 13: 63-79.
Kim et al., "cAMP/PKA signalling reinforces the LATS-YAP pathway to fully suppress YAP in response to actin cytoskeletal changes," Embo J, 2013, 32: 1543-1555.
Koontz et al., "The Hippo effector Yorkie controls normal tissue growth by antagonizing scalloped-mediated default repression," Dev Cell, 2013, 25: 388-401.
Kummel et al., "Unique self-palmitoylation activity of the transport protein particle component Bet3: a mechanism required for protein stability," PNAS, 2006, 103: 12701-12706.
Li et al., "Structural insights into the YAP and TEAD complex," Genes & Development, 2010, 24: 235-240.
Liu-Chittenden et al., "Genetic and pharmacological disruption of the TEAD-YAP complex suppresses the oncogenic activity of YAP," Genes & Development, 2012, 26: 1300-1305.
Martin and Cravatt, "Large-scale profiling of protein palmitoylation in mammalian cells," Nat Methods, 2009, 6, 135-138.
Menendez and Lupu, "Fatty acid synthase and the lipogenic phenotype in cancer pathogenesis," Nat Rev Cancer, 2007, 7: 763-777.
Mohseni et al.. "A genetic screen identifies an LKB1-MARK signaling axis controlling the Hippo-YAP pathway," Nat Cell Biol, 2014, 16: 108-117.
Nagar et al., "Structural basis for the autoinhibition of c-Abl tyrosine kinase," Cell, 2003, 112: 859-871.
Nguyen et al., "LKB1 tumor suppressor regulates AMP kinase/mTOR-independent cell growth and proliferation via the phosphorylation of Yap," Oncogene, 2013, 32: 4100-4109.
Noland et al., "Palmitoylation of TEAD Transcription Factors Is Required for Their Stability and Function in Hippo Pathway Signaling," Structure, 2016, 24: 1-8.
Ota and Sasaki "Mammalian Tead proteins regulate cell proliferation and contact inhibition as transcriptional mediators of Hippo signaling," Development, 2008, 135: 4059-4069.
Pan, "Hippo signaling in organ size control," Genes Dev, 2007, 21: 886-897.
Pan, "The hippo signaling pathway in development and cancer," Dev Cell, 2010, 19: 491-505.
Park et al., "Novel TAZ modulators enhance myogenic differentiation and muscle regeneration," Br J Pharmacol, 2014, 171: 4051-4061.
Pobbati et al., "Targeting the Central Pocket in Human Transcription Factor TEAD as a Potential Cancer Therapeutic Strategy," Structure, 2015, 23: 2076-2086.
Resh, "Trafficking and signaling by fatty-acylated and prenylated proteins," Nat Chem Biol, 2006, 2: 584-590.
Resh, "Use of analogs and inhibitors to study the functional significance of protein palmitoylation," Methodsm 2006, 40: 191-197.
Roth et al., "Global analysis of protein palmitoylation in yeast," Cell, 2006, 125: 1003-1013.
Smotrys and Linder, "Palmitoylation of intracellular signaling proteins: regulation and function," Annu Rev Biochem, 2004, 73: 559-587.
Sorrentino et al., "Metabolic control of YAP and TAZ by the mevalonate pathway," Nat. Cell, Biol., 2014, 16: 357-366.
Tian et al., "Structural and functional analysis of the YAP-binding domain of human TEAD2," PNAS, 2010, 107: 7293-7298.
Turnbull et al., "Structure of palmitoylated BET3: insights into TRAPP complex assembly and membrane localization," Embo J, 2005, 24: 875-884.
Wan et al., "Palmitoylated proteins: purification and identification," Nat Protoc, 2007, 2: 1573-1584.
Wu et al., "The TEAD/TEF family protein Scalloped mediates transcriptional output of the Hippo growth-regulatory pathway," Dev Cell, 2008, 14: 388-398.
Yang et al., "Screening with a novel cell-based assay for TAZ activators identifies a compound that enhances myogenesis in C2Cl2 cells and facilitates muscle repair in a muscle injury model," Mol Cell Biol, 2014, 34: 1607-1621.
Yang et al., "Submicromolar concentrations of palmitoyl-CoA specifically thioesterify cysteine 244 in glyceraldehyde-3-phosphate dehydrogenase inhibiting enzyme activity: a novel mechanism potentially underlying fatty acid induced insulin resistance," Biochemistry, 2005, 44, 11903-11912.
Yount et al., "Palmitoylome profiling reveals S-palmitoylation-dependent antiviral activity of IFITM3," Nat Chem Biol, 2010, 6: 610-614.
Zhang et al., "Photoreceptor cGMP phosphodiesterase delta subunit (PDEdelta) functions as a prenyl-binding protein," J Biol Chem, 2004, 279: 407-413.
Zhang et al., "VGLL4 functions as a new tumor suppressor in lung cancer by negatively regulating the YAP-TEAD transcriptional complex," Cell Res, 2014, 24: 331-343.
Zhao et al., "TEAD mediates YAP-dependent gene induction and growth control," Genes & Development, 2008, 22: 1962-1971.
Zheng et al., "2-Bromopalmitate analogues as activity-based probes to explore palmitoyl acyltransferases," J Am Chem Soc, 2013, 135: 7082-7085.
Zheng et al., "Clickable analogue of cerulenin as chemical probe to explore protein palmitoylation," ACS Chem Biol, 2015, 10: 115-121.
Zhou et al., "Mst1 and Mst2 maintain hepatocyte quiescence and suppress hepatocellular carcinoma development through inactivation of the Yap1 oncogene," Cancer Cell, 2009, 16: 425-438.
Zhou et al., "Targeting Hippo pathway by specific interruption of YAP-TEAD Interaction using cyclic YAP-like peptides," Faseb J, 2015, 29: 724-732.
Bedadurge & Shaikh, "Designing Hypothesis of 2-Substituted-N-[4-(1-methyl-4,5-diphenyl1H-imidazole-2-yl)phenyl] Acetamide Analogs as Anticancer Agents: QSAR Approach," Journal of the Korean Chemical Society, Dec. 2013, 57(6):744-754.
Database PubChem Compound [Online] May 30, 2009 (May 30, 2009), retrieved from NCBI Database accession No. 41931789 URL <https://pubchem.ncbi.nlm.nih.gov/compound/41931789>, 9 pages.
Database PubChem Compound [Online] Jul. 16, 2005 (Jul. 16, 2005),retrieved from NCBI Database accession No. 2513683, URL <https://pubchem.ncb.nlm.nih.gov/compound/2513683#section=Substances-by-Category>, 10 pages.
Database Registry [Online] Chemical Abstracts Service, Columbus, Ohio, US; Nov. 21, 2007 (Nov. 21, 2007), retrieved from STN Database accession No. 955199-09-4.
Database Registry [Online] Chemical Abstracts Service, Columbus, Ohio, US; Sep. 26, 2007 (Sep. 26, 2007), retrieved from STN Database accession No. 94 8157-71-9.
Database Registry [Online] Chemical Abstracts Service, Columbus, Ohio, US; Feb. 27, 2005 (Feb. 27, 2005), retrieved from STN Database accession No. 838812-50-3.

(56) References Cited

OTHER PUBLICATIONS

Database Registry [Online] Chemical Abstracts Service, Columbus, Ohio, US; Feb. 17, 2005 (Feb. 17, 2005), retrieved from STN Database accession No. 832687-05-5.
Database Registry [Online] Chemical Abstracts Service, Columbus, Ohio, US; Feb. 15, 2005 (Feb. 15, 2005), retrieved from STN Database accession No. 831247-17-7.
Database Registry [Online] Chemical Abstracts Service, Columbus, Ohio, US; Jul. 27, 2006 (Jul. 28, 2006), retrieved from STN Database accession No. 896657-58-2.
Database Registry [Online] Chemical Abstracts Service, Columbus, Ohio, US; Jul. 27, 2004 (Jul. 27, 2004), retrieved from STN Database accession No. 717130-47-7.
Database Registry [Online] Chemical Abstracts Service, Columbus, Ohio, US; Jan. 7, 2002 (Jan. 7, 2002), retrieved from STN Database accession No. 380572-22-5.
EP Extended European Search Report in EP Appln. No. 16849687.5, dated Jul. 22, 2019.
Yan et al, "Exploration of the linkage elements of porcupine antagonists led to potent Wnt signaling pathway inhibitors," Bioorganic & Medicinal Chemistry, 2015, 23(21):6855-6868.
Yurttas et al, "Synthesis and antitumor activity evaluation of new 2-(4-aminophenyl) benzothiazole derivatives bearing different heterocyclic rings," Journal of Enzyme Inhibition and Medicinal Chemistry, Sep. 2014, 30(3):458-465.
Yurttas et al, "Synthesis and anticancer activity evaluation of N-[4-(2-methylthiazol-4-yl) phenyl] acetamide derivatives containing (benz) azole moiety," Journal of Enzyme Inhibition and Medicinal Chemistry, 29(2):175-184, 2014.
EP Office Action in European Appln. No. 16849687, dated Mar. 26, 2020, 3 pages.

\* cited by examiner

C2C12 TEAD1 stable cell lines

Transient transfection of Myc-TEAD1 in HeLa cell

WT

GMR>yki$^{PD}$

GMR>sd$^{WT}$

GMR>yki$^{PD}$+sd$^{WT}$

GMR>sd$^{PCS}$

GMR>yki$^{PD}$+sd$^{PCS}$

Palmitoylation MGH-CP-1

TEAD TRANSCRIPTION FACTOR AUTOPALMITOYLATION INHIBITORS

RELATED APPLICATIONS

This application is a National Stage Application filed under 35 U.S.C. § 371 of International Application PCT/US2016/053318, filed Sep. 23, 2016, which claims the benefit of U.S. Provisional Application Ser. No. 62/222,238, filed Sep. 23, 2015, and U.S. Provisional Application Ser. No. 62/306,421, filed Mar. 10, 2016, the disclosures of each of which are incorporated herein by reference in their entirety.

GOVERNMENT SUPPORT

This invention was made with government support under Grant No. 1RO1CA181537-01A1 awarded by the National Institutes of Health. The government has certain rights in the invention.

TECHNICAL FIELD

The present application is concerned with pharmaceutically useful compounds. The disclosure provides new compounds as well as their compositions and methods of use. The compounds inhibit the autopalmitoylation of TEAD-transcription factors and are therefore useful in the treatment of diseases related to the activity of TEAD-transcription factors including, e.g., cancers and other diseases.

BACKGROUND

Hippo signaling plays key roles in organ size control and tumor suppression. The signal transduction involves a core kinase cascade, including MST1/2 and Lats1/2 kinases, leading to YAP/TAZ phosphorylation, cytoplasmic retention and inhibition[3]. Physiological or pathological inactivation of these kinases leads to YAP/TAZ dephosphorylation and nuclear accumulation. Subsequently, nuclear YAP/TAZ binds to the TEA domain transcription factors (TEAD1-4 in mammals, and Scalloped in *Drosophila*) to mediate the target genes expression. The TEAD-YAP complex regulates normal development of skin, muscle, lung and liver, and are also oncogenic factor amplified in many human cancers. TEADs can also bind to Vgll4, which has been implicated as a tumor suppressor by competing with YAP/TAZ for TEADs binding. Therefore, TEADs are essential in regulating the transcriptional output of Hippo pathway. Although targeting TEAD-YAP could be a promising therapeutic approach for diseases with deregulated Hippo pathway, it remains challenging to directly inhibit transcription factors with small molecules. Therefore, understanding the regulation of TEADs might reveal new therapeutic opportunities for drug discovery.

Post-translational S-palmitoylation attaches a 16-carbon palmitate to the cysteine residue through a reversible thioester bond. A large number of palmitoylated proteins have been identified through proteomic studies. Dynamic S-palmitoylation plays critical roles regulating the trafficking, membrane localization and functions of many proteins, including Src-family kinases, GTPases, and synaptic adhesion molecules. Asp-His-His-Cys (DHHC) family proteins are evolutionarily conserved protein palmitoyl acyltransferases (PATs), mediating enzymatic S-palmitoylation. In addition, some proteins could bind to palmitoyl-Coenzyme A (CoA) directly, and undergo PAT-independent autopalmitoylation. However, autopalmitoylation is poorly characterized. Most of the reported examples of autopalmitoylation are observed under non-physiological, high concentration of palmitoyl-CoA (>100 μM). To date, only a few proteins, including yeast transporter protein Bet3, are autopalmitoylated under physiological concentrations of palmitoyl-CoA (1-10 μM). Therefore, it is important to reveal additional autopalmitoylated proteins and to understand their regulations and functions.

SUMMARY

The present disclosure provides, inter alia, a compound of Formula (I):

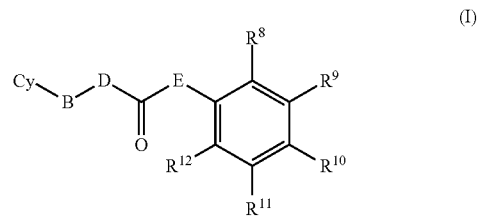

or a pharmaceutically acceptable salt thereof; wherein the variables are as defined below.

The present disclosure also provides a composition comprising a compound of Formula (I), or a pharmaceutically acceptable salt thereof, and at least one pharmaceutically acceptable carrier.

The present disclosure also provides methods of treating cancer and other diseases comprising administering to a patient a therapeutically effective amount of a compound of Formula (I), or a pharmaceutically acceptable salt thereof.

The details of one or more embodiments are set forth in the description below. Other features, objects and advantages will be apparent from the description and from the claims.

DETAILED DESCRIPTION

Figure 1A:
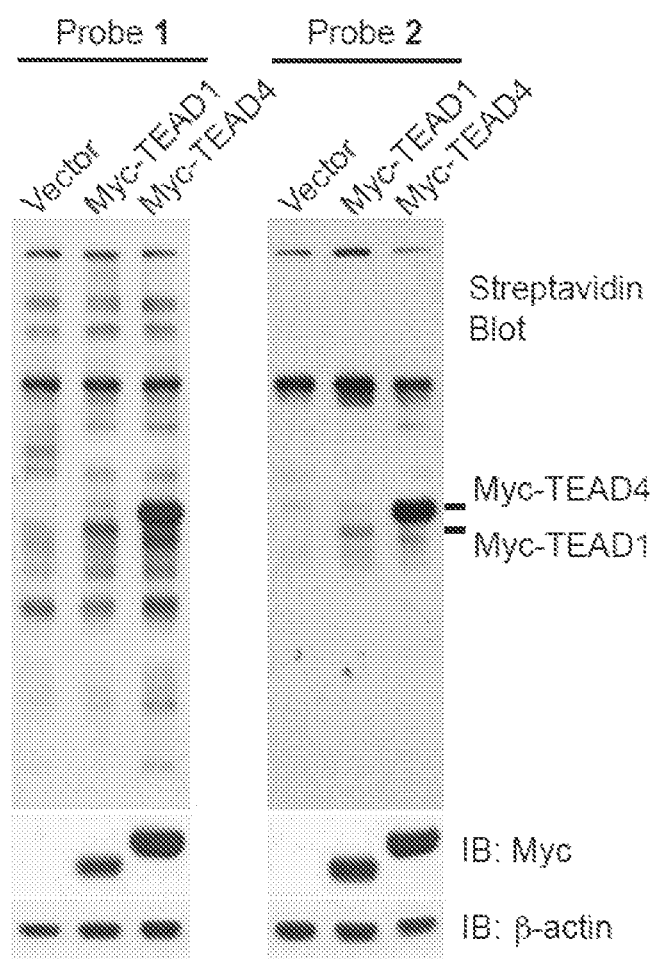
FIG. 1A is a Streptavidin blot of probe 1 and 2 labeled myc-TEAD1 and myc-TEAD4 in HEK293A cells, showing the palmitoylation of TEADs.

For the terms "e.g." and "such as," and grammatical equivalents thereof, the phrase "and without limitation" is understood to follow unless explicitly stated otherwise.

The singular forms "a," "an," and "the" include plural referents unless the context clearly dictates otherwise.

The term "about" means "approximately" (e.g., plus or minus approximately 10% of the indicated value).

The inventors have developed activity-based chemical probes based on irreversible inhibitors of PATs, 2-bromopalmitate (2-BP) and cerulenin, which inhibit palmitoylating activities by alkylating the active site cysteines of the enzymes or autopalmitoylated proteins. Analogues of 2-BP and cerulenin with an alkyne tail have been synthesized, which serve as bioorthogonal chemical reporters for covalently labeling and profiling PATs and autopalmitoylated proteins. Through proteomic and biochemical studies, it has been identified that the TEAD transcription factors are palmitoylated at evolutionarily conserved cysteine residues. It has been found that TEADs undergo PAT-independent autopalmitoylation, under physiological concentrations of palmitoyl-CoA. The crystal structures of the lipid-bound TEADs, and revealed a new ligand-binding site in TEADs. Furthermore, autopalmitoylation plays critical roles in regulating TEAD-YAP association and their physiological functions in vitro and in vivo. Therefore, palmitoylation of TEADs plays important roles in regulating Hippo pathway transcriptional complexes.

The discovery of a new ligand-binding site in TEADs has allowed the discovery of small molecule inhibitors of TEAD autopalmitoylation. While not being bound by any theory, it is understood that the ligands bind to the palmitate-binding pocket, and inhibit TEAD-YAP interaction, cancer cell proliferation and migration. Therefore, direct inhibition of TEAD autopalmitoylation activities is useful to inhibit these oncogenic transcription factors.

I. Results

A. TEAD Transcription Factors are Palmitoylated

To detect protein palmitoylation, analogues of palmitate, such as 15-hexadecynoic acid (1), have been used as chemical reporters to metabolically label palmitoylated proteins (substrates). To explore PATs and autopalmitoylated proteins, the activity-based chemical probes, 2-bromohexadec-15-ynoic acid (2) and cis-2,3-epoxy-4-oxooctadec-17-ynamide (3), were prepared. Labeling, enrichment and proteomic analysis of the probe-labeled proteins and showed that 2 and 3 can covalently label>300 proteins, including several known PATs and acyltransferases.

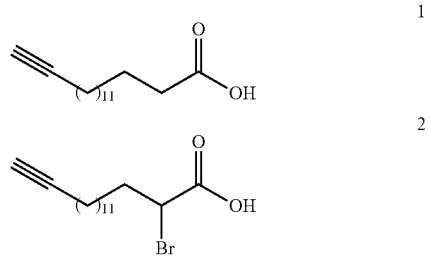

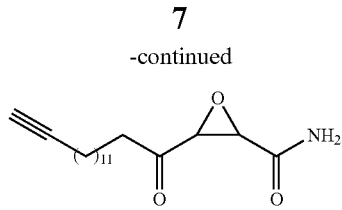

3

Among the hits from chemoproteomic studies, the TEA domain (TEAD/TEF) transcription factors (TEAD1 and TEAD3) were identified that have unique matching peptides in proteomic studies.

TEADs bind to the transcription co-activator YAP/TAZ, and regulate the transcriptional output of Hippo pathway, which plays critical roles in organ size control, regeneration and tumorigenesis. To validate that TEADs are palmitoylated, Myc-TEAD1 and TEAD4 constructs were transfected in HEK293A cells; and then labeled cells with 50 μM of 1 or 2, followed by Cu-catalyzed 1,3-dipolar cycloaddition (Click reaction) with biotin-azide, and detection with streptavidin blots. Myc-TEAD1 and TEAD4 are indeed labeled by both probes (FIG. 1A), suggesting that TEADs are palmitoylated.

To characterize whether endogenous TEAD proteins are palmitoylated, HEK293A and MCF10A cells were metabolically labeled with 1, followed by Click reaction with biotin-azide. The palmitoylated proteins were then enriched by streptavidin beads pull-down. All four endogenous human TEADs (TEAD1-4) were detected in the pull-down samples by western blots (FIG. 1B), indicating that they were indeed palmitoylated in cells. TEAD2 and 4 were not among the hits in chemical proteomics studies, possibly due to their low abundance, and the stringent criteria used for mass spectra analysis. Nevertheless, detailed biochemical experiments confirmed that all TEADs should be palmitoylated in cells.

Figure 1B:
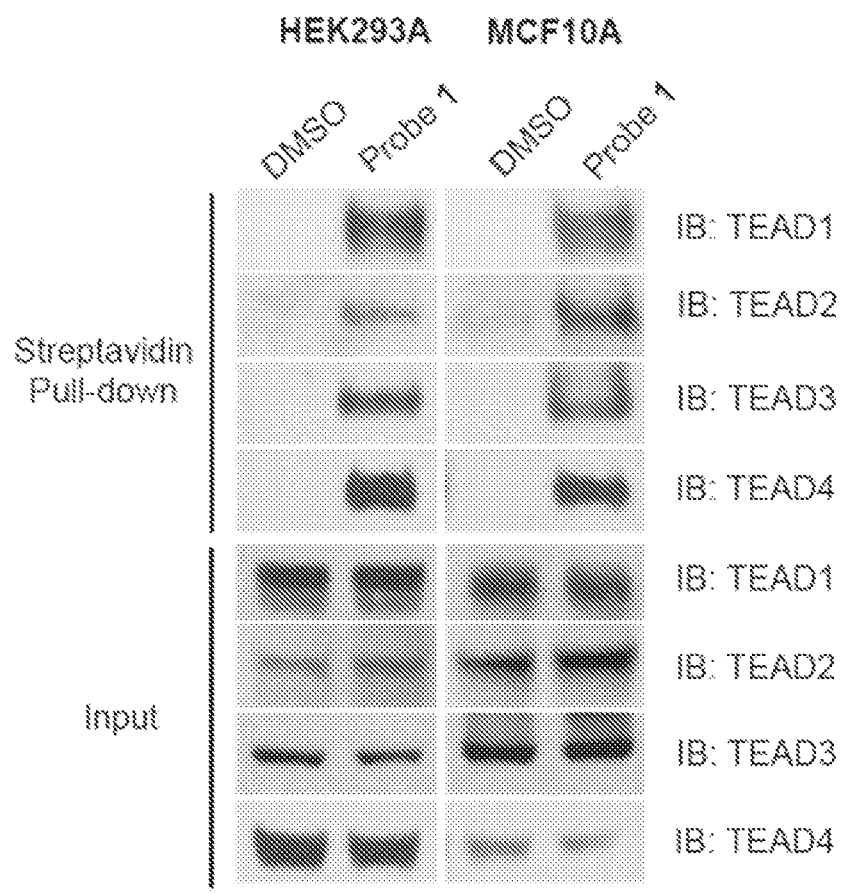
FIG. 1B are Western blots of TEAD1-4 showing endogenous human TEAD1-4 are all palmitoylated.
Figure 1C:
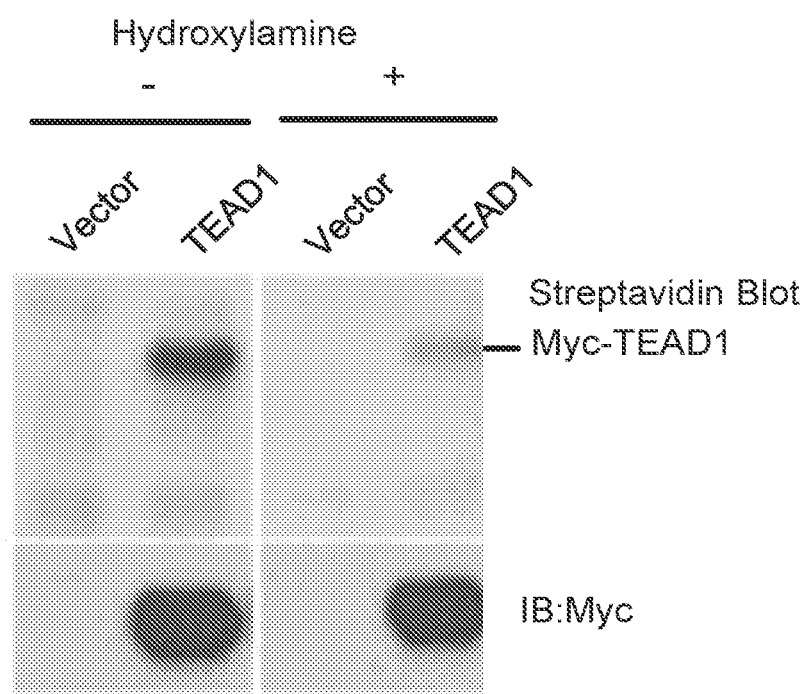
FIG. 1C is a Streptavidin blot showing S-palmitoylated and hydroxylamine treatment dramatically decreased TEAD1 palmitoylation levels.

Treatment of hydroxylamine dramatically reduced the palmitoylation levels in TEAD1, suggesting that TEADs are S-palmitoylated through a reversible thioester linkage (FIG. 1C).

Figure 1D:
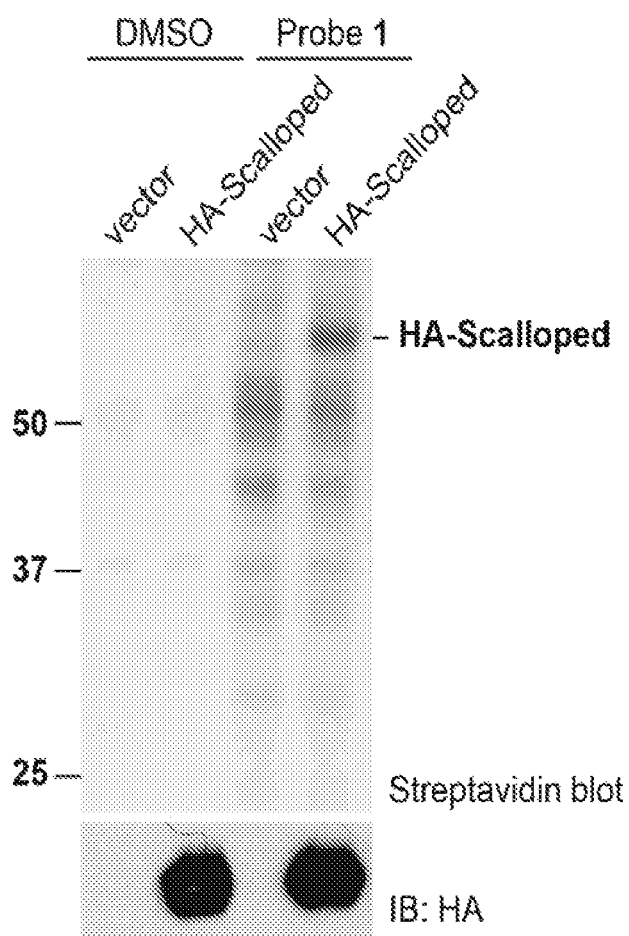
FIG. 1D is a Streptavidin blot showing that *Drosophila* Scalloped protein is palmitoylated.
Figure 1E:
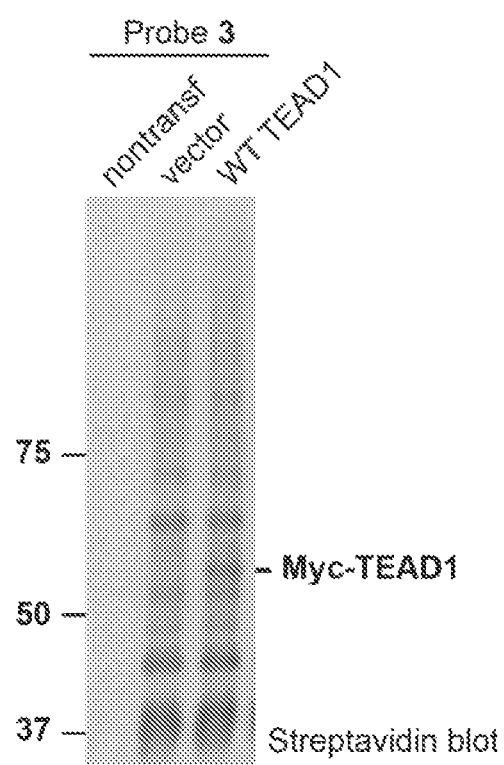
FIG. 1E is a blot showing labelling of probe 3 labeled TEAD1 in HEK293A cells.

It was shown that *Drosophila* Scalloped protein is palmitoylated suggesting that TEAD palmitoylation is evolutionarily conserved. HEK293A cells were transfected with empty vector or wild type HA-Scalloped. Cells were labeled with 50 μM Probe 1 overnight, lysed and followed by click reaction. Proteins were resolved by SDS-PAGE and biotin-linked proteins were detected by streptavidin blot. The results are shown in FIG. 1D), In addition, it was shown that TEAD1 can be labeled by 3. HEK293A cells were transfected with nothing, empty vector or wild type Myc-TEAD1. Cells were labeled with 5 μM of 3 overnight, lysed and followed by click chemistry reaction. Proteins were resolved by SDS-PAGE and biotin-linked proteins were detected by streptavidin blot. The results are shown in FIG. 1E.

Taken together, the results show that TEAD family transcription factors are S-palmitoylated.

B. TEADs are Palmitoylated at Conserved Cysteine Residues

Figure 2A:
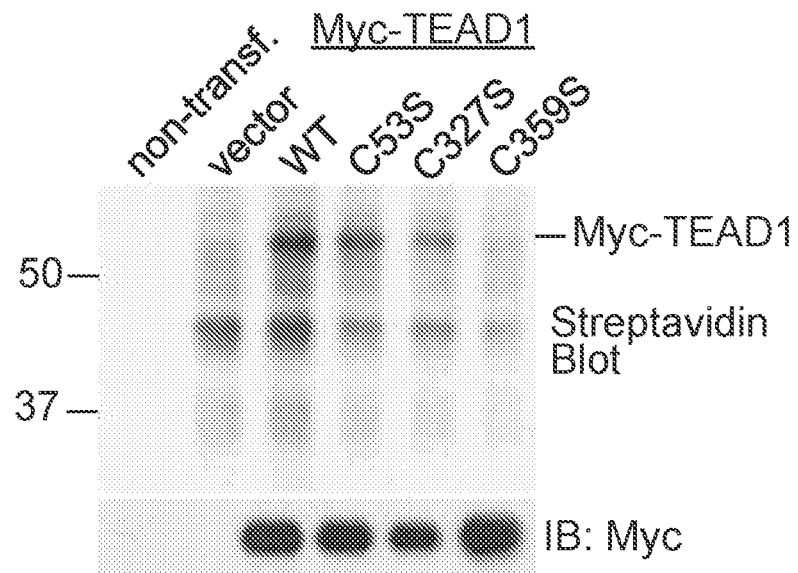
FIG. 2A is a Streptavidin blot showing mutation of the conserved cysteine residues (C53, C327 and C359) to serine residues individually blocked palmitoylation of TEAD1.
Figure 2B:
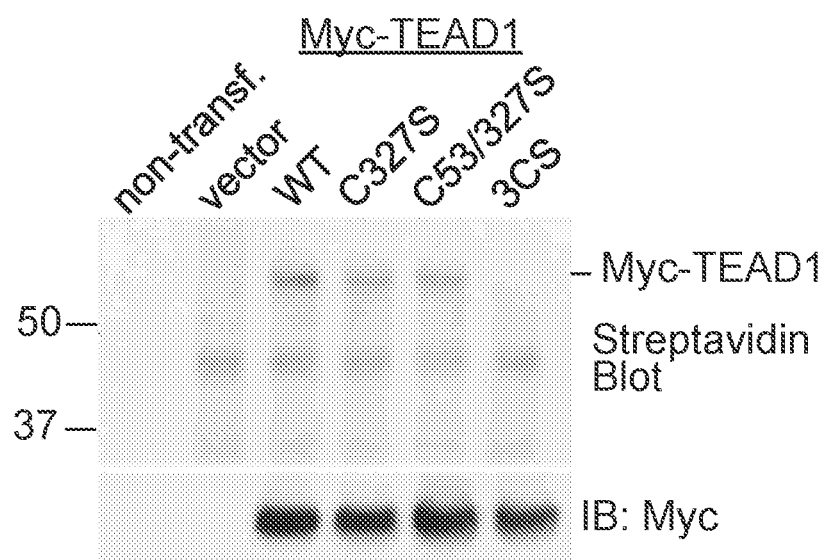
FIG. 2B is a Streptavidin blot showing mutation of the conserved cysteine residues (C53, C327 and C359) to serine residues in combination blocked palmitoylation of TEAD1.

To identify the sites of palmitoylation in TEAD, sequences of TEAD family of proteins were aligned across different species, including human, *Xenopus*, zebra fish, *Drosophila*, and *C. elegans*. Three cysteine residues were found that are evolutionarily conserved. These residues were mutated to serine in human TEAD1 (C53S, C327S and C359S) to test whether the mutation affects TEAD1 palmitoylation. The C359S mutant showed the greatest loss of palmitoylation, and C327S and C53S also showed decreased palmitoylation (FIG. 2A). These results suggest that C359 plays a critical role in TEAD1 palmitoylation, and can be a major site of modification. Furthermore, combination mutation of all three cysteine residues, C53/327/359S (3CS), completely ablated TEAD1 palmitoylation (FIG. 2B), indicating that these residues are indeed involved for TEAD1 palmitoylation.

C. TEADs Undergo PATs-Independent Autopalmitoylation

Figure 2C:
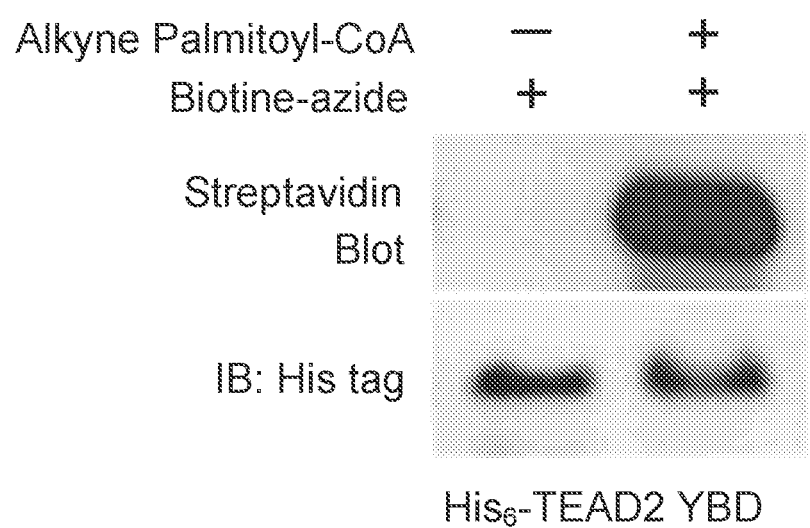
FIG. 2C is a Streptavidin blot showing recombinant TEAD2 protein (YAP binding domain, YBD) is autopalmitoylated in vitro in the presence of alkyne palmitoyl-CoA.

The fact that TEADs could be labeled by Probe 2 and 3 (FIG. 1B, FIG. 1E), suggested that TEADs may possess palmitoylating enzyme-like activities and undergo autopalmitoylation. Purified recombinant TEAD2 protein has previously been reported, Tian et al., *Proc. Natl. Acad. Sci. USA*, 2010, 107, 7293-7298, which allows in vitro experiments using TEAD2 to be carried out. hTEAD2 (full-length or YAP-binding domain (YBD): TEAD2$^{217-447}$) was incubated with a clickable analogue of palmitoyl-CoA (15-hexadecynoic CoA) at neutral pH in vitro, followed by Click reaction with biotin-azide and streptavidin blot. Both TEAD2 full-length and the YBD were palmitoylated in vitro in the absence of PATs (FIG. 2C).

Figure 2D:
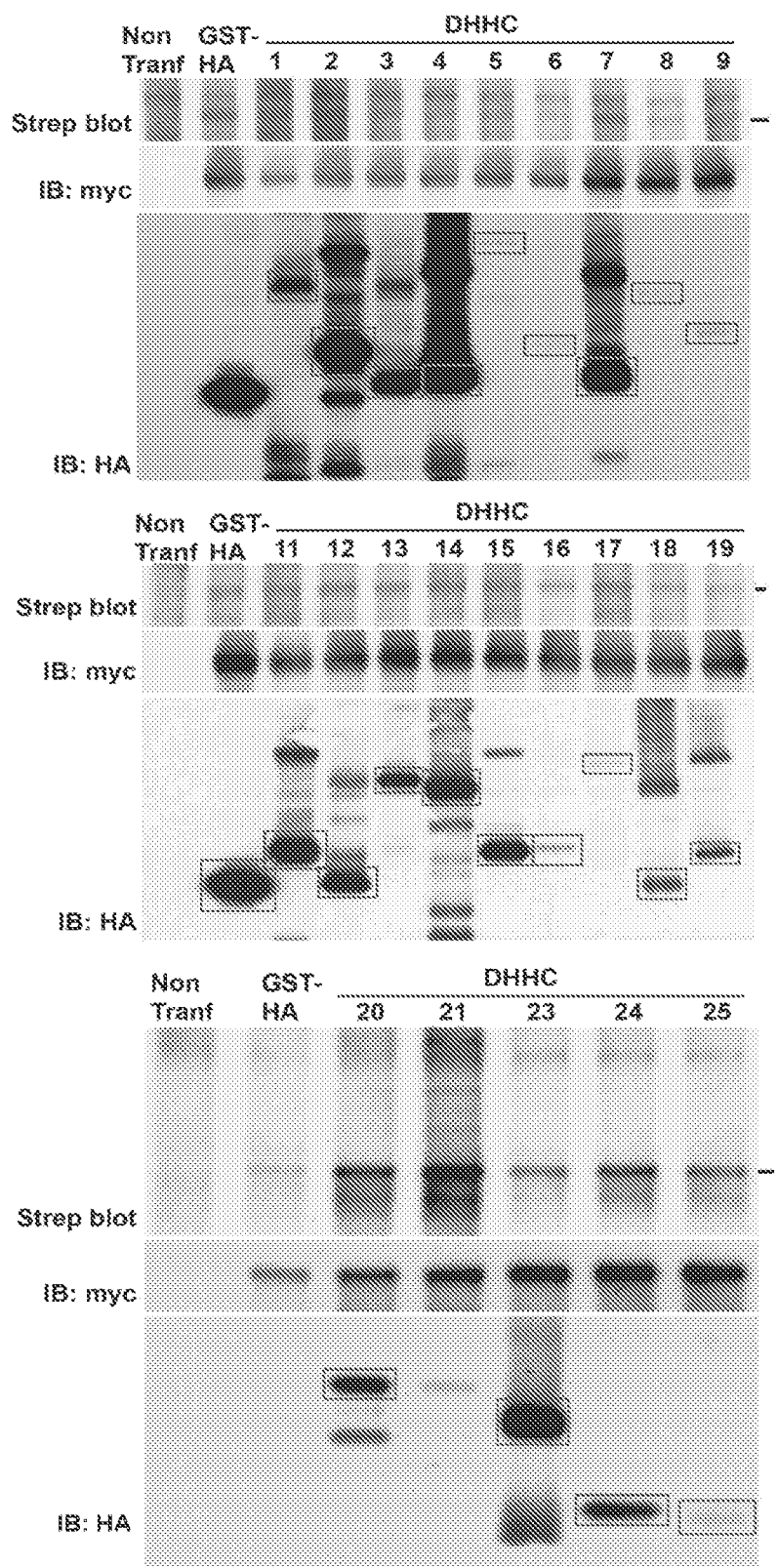
FIG. 2D is an image of Streptavidin blots and anti-myc-c-antibody blots showing that DHHC-family PATs did not significantly alter the palmitoylation levels of TEAD1 in cells.

In addition, it was shown that overexpression of each of the DHHC-family PATs did not significantly alter the palmitoylation levels of TEAD1 in cells (FIG. 2D). HEK293A cells were transfected with nothing, control vector, wild type Myc-TEAD1 and/or HA-DHHC. Cells were labeled with 50 μM Probe 1 overnight, lysed and followed by click chemistry reaction. Proteins were resolved by SDS-PAGE and TEAD protein was detected by streptavidin blot and anti-c-myc antibody. Total DHHC protein was detected by anti-HA antibody. This confirmed that TEAD palmitoylation is independent of PATs.

Figure 2E:
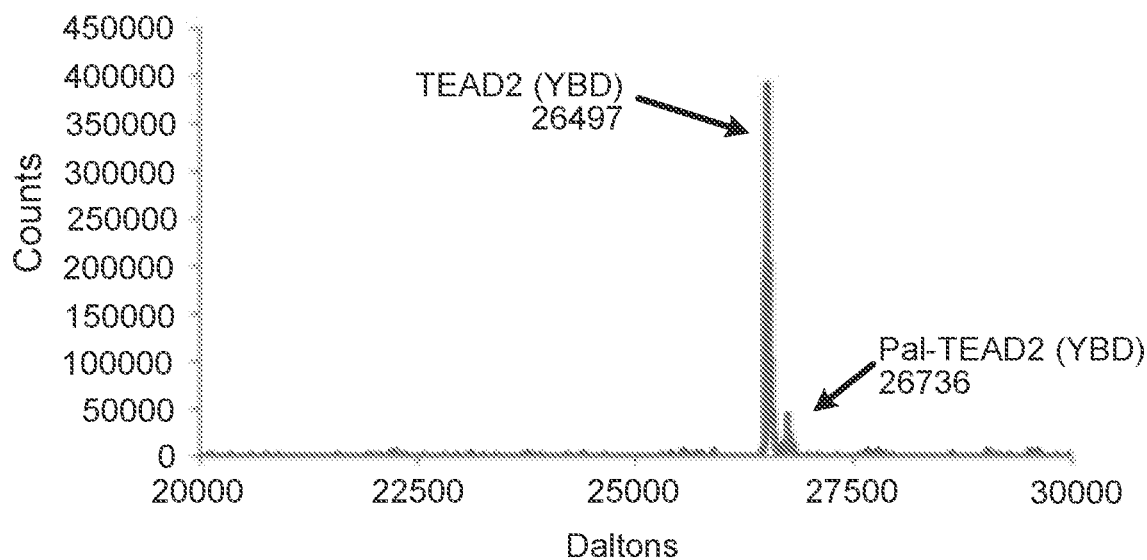
FIG. 2E is a mass spectrometry analysis of recombinant TEAD2 YBD showing palmitoylation of TEAD2.
Figure 2F:
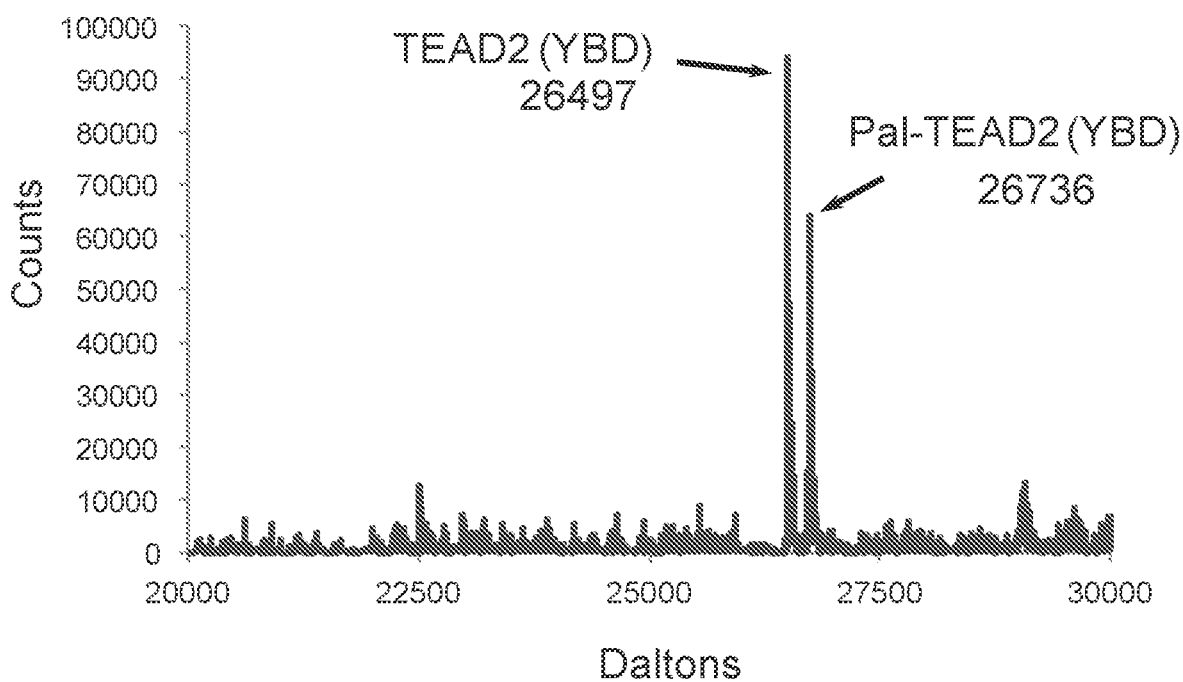
FIG. 2F is a mass spectrogram showing increased palmitoylation of recombinant TEAD2 YBD when incubated with palmitoyl-CoA in vitro.
Figure 2G:
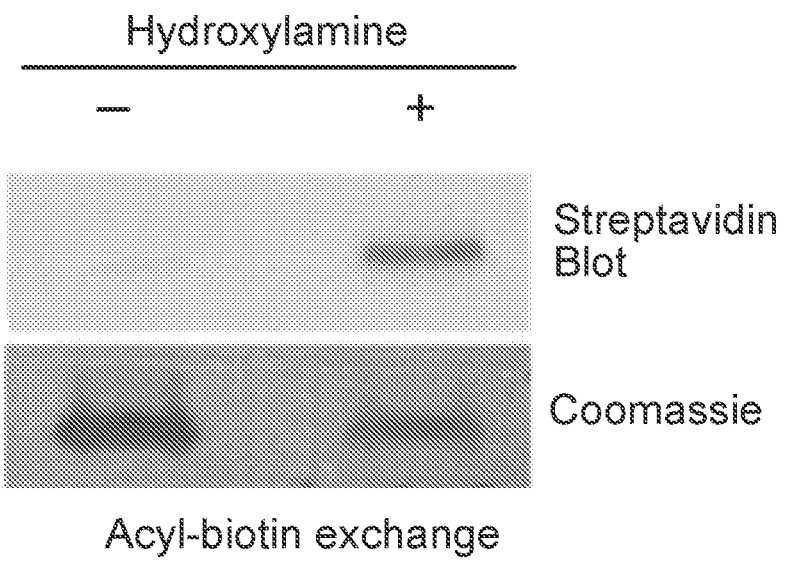
FIG. 2G is a Streptavidin blot of an acyl-biotin exchange (ABE) assay confirming autopalmitoylation of recombinant TEAD2 YBD.
Figure 2H:
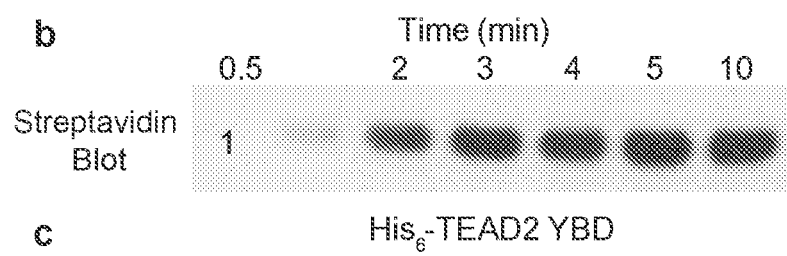
FIG. 2H is a Streptavidin blot showing time-dependent autopalmitoylation of recombinant TEAD2 YBD in vitro.
Figure 2I:
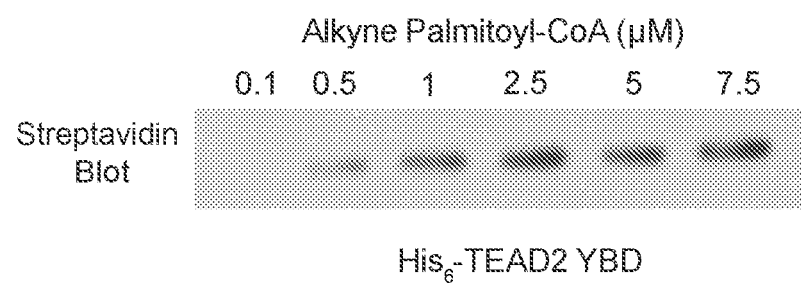
FIG. 2I is a Streptavidin blot showing palmitoyl-CoA dose-dependent autopalmitoylation of recombinant TEAD2 YBD in vitro.
Figure 2J:
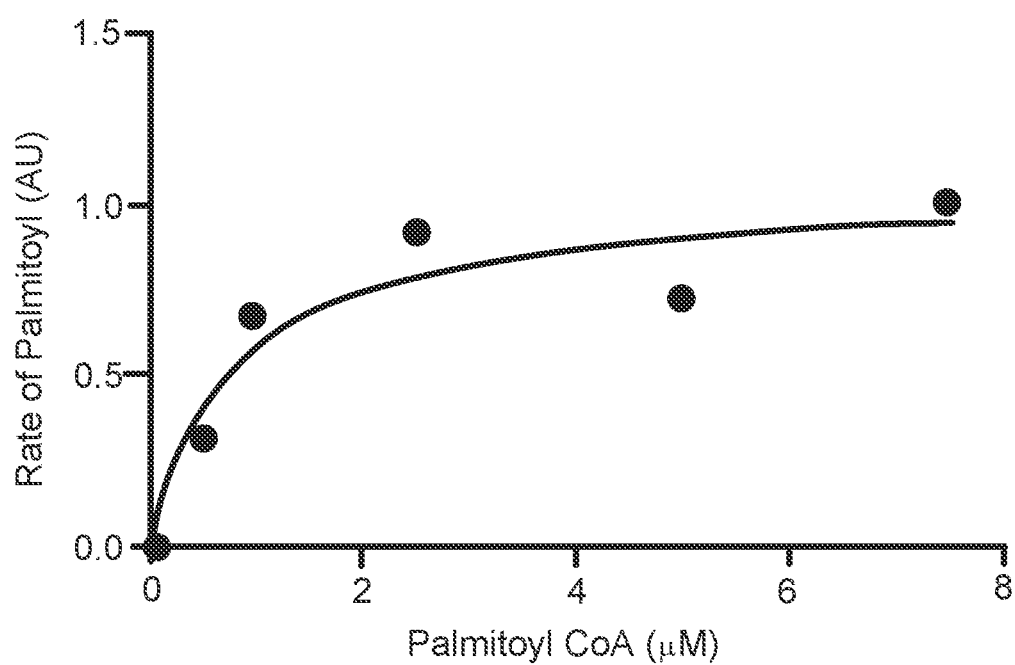
FIG. 2J is a graph of concentration of palmitoyl-CoA (μM) versus rate of palmitoylation (AU). The $K_m$ value of palmitoyl-CoA in TEAD2 autopalmitoylation is about 0.8 μM.

Intact mass spectrometry analysis of the recombinant TEAD2-YBD was carried out. The peak corresponding to unmodified TEAD2 at 26497 Dalton. A small side peak was also observed at 26736 Dalton (FIG. 2E), consistent with a palmitate modification to the protein. These results suggest that a small fraction of the recombinant TEAD2-YBD is palmitoylated when expressed in bacteria. In addition, after incubating with palmitoyl-CoA in vitro, we observed that the abundance of the palmitoylated TEAD2 peak (26736 Dalton) increased significantly (FIG. 2F), further confirming that TEAD2 can be autopalmitoylated. Moreover, auto-palmitoylation of TEAD2 YBD was confirmed by acyl-biotin exchange (ABE) assay, which converts S-palmitoylation to stable biotinylation for detection (FIG. 2G). With 1 μM of palmitoyl-CoA at neutral pH, TEAD2 YBD was autopalmitoylated within 2 min, and the palmitoylation levels reached saturation after 10 min (FIG. 2H). To determine dose-dependency of palmitoyl-CoA, recombinant TEAD2 YBD was incubated with various concentrations of alkyne palmitoyl-CoA for 3 min, and the reaction rate was determined by quantifying the intensities of streptavidin blots (FIG. 2I). The apparent $K_m$ of palmitoyl-CoA in TEAD2 autopalmitoylation was estimated at about 0.8 μM (FIG. 2J), which is comparable to the $K_m$ of DHHC-family PATs. The physiological palmitoyl-CoA concentrations range from 100 nM to 10 μM in cells. Therefore, the results indicated that TEAD palmitoylation could occur under normal physiological conditions.

D. Structural Analysis of Palmitoylation of TEADs

Figure 3A:
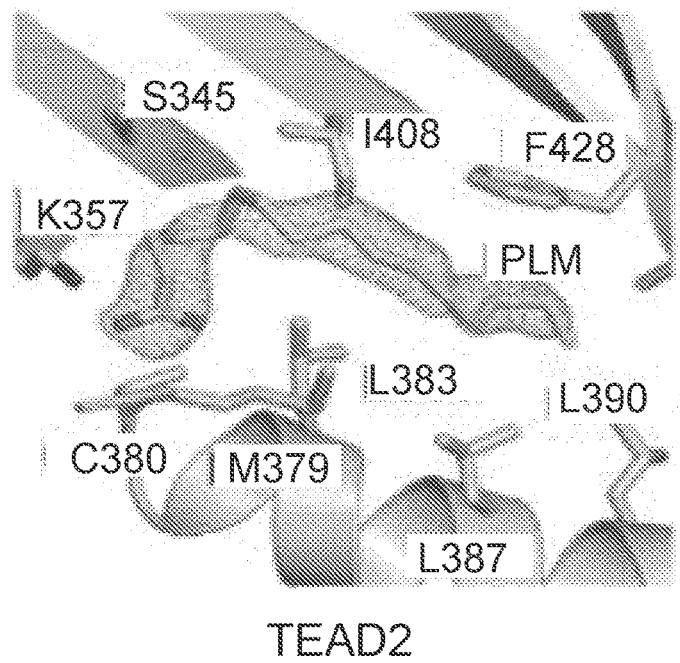
FIG. 3A is a $F_o$-$F_c$ omit electron density map for TEAD2 at the contour level of 2.5σ.
Figure 3B:
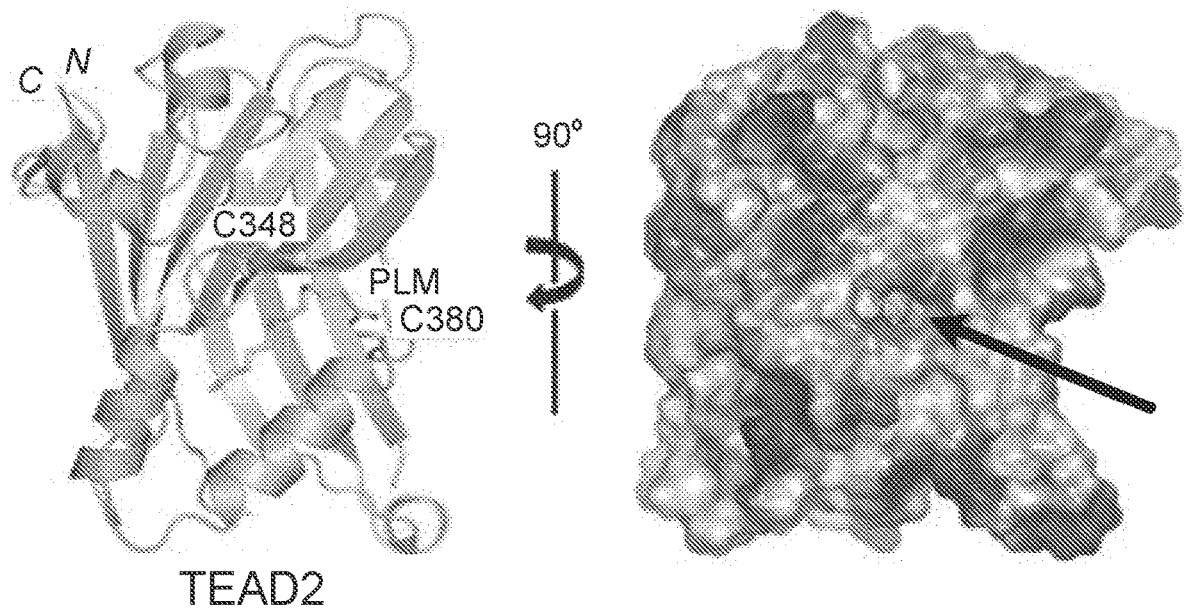
FIG. 3B is a ribbon diagram (left) and electrostatic surface (right) of PLM-bound TEAD2 YBD (PDB code: 5HGU).

To reveal the structural basis of lipid modification of TEADs, X-ray crystallography was carried out of TEAD2 YBD (residues 217-447). Human TEAD2 YBD was expressed and purified from bacteria, and determined its structure to a resolution of 2.0 Å (PDB code 5HGU) by molecular replacement with the selenomethionine-labeled TEAD2 YBD (PDB code 3L15)[27] as the search model (Table 1). Extra electron density was clearly observed in a deep hydrophobic pocket adjacent to C380 (corresponding to C359 of TEAD1), indicating that TEAD2 binds to an unknown small molecule ligand. Consistent with the results of TEAD2 palmitoylation by the chemical biology methods and mass spectrometry (FIG. 2E), the extra electron density corresponds to a 16-carbon fatty acid (palmitate, PLM) (FIG. 3A). The lipid chain of palmitate inserts deeply into the pocket, with the free carboxyl group pointing to, but not covalently attached to, C380 of TEAD2. This suggests that the palmitate might initially be covalently attached to C380, but the labile thioester bond might be cleaved during purification and crystallization under slightly basic conditions. Consistently, surface drawing of TEAD2 reveals that the carboxyl group of palmitate is solvent accessible through an opening adjacent to C380 (FIG. 3B). This opening is also large enough to allow free palmitate to diffuse in and out of the pocket. A recent report of TEAD2 structure using a slightly different purification conditions resulted in higher yield of palmitoylated TEAD2, and the covalent bond can be observed in crystal structures. Noland et al., *Structure*, 2016, 24, 1-8.

Figure 3C:
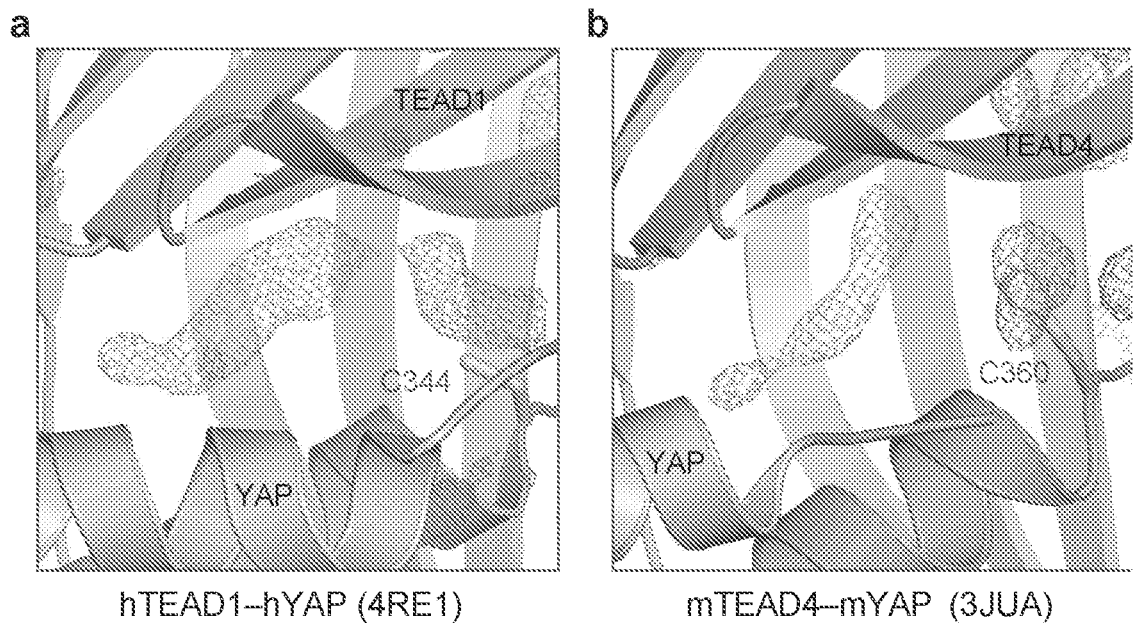
FIG. 3C is a $F_o$-$F_c$ omit electron density map for TEAD1-cyclic YAP showing (a) and mTEAD4-mYAP (b) in the deep hydrophobic pocket at the contour level of 3σ.
Figure 3D:
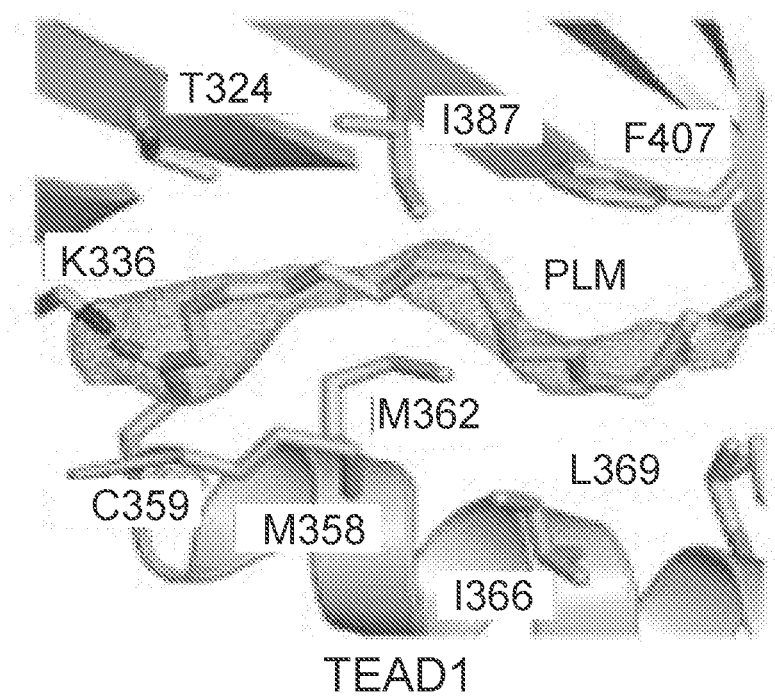
FIG. 3D is a $F_o$-$F_c$ omit electron density map for TEAD1-YAP at the contour level of 2.5σ. Palmitate is covalently linked to C359 of TEAD1.
Figure 3E:
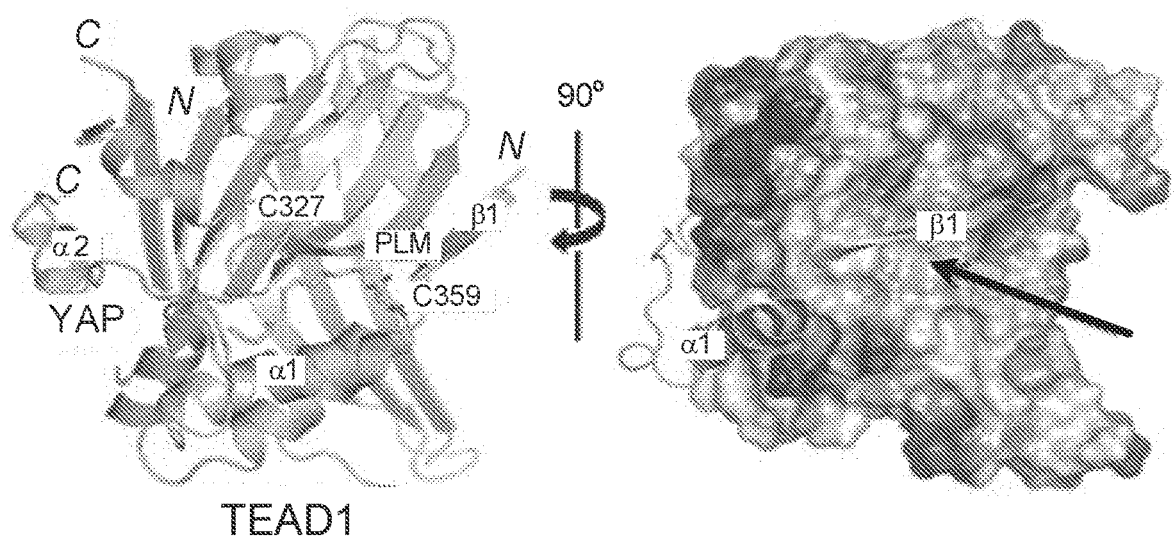
FIG. 3E is a ribbon diagram (left) and electrostatic surface (right) of PLM-bound TEAD1-YAP complex. Two conserved cysteine residues are shown.

To explore whether covalent palmitoylation could be observed in other TEAD structures. the previously reported crystal structures of human TEAD1-YAP complex (PDB code 3KYS), mouse TEAD4-YAP (PDB code 3JUA), and human TEAD1-cyclic YAP (PDB code 4RE1) were also examined. Similar lipid-like electron densities are present in all of the conserved deep pocket of these structures. In mTEAD4-YAP (3JUA), the electron density appears to be covalently connected to C360 of TEAD4. However, the electron densities in 3JUA and 4RE1 are truncated, making it difficult to assign to PLM without prior knowledge of palmitoylation (FIG. 3C). The TEAD1-YAP complex (PDB code 3KYS), which was co-expressed in bacteria and purified as a complex, showed the highest quality of electron density in the hydrophobic pocket. When the structure was refined, it was found that the electron density indeed corresponds to a palmitate, covalently linked to C359 of TEAD1 (FIG. 3D). These results are consistent with the finding that TEAD1 C359 is palmitoylated. The surface opening observed in TEAD2 alone structure is blocked by the β1 segment of YAP peptide in the TEAD1-YAP complex (FIG. 3E). The fact that the thioester bond is solvent inaccessible in the complex, together with the mild purification and crystallization conditions, might help to preserve the covalent linkage. As there are no PATs present in bacteria, these findings also confirmed the results showing that TEAD1 is autopalmitoylated. Taken together, the results show that TEADs have a conserved hydrophobic pocket occupied by a palmitate, revealing a new structural feature of these transcription factors. The lipid-binding pocket is highly conserved among other TEADs[32]. Therefore, palmitate-binding could be an important regulatory mechanism for all TEADs.

Figure 4:
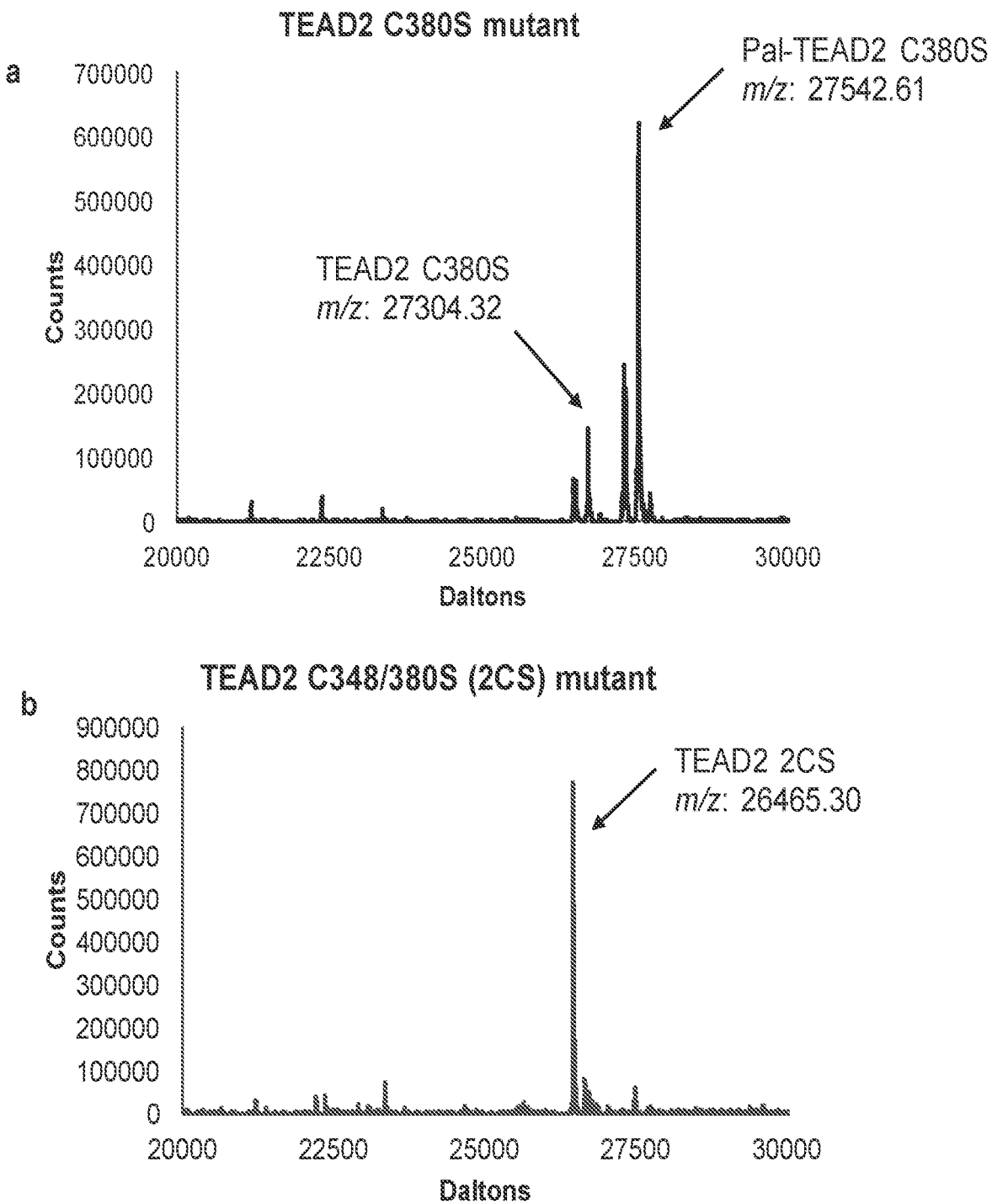
FIG. 4 is a pair of mass spectrograms showing (a) TEAD2 C380 and (b) 2CS mutants after subjecting to autopalmitoylation conditions showing that the TEAD2 C380 mutant can be palmitoylated in vitro, but the TEAD2 2CS mutant cannot be palmitoylated in vitro.

The structural studies suggested that TEAD1 C359 (corresponding to TEAD2 C380) palmitoylation is stable and can be crystallized. However, the results do not rule out the possibility that C327 (corresponding to TEAD2 C348) might be partially or transiently palmitoylated in cells. Recombinant TEAD2 C380S and C348/380S (2CS) mutants were purified. Consistent with the mutagenesis studies in FIG. 2A and FIG. 2B, mass spectrometric studies showed that a TEAD2 C380S mutant can still be autopalmitoylated in vitro, but TEAD2 2CS mutant cannot be autopalmitoylated, as shown by the results in FIG. 4. The results show that the TEAD2 C380 mutant can still be palmitoylated in vitro: the mass peak with m/z of 27304 indicates unmodified His6-tagged TEAD2 C380S protein (without the first Met), and m/z of 27542 indicates the palmitoylated His6-tagged-TEAD2 C380 protein; however, the TEAD2 2CS mutant cannot be palmitoylated in vitro: the mass peak with m/z of 27304 indicates unmodified His6-tagged TEAD2 C380S protein (without the first Met), and m/z of 26465.30 indicates the un-palmitoylated TEAD2 2CS protein (without the first Met and the C-terminal His tag). These results suggest that both C348 and C380 are involved palmitoylation, and C380 palmitoylation is more stable.

Figure 5:
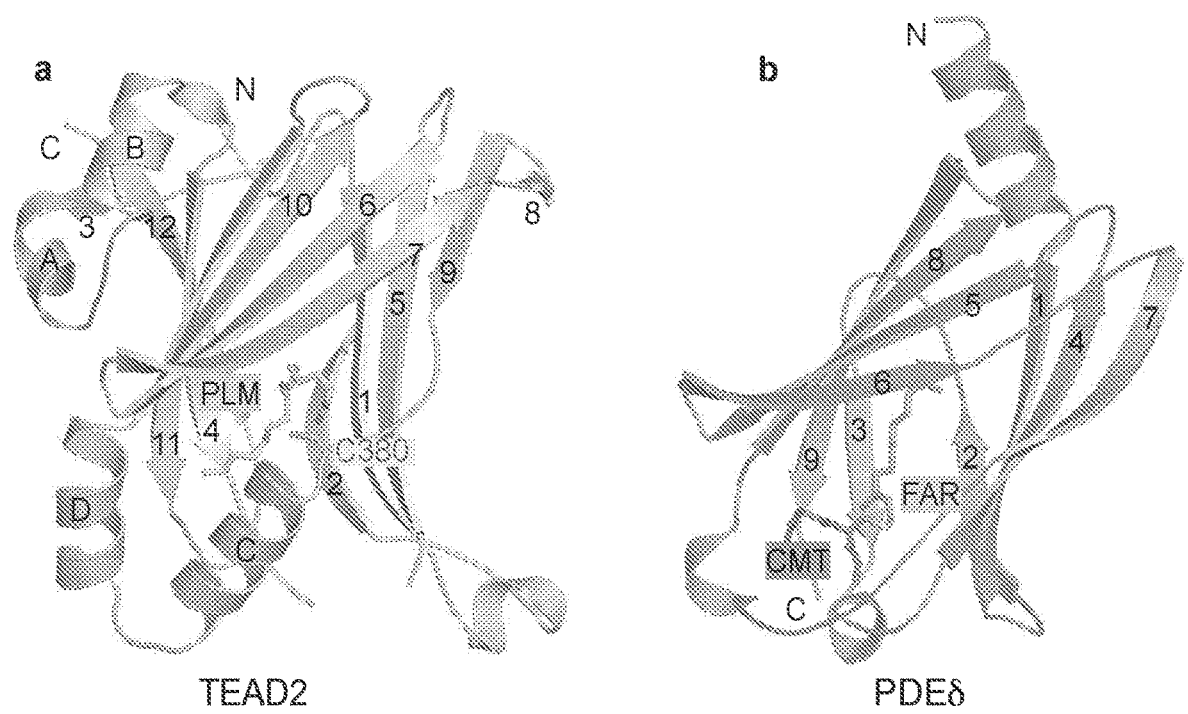
FIG. 5 is a diagram comparing the structures TEAD2 and PDEδ. The left figure shows TEAD2 with bound palmitate (PLM); the right figure shows farnesylated PDEδ (PDB code: 3T5I) with a bound farnesyl group (FAR).

It has been noted that TEADs are structurally related to phosphodiesterase δ (PDEδ, PDB code 1KSHB and 3T5I), with two β-sheets packing against each other to form a β-sandwich motif. Interestingly, PDEδ has a similar hydrophobic pocket inside the β-sandwich motif, which binds to the farnesyl chain of GTPases (FIG. 5). It is possible that such structural motif represents a common lipid-binding site, and other proteins with similar motif might also bind to lipid ligands. Interestingly, small molecule inhibitors of PDEδ can indeed bind to this pocket, and inhibit the association of PDEδ and farnesylated Ras proteins, leading to inhibition of Ras activities. Therefore, targeting such lipid-binding sites might lead to new small molecule inhibitors of important biological pathways.

E. Palmitoylation of TEAD Regulates TEAD-YAP/TAZ Association

Figure 6A:
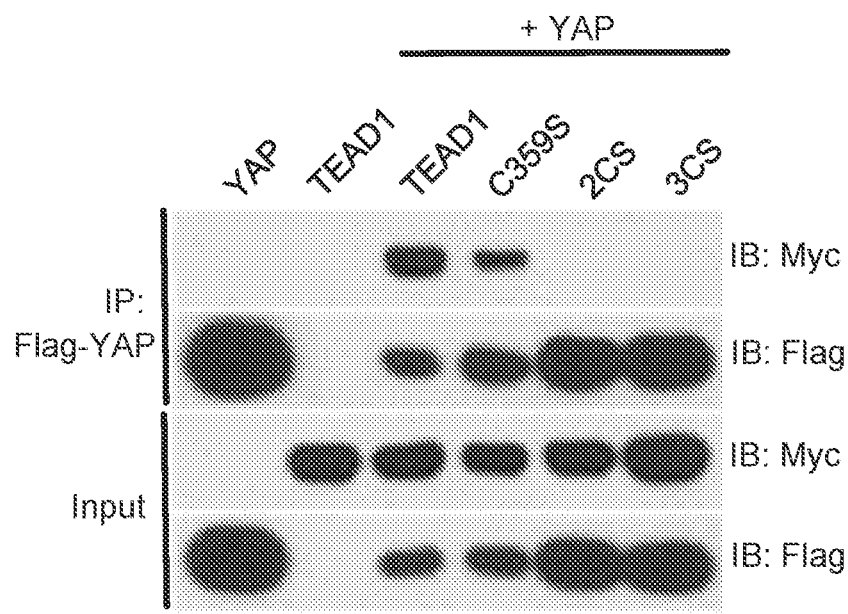
FIG. 6A is a Western blot showing palmitoylation-deficient mutants of TEAD1 (C359S, C327/359S (2CS), and 3CS) have decreased association with YAP in co-immunoprecipitation (co-IP) experiments.

Although all four TEAD proteins are palmitoylated, functional studies were performed using TEAD1, as it is one of the most abundant TEAD proteins ubiquitously expressed. As the palmitoylated cysteine (C359 of TEAD1) is located near the TEAD-YAP interface, we tested whether palmitoylation could allosterically regulate TEAD-YAP association. Indeed, it was found that YAP could co-immunoprecipitate (co-IP) with WT TEAD1, but the association was significantly reduced with the palmitoylation-deficient mutants (C359S, C327/359S (2CS) or 3CS) (FIG. 6A).

Figure 6B:
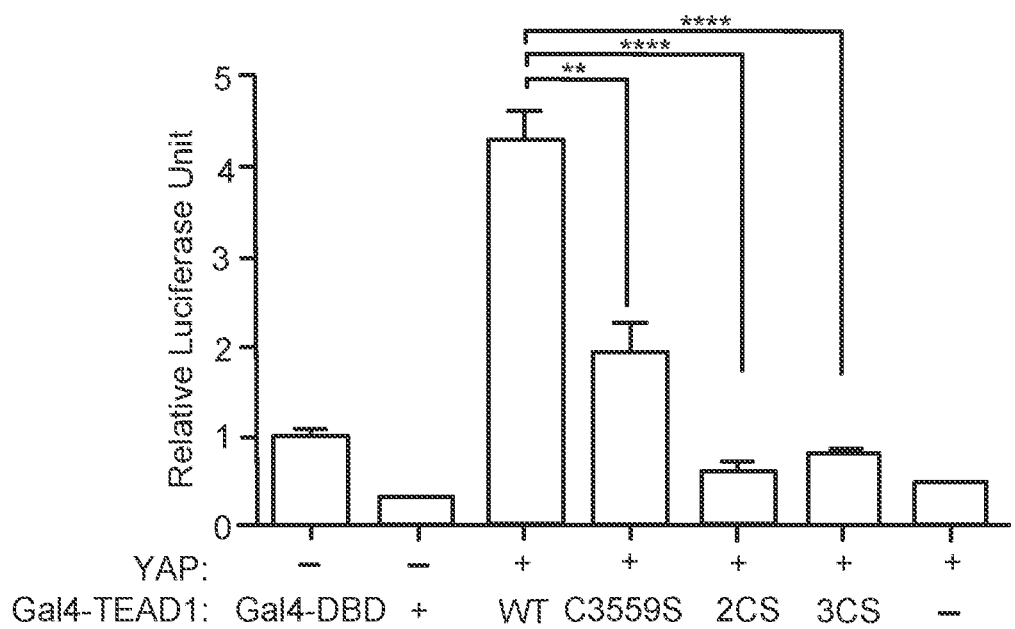
FIG. 6B is a graph showing YAP binds to and significantly activates Gal4-TEAD1 wild type (WT) in Gal4-responsive luciferase assay. The palmitoylation-deficient Gal4-TEAD1 mutants (C359S, 2CS and 3CS) significantly inhibits Gal4-responsive luciferase reporter. (Data are represented as mean±SEM, n=3. P values were determined using two-tailed t-tests. **, $p<0.0001$, , $p<0.005$).
Figure 6C:
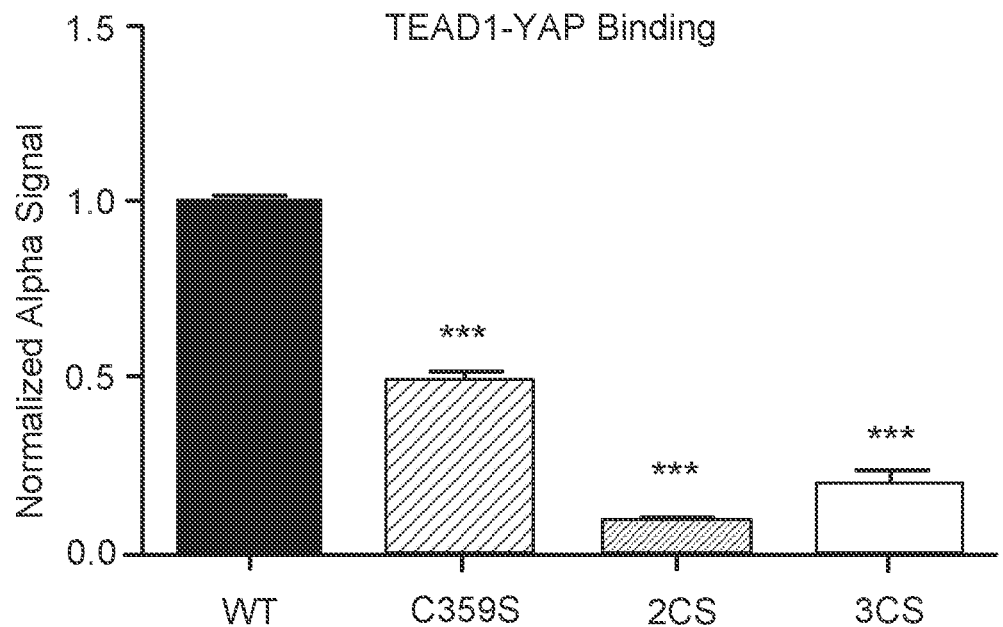
FIG. 6C is a graph showing the results of FRET-based binding assay (Alpha Screen), indicating that TEAD1 palmitoylation-deficient mutants (C359S, 2CS and 3CS) have decreased binding to YAP, comparing to TEAD1 WT. (Data are represented as mean±SEM, n=3. P values were determined using two-tailed t-tests. ***, $p<0.0005$).

In addition, the TEAD-YAP/TAZ interaction was tested using Gal4-TEAD1 or TEAD2 fusion protein, which can activate a Gal4-responsive luciferase reporter upon YAP or TAZ binding. It was found that Gal4-TEAD1/2 WT can activate the Gal4-responsive luciferase in the presence of YAP or TAZ, indicating of forming active transcription complex. However, the palmitoylation-deficient mutants (C359S, 2CS and 3CS) have significantly reduced activities (FIG. 6B), with TEAD 2CS and 3CS mutant lost most of the activities. Furthermore, a FRET-based binding assay (Alpha Screen) between TEAD1 and YAP also confirmed that TEAD mutant (C359S) had weaker association with YAP, and the palmitoylation-deficient mutants (2CS and 3CS) lost binding to YAP (FIG. 6C). Taken together, these results showed that palmitoylation of TEAD plays important roles in regulating its binding to transcription co-activators.

Figure 6D:
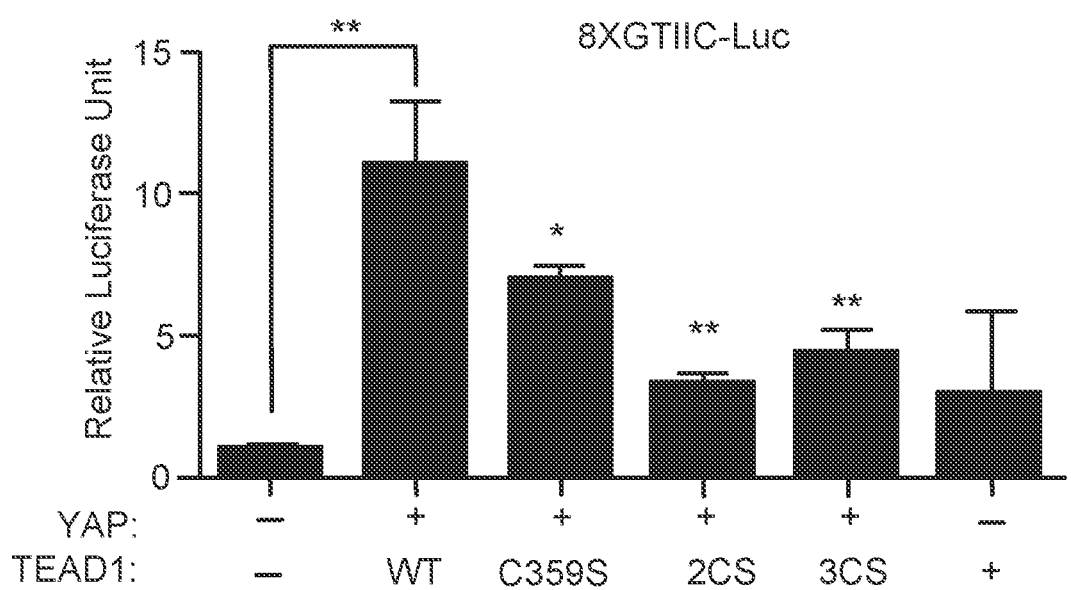
FIG. 6D is a graph showing palmitoylation-deficient mutants of TEAD1 (C359S, 2CS, and 3CS) significantly decreased TEAD transcription activity in a TEAD-binding element driven luciferase reporter assay (8XGTIIC-luciferase). (Data are represented as mean±SEM, n=3. P values were determined using two-tailed t-tests. *, $p<0.05$; **, $p<0.005$).

The functional roles of TEAD palmitoylation were also examined. It was observed that TEAD1 C359S mutant is partially defective in YAP-induced transcriptional activities. Consistently, TEAD1 2CS or 3CS mutant lost the activities in TEAD-binding element reporter (8xGTIIC-Luc) assays (FIG. 6D), suggesting that blocking TEAD palmitoylation impairs its transcriptional activity.

Figure 6E:
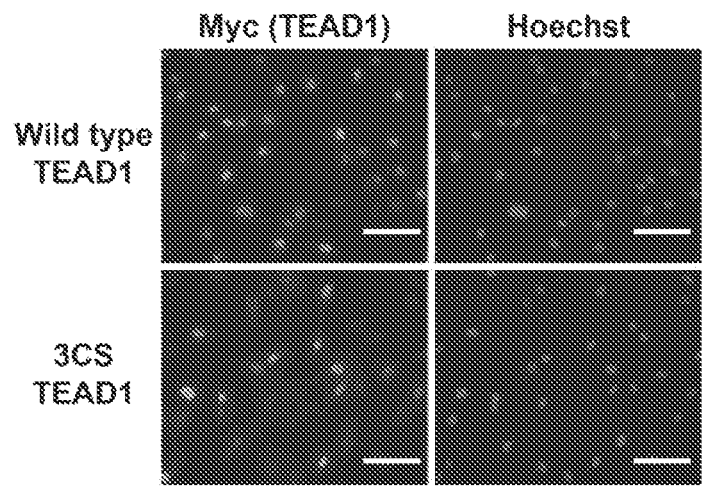
FIG. 6E contains fluorescence microscopy images showing that palmitoylation does not alter TEAD1 localization; the images show that palmitoylation-deficient TEAD1 mutant (3CS) remains localized in the nucleus in C2C12 cells (top) HeLa cells (middle), and it does not alter YAP localization (bottom). Cellular localization of endogenous YAP was visualized by immunostaining and images were captured using Nikon Digital Insight microscope. Scale bar: 100 μm.
Figure 6E:
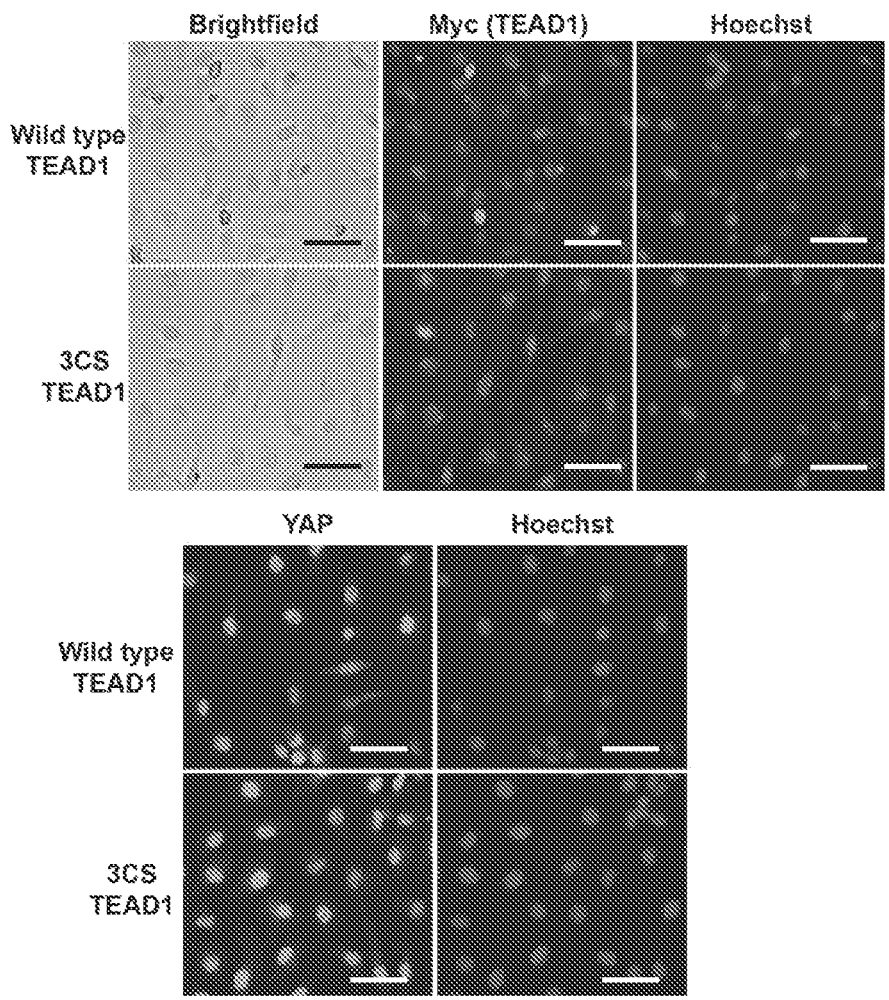

In addition, both TEAD1 WT and 3CS mutant localized similarly in the nucleus (FIG. 6E), suggesting that palmitoylation does not alter TEAD1 localization. These findings were consistent with our observations that palmitate binds to a deep pocket inside of TEAD. Unlike other palmitoylated proteins, palmitate might not serve as a membrane anchor for TEADs. Therefore, our results have uncovered new functions of protein palmitoylation in regulating transcription factor complexes.

Figure 6F:
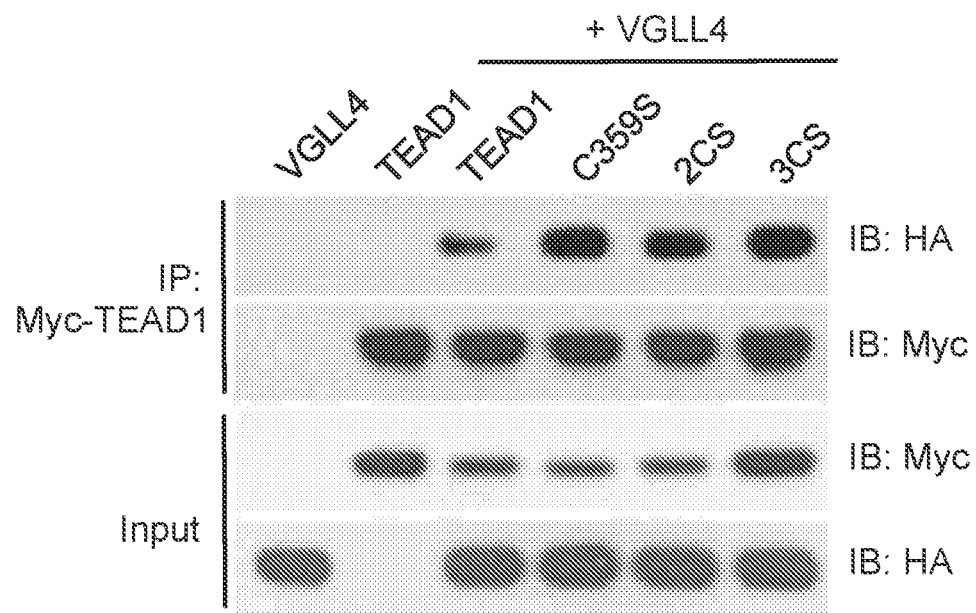
FIG. 6F is a Western blot showing palmitoylation-deficient mutants of TEAD1 (C359S, 2CS, and 3CS) retain the binding to Vgll4 tumor suppressor in co-immunoprecipitation (co-IP) experiments.
Figure 6G:
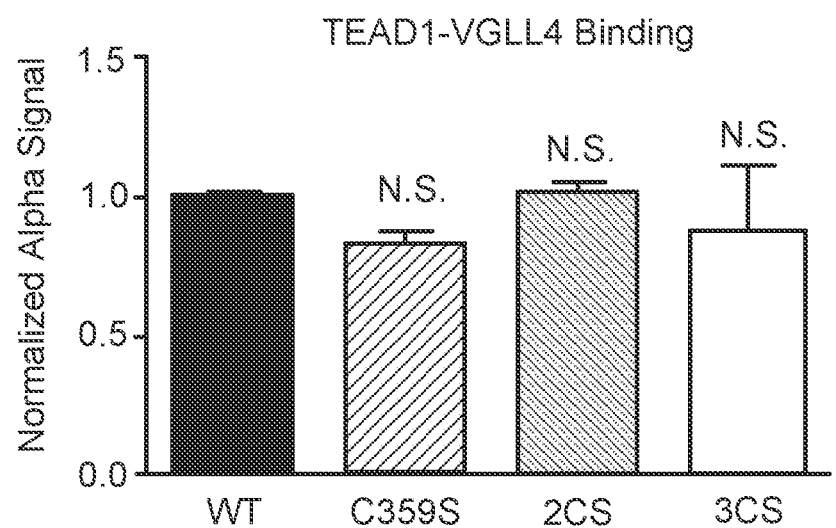
FIG. 6G is a graph showing the results of a FRET-based binding assay (Alpha Screen), indicating that TEAD1 palmitoylation-deficient mutants (C359S, 2CS and 3CS) and TEAD1 WT bind to Vgll4 similarly. (Data are represented as mean±SEM, n=3. P values were determined using two-tailed t-tests. N.S., not significant) FIG. 7A are representative images of myosin heavy chain (MHC) immunostaining of C2C12 cells. Scale bar: 100 μm.

Moreover, it was found that TEAD2 2CS/3CS mutants were properly folded. It has been reported that TEADs can bind to Vgll4, a tumor suppressor that competes with YAP for TEAD binding, and consequently inhibits YAP oncogenic activity. In the co-IP assay, it was found that TEAD1 WT and the palmitoylation-deficient mutants (C359S, 2CS or 3CS mutants) were able to bind to Vgll4 (FIG. 6F). Consistently, in the FRET-based (Alpha Screen) binding assay, TEAD1 WT, C359S, 2CS and 3CS mutants all bind to Vgll4 similarly (FIG. 6G).

Taken together, these results show that palmitoylation is required for TEAD1-YAP binding, but is dispensable for TEAD1-Vgll4 binding. In addition, as TEAD1 C359S, 2CS and 3CS mutants are still capable of binding to Vgll4, the loss of YAP binding are not due to misfolding.

In crystal structures, palmitate does not directly interact with YAP. Therefore, palmitate allosterically regulates YAP binding. It has been shown that YAP binds to TEAD through three interfaces. Mutations of TEAD residues at interface III greatly inhibited YAP, not Vgll4 binding, suggesting interface III is more critical for YAP binding. These results suggest that palmitoylation allosterically changes the conformation of TEAD at or near interface III, thus regulating YAP binding, but not Vgll4 binding. The results described herein and a recent report (Noland et al., *Structure*, 2016, 24, 1-8) suggest that binding of palmitate rigidifies the structure of TEAD, which may affect the local side chain dynamics around the binding interface III, which was required for YAP binding. Further structural and protein side-chain dynamic studies using NMR spectrometry will provide more details about how palmitate allosterically regulates TEAD protein dynamics. Fatty acylation has been shown before to allosterically regulate protein functions. For example, N-terminal myristoyl modification of c-Abl binds to the kinase domain and induces conformational changes of the protein, resulted in autoinhibition of c-Abl kinase activity.

F. Palmitoylation Regulates TEAD Physiological Functions

The physiological roles of TEAD palmitoylation were also investigated. It has been shown that TAZ promotes terminal differentiation and myotube fusion of skeletal muscle cells through TEAD1 and TEAD4. A TEAD4 mutant (TEAD4-DBD), which lacks YAP/TAZ binding domain, functioned as a dominant negative mutant and inhibited C2C12 myoblast differentiation and myotube fusion. Therefore, TEAD-TAZ association is critical for myogenesis. As TEAD palmitoylation is required for TAZ binding, we speculate that loss of TEAD palmitoylation might impair myogenesis.

Figure 7A:
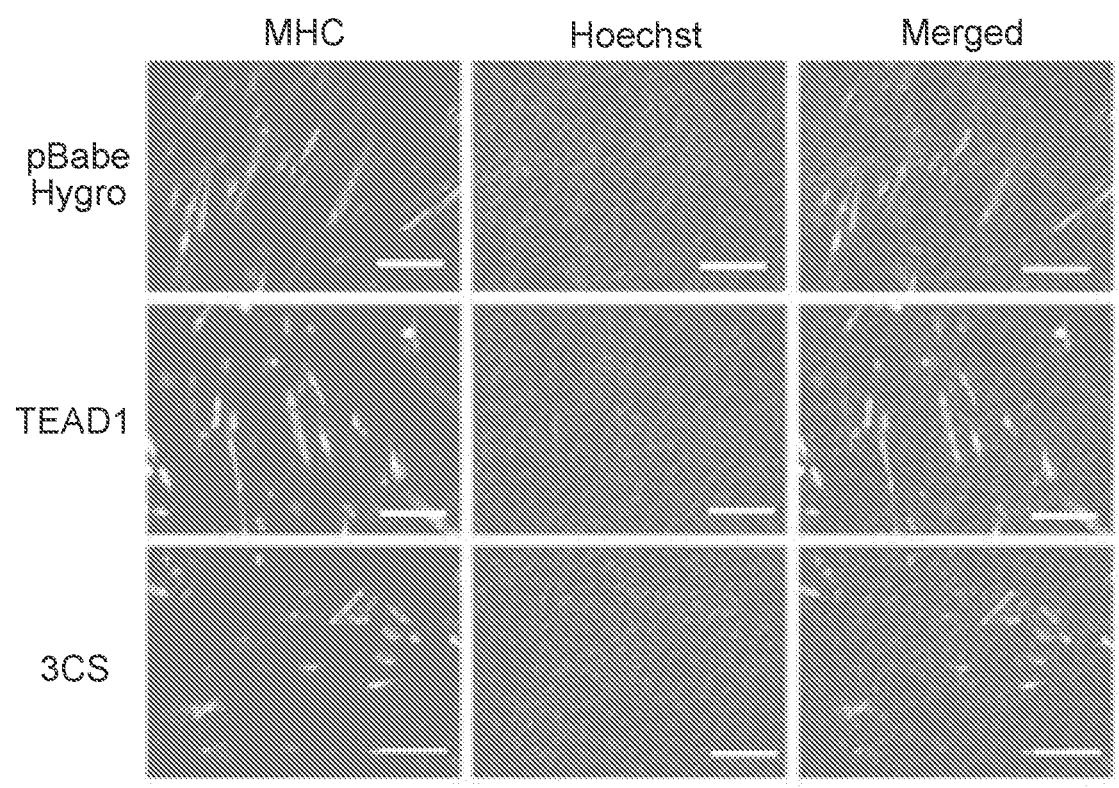
FIG. 7B and FIG. 7C are graphs showing that TEAD1 3CS mutant significantly inhibited myogenic differentiation and myotube fusion. Differentiation and fusion indices were calculated by averaging the data obtained from five different fields. (Data are represented as mean±SEM, n=5. P values were determined using two-tailed t-tests. **, $p<0.005$).
FIG. 7D and FIG. 7E are graphs showing TEAD 3CS mutant blocked the expression of myogenic markers Mef2C, and TEAD target genes (CTGF and Cyr61) in C2C12 cell. (Data are represented as mean±SEM, n=3. P values were determined using two-tailed t-tests. **, $p<0.01$)
Figure 7B:
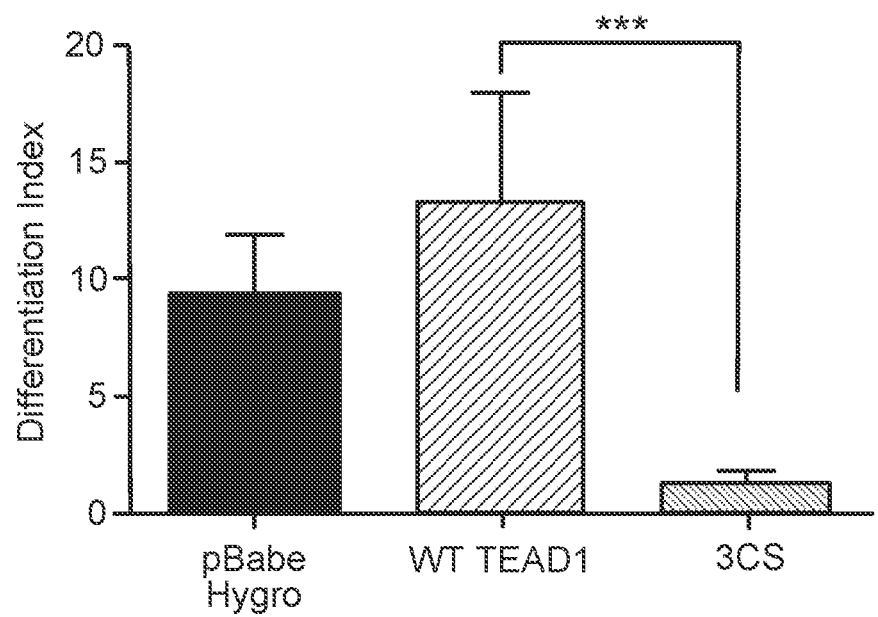
Figure 7C:
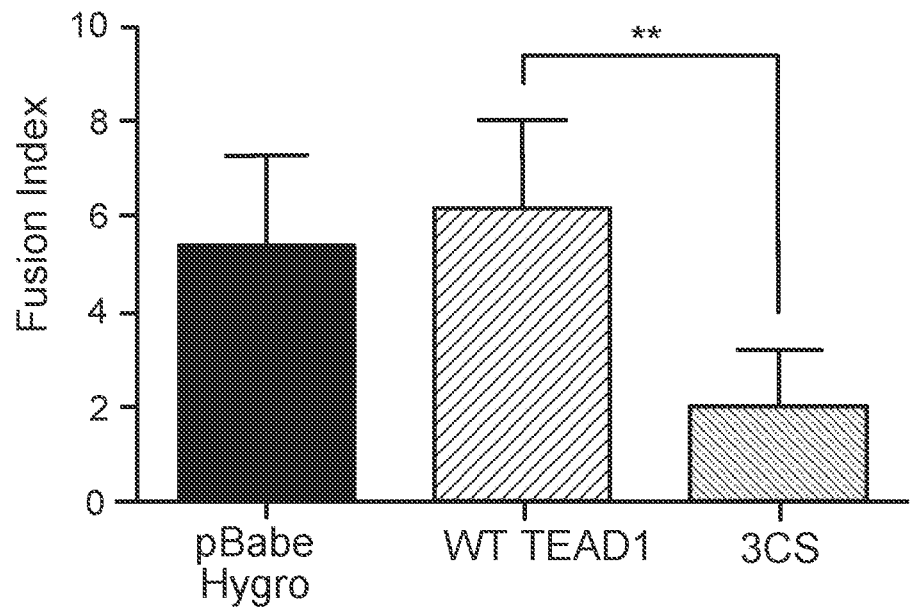

To test this hypothesis, C2C12 myoblast cells were stably transfected with TEAD1 WT or 3CS mutant, and then induce to differentiate. C2C12 cells stably expressing vector control (pBabe Hygro), TEAD1 WT or TEAD1 3CS mutant, were induced to differentiate for 3 days. Cell nuclei were stained with DAPI. Muscle differentiation was evaluated by immunostaining of myosin heavy chain (MHC). TEAD1 3CS strongly inhibited muscle differentiation and myotube fusion, compared to vector control and TEAD1 WT (FIG. 7A). C2C12 cells expressing TEAD1 3CS showed significantly lower differentiation index and fusion index (FIGS. 7B and 7C).

Figure 7D:
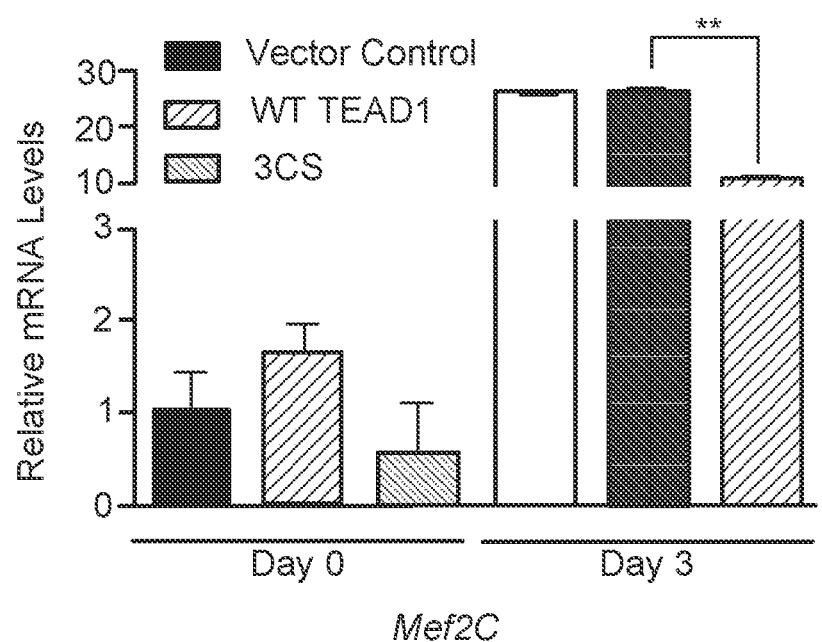
Figure 7E:
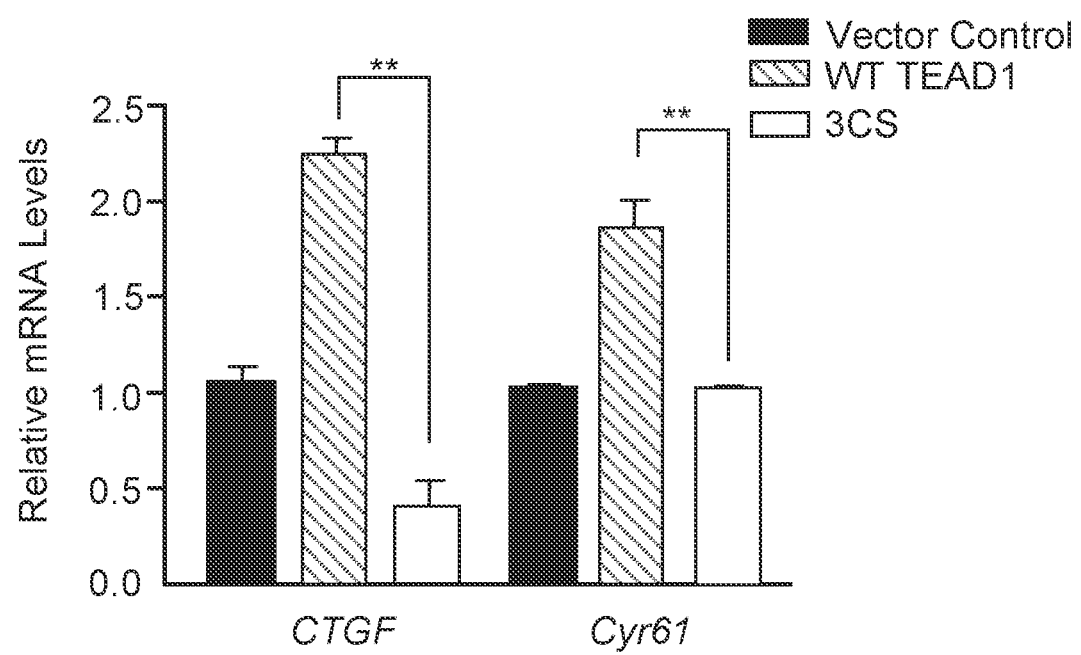

In addition, expression of TEAD1 3CS mutant blocked muscle differentiation gene (Mef2C, MyoG1, Myh4), as well as TEAD-specific target genes (CTGF and Cyr61) expression by qRT-PCR (FIGS. 7D and 7E). In the experiments whose results are shown in FIGS. 7D and 7E, RNA samples of C2C12 stably expressed vector control, wild type and 3CS mutant of TEAD1 were collected and cDNA of each were synthesized, and mRNA levels of each gene were determined by qRT-PCR using SYBR Green and normalized to GAPDH. Taken together, the results suggested that palmitoylation is required for TEADs' normal physiological functions in muscle differentiation in vitro.

Figure 8A:
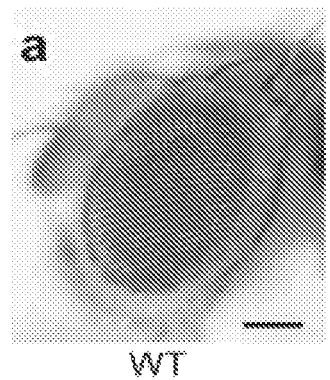
FIG. 8A is an image of compound eyes from the genotype GMR-gal4/+. Scale bar: 150 μm.
Figure 8D:
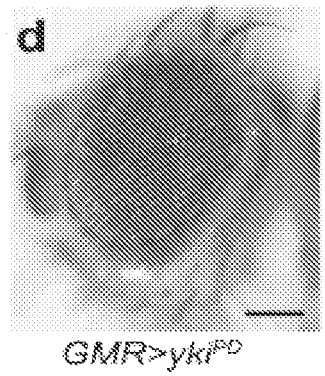
FIG. 8D is an image of compound eyes from the genotype GMR-gal4, UAS-yki$^{PD}$. Scale bar: 150 μm.
Figure 8B:
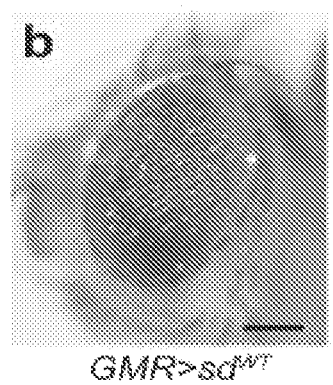
FIG. 8B is an image of compound eyes from the genotype GMR-gal4/UAS-sd$^{WT}$. Scale bar: 150 μm.
Figure 8E:
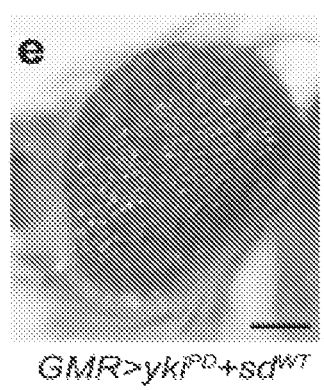
FIG. 8E is an image of compound eyes from the genotype GMR-gal4, UAS-yki$^{PD}$/UAS-sd$^{WT}$. Scale bar: 150 μm.
Figure 8C:
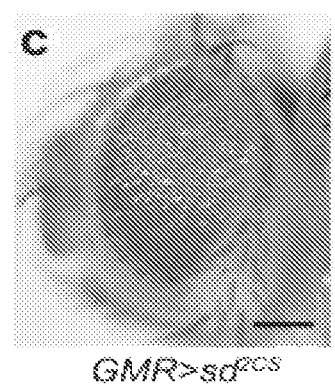
FIG. 8C is an image of compound eyes from the genotype GMR-gal4/UAS-sd$^{2CS}$. Scale bar: 150 μm.
Figure 8F:
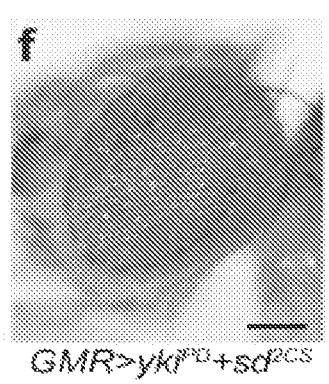
FIG. 8F is an image of compound eyes from the genotype GMR-gal4, UAS-yki$^{PD}$/UAS-sd$^{2CS}$. Scale bar: 150 μm.
Figure 8G:
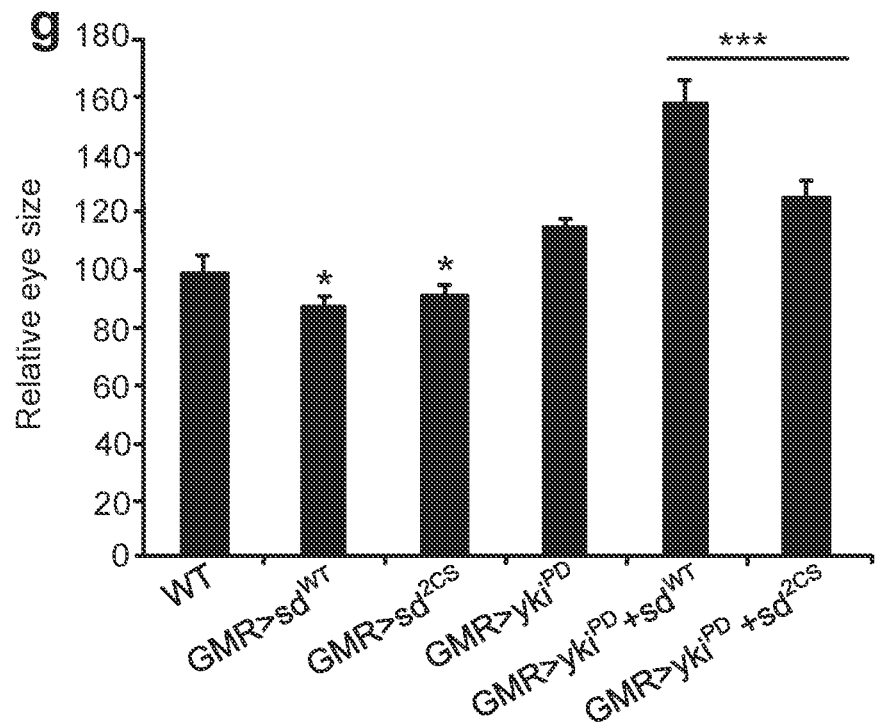
FIG. 8G is a graph showing the relative sizes of the fly eyes are quantified in indicated genotypes. Sd WT and Sd 2CS flies are compared to the wild type, with statistically smaller eyes. (Data are represented as mean±SEM, n=10 for each genotype. P values were determined using two-tailed t-tests. *, $p<0.05$; ***, $p<0.001$)

To further corroborate the functional significance of TEAD palmitoylation, the ability of wild type *Drosophila* Scalloped (Sd) or palmitoylation-deficient (2CS) mutant (both constructs targeted to the same genetic locus to avoid positional effect of transgene insertion) to cooperate with Yorkie (Yki) in promoting tissue overgrowth were compared using a sensitive in vivo assay. Differential splicing of Yki results in two isoforms containing two WW domains (Yki-PG and Yki-PF, Flybase) or a single WW domain (Yki-PD, Flybase). Unlike Yki-PG whose overexpression resulted in eye overgrowth[5], overexpression of Yki-PD alone resulted in only slightly bigger eye sizes, but such changes are not statistically significant (FIG. 8A to 8D). Nevertheless, co-expression of Yki-PD and Sd (WT) caused a significant enlargement of eye size (FIG. 8E), providing a very sensitive assay for Sd-Yki complex in driving tissue overgrowth. Interestingly, this overgrowth phenotype was significantly compromised when Yki-PD was co-expressed with the palmitoylation-deficient Sd (2CS) mutant (FIG. 8F). The overgrowth phenotype (enlarged eyes with rough surface) caused by co-expression of Yki-PD and Sd (WT) (FIG. 8E) is compromised when Yki-PD is co-expressed with the palmitoylation-deficient Sd (2CS) mutant (FIG. 8F). The images were taken with the same magnification. The size of the eye in wild type control flies is marked in blue dashed line, and the same area is shown in all images to The eye sizes in all the flies were quantified and the results were subjected to statistical analysis (FIG. 8G).

Figure 8H:
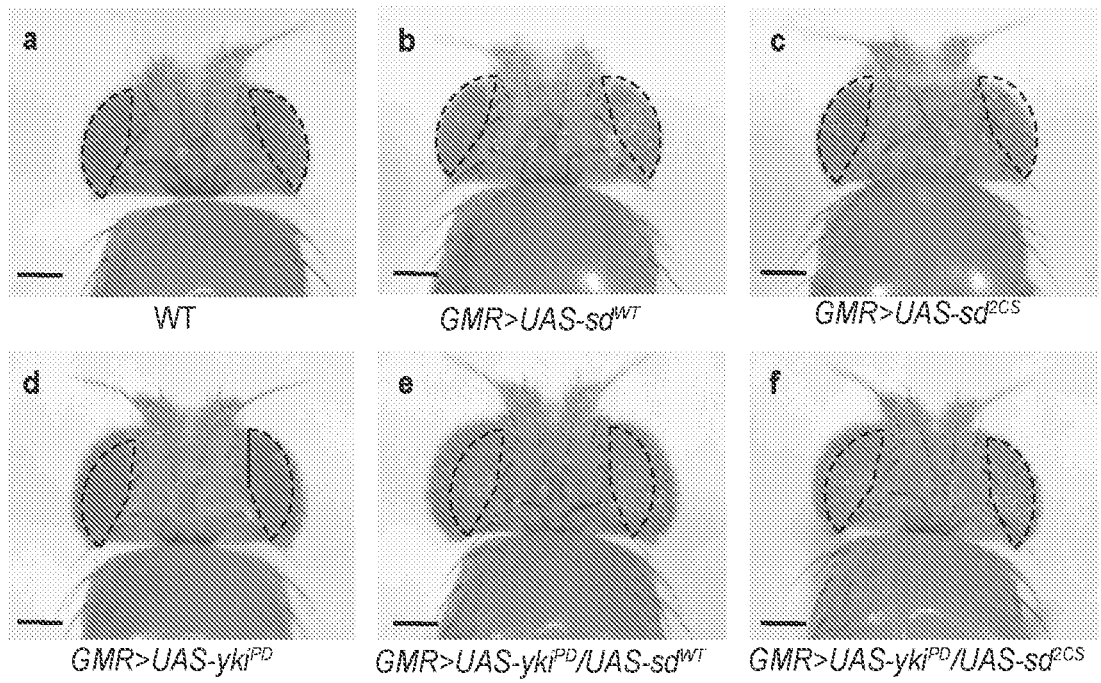
FIG. 8H is a collection of photographs Top view of compound eyes from the following genotypes: (a) GMR-gal4/+, (b) GMR-gal4/UAS-sd$^{WT}$, (c) GMR-gal4/UAS-sd$^{2CS}$, (d) GMR-gal4, UAS-yki$^{PD}$, (e) GMR-gal4, UAS-yki$^{PD}$/UAS-sd$^{WT}$, (f) GMR-gal4, UAS-yki$^{PD}$/UAS-sd$^{2CS}$. The images were taken with the same magnification. The size of the eye in wild type control flies is marked in blue dashed line, and the same area is shown in all images to facilitate comparison. Scale bar: 150 μm.

In addition, the top views of the flies (FIG. 8H) showed the size of eyes from a different angle.

Both the Sd WT and 2CS mutant have statistically significant reduction of eye growth compared to WT flies (FIGS. 8B, 8C, and 8G), which is consistent with the default repressor functions of Sd. The difference between Sd WT and 2CS mutant is not statistically significant. Therefore, it is likely that loss of palmitoylation in Sd (2CS) does not affect its default repressor functions. This result is consistent with the findings in human cells, where TEAD1 (2CS) can still bind to Vgll4.

Figure 8I:
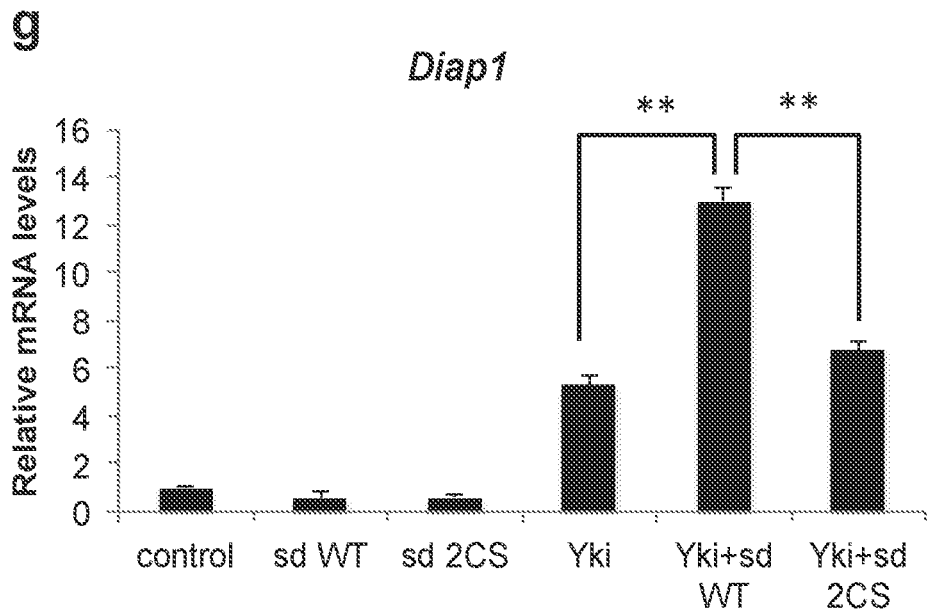
FIGS. 8I and 8J are plots of the Yki-Sd target genes expression (Diap1 and Expanded) in fly S2 cells transfected with indicated constructs by qRT-PCR. (Data are represented as mean±, SEM, n=3. P values were determined using two-tailed t-tests. **, $P<0.01$)
Figure 8J:
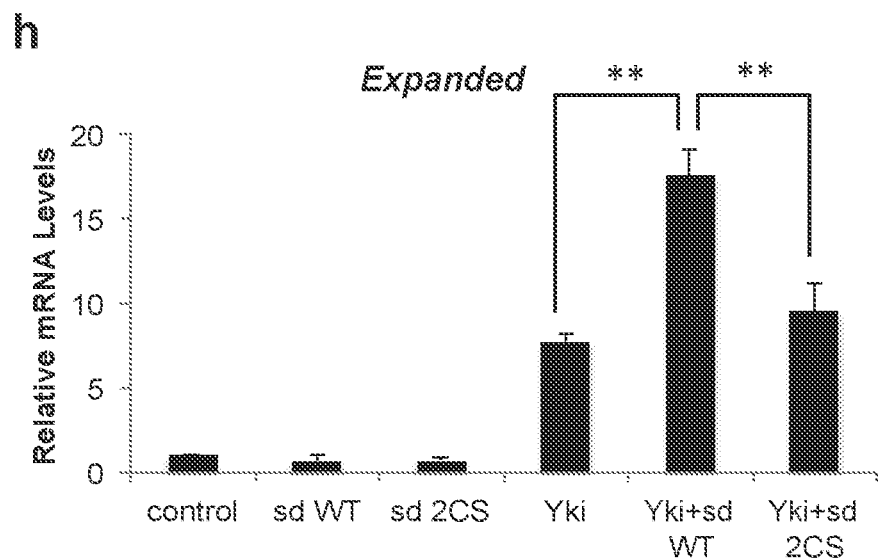

To better evaluate the effects on target genes, qRT-PCR analysis was performed of Diap1 and Expanded in fly S2 cells with the expression of the 2CS mutant or WT Scalloped. Consistently, expression of Yki and WT Scalloped induced the expression of both genes, while expression of Yki and Scalloped 2CS mutant significantly compromised the target gene expression in fly cells (FIGS. 8I and 8J).

Taken together, the results suggest that palmitoylation is required for the physiological function of the TEAD transcription factors.

G. Identification of Small Molecule Inhibitors of TEAD Autopalmitoylation

A small molecule library (50K compounds) was screened using a HEK293A stable cell line expressing the TEAD-binding element luciferase reporter (8xGTII-Luc) and YAP. Compounds were screened at 5 μM concentration using the reporter assay as the primary screen, and then the compounds were evaluated in TEAD-independent reporter systems or toxicity control (Celltiter Glo, Topflash-Luc and p53-Luc) as counter assays. Compounds that had >50% of inhibition in TEAD-reporter, but <20% of inhibition in control assays were selected as primary hits. To identify inhibitors of TEAD palmitoylation, the primary hits were tested in the TEAD2 autopalmitoylation assay in vitro, and resulted in identification of compounds that inhibited TEAD2 autopalmitoylation. Therefore, the mode-of-action of these compounds might be through inhibition of TEADs palmitoylation.

Figure 9:
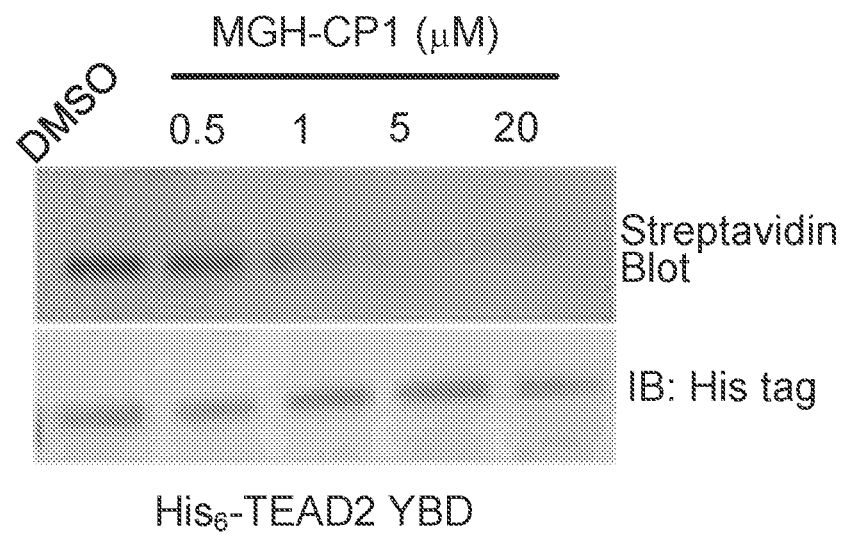
FIG. 9 is a Streptavidin plot showing that compound 4 (MGH-CP1) dose-dependently inhibits TEAD2 YBD autopalmitoylation in vitro. Recombinant TEAD2 YBD was incubated with 1 μM of alkyne palmitoyl-CoA for 1 h in the presence of control (DMSO) or increasing 0.5-20 μM of compound 4. Palmitoylation of TEAD2 was detected by streptavidin blot.

One of the compounds identified was compound 4 ("MGH-CP1"), which inhibited TEAD2 autopalmitoylation in vitro, and TEAD1 palmitoylation in cells in a concentration-dependent manner (FIG. 9).

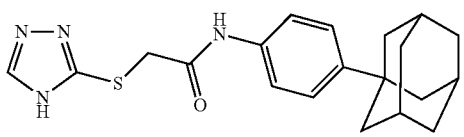

4

Figure 10:
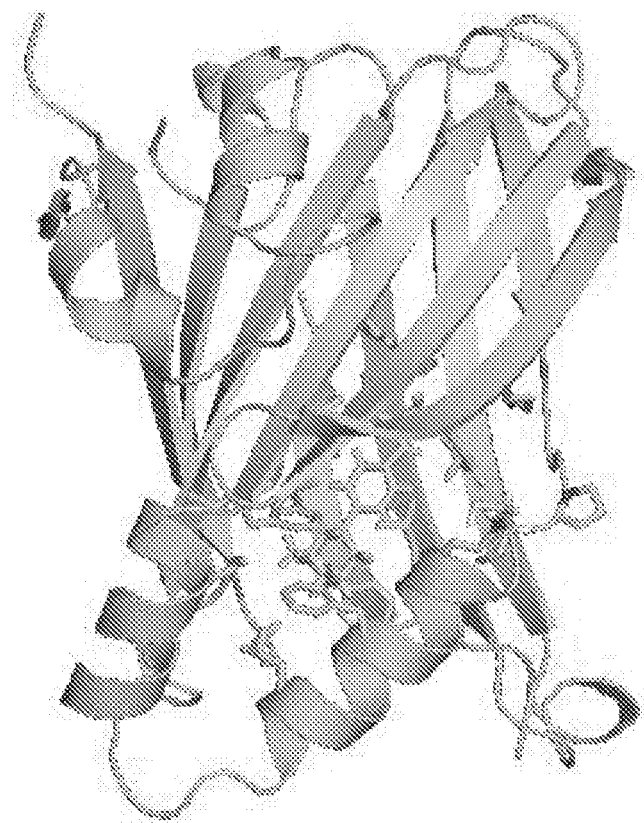
FIG. 10 is a ribbon diagram of the crystal structure of compound 4-bound TEAD2, with compound 4 shown as gray sticks.
Figure 11:
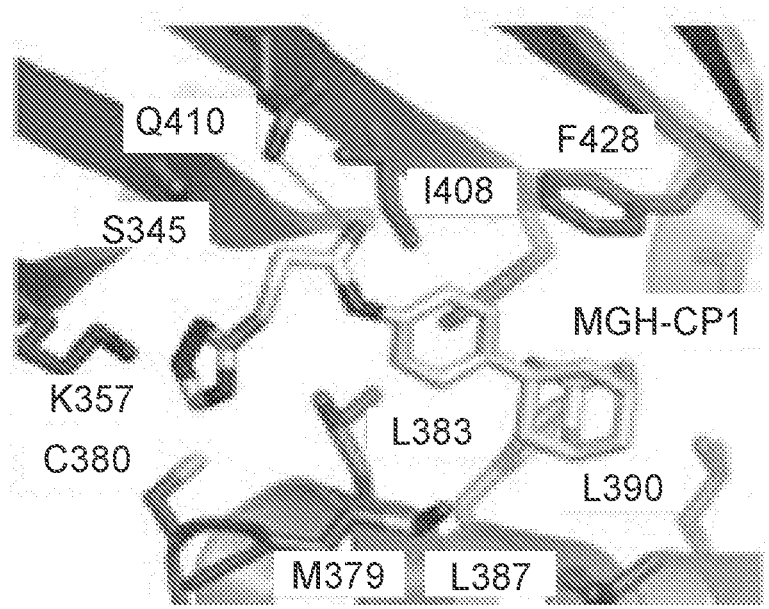
FIG. 11 is a diagram showing a close-up view of the compound 4 binding site of TEAD2. A hydrogen bond is shown between the carbonyl oxygen of compound 4 and the $NH_2$ group of Q410 which indicated with a dashed line.

To confirm the mode-of-action of compound 4 and to elucidate the detailed molecular interactions between MGH-CP1 and TEADs, the co-crystal structure of compound 4 bound to TEAD2 at 2.0 Å resolution was determined (Table 1). In the inhibitor-bound TEAD2 structure, compound 4 binds to the same hydrophobic pocket previously occupied by palmitate, consistent with our observation that compound 4 inhibits TEAD palmitoylation (FIG. 10). The adamatane moiety of compound 4 binds inside the pocket, making hydrophobic interactions with residues in the pocket, and the triazole ring is adjacent to the opening of the hydrophobic pocket (FIG. 11). In addition, the carbonyl oxygen forms a hydrogen bond with the side chain of Q410 (FIG. 11).

Figure 12:
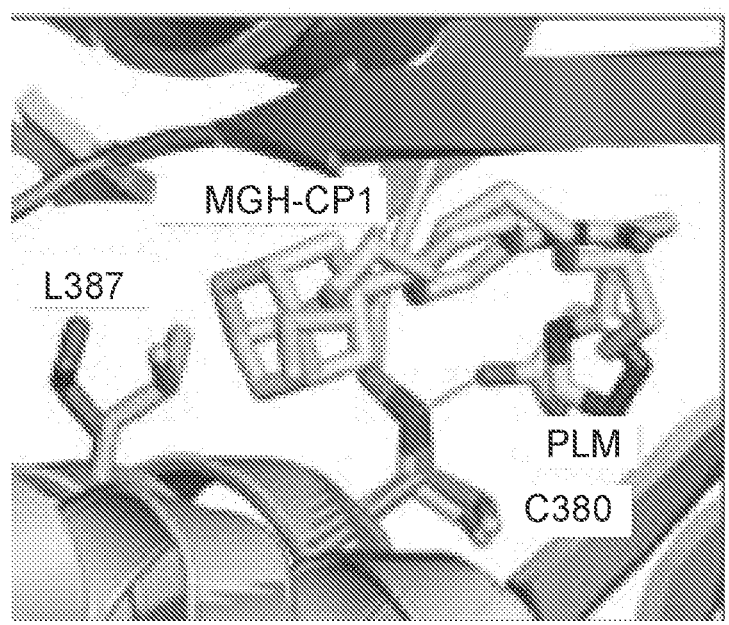
FIG. 12 is a diagram showing superimposed structures of the TEAD2-PLM complex and the TEAD2-compound 4 complex. The bound ligands, PLM and compound 4 (MGH-CP1) are shown as sticks. A potential hydrogen bond between PLM and the backbone amide of C380 is indicated with a dashed line.

The structure of compound 4 bound to TEAD2 was compared with that of palmitate-bound TEAD4, it was found that compound 4 adopted a conformation similar to palmitate when bound to TEAD2 (FIG. 12). These results confirm that compound 4 is a small molecule inhibitor of TEAD, which displaced fatty acid from the conserved hydrophobic pocket. Furthermore, the inhibitor-bound structure could provide structural guidance for further optimizations of TEAD inhibitors.

Figure 13:
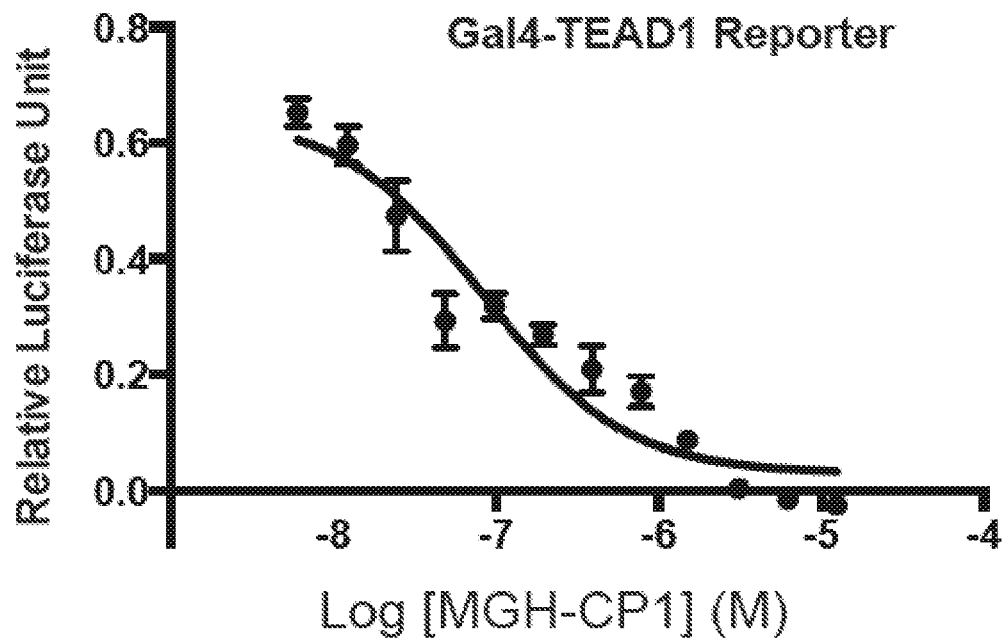
FIG. 13 is a plot of inhibition of TEAD1-YAP interaction in a Gal4-TEAD1/YAP reported assay by compound 4. Compound 4 inhibits TEAD1-YAP interaction in Gal4-TEAD1/YAP reporter assay with an $IC_{50}$ of 83 nM. (Data are represented as mean+/−SEM, n=3.)
Figure 14:
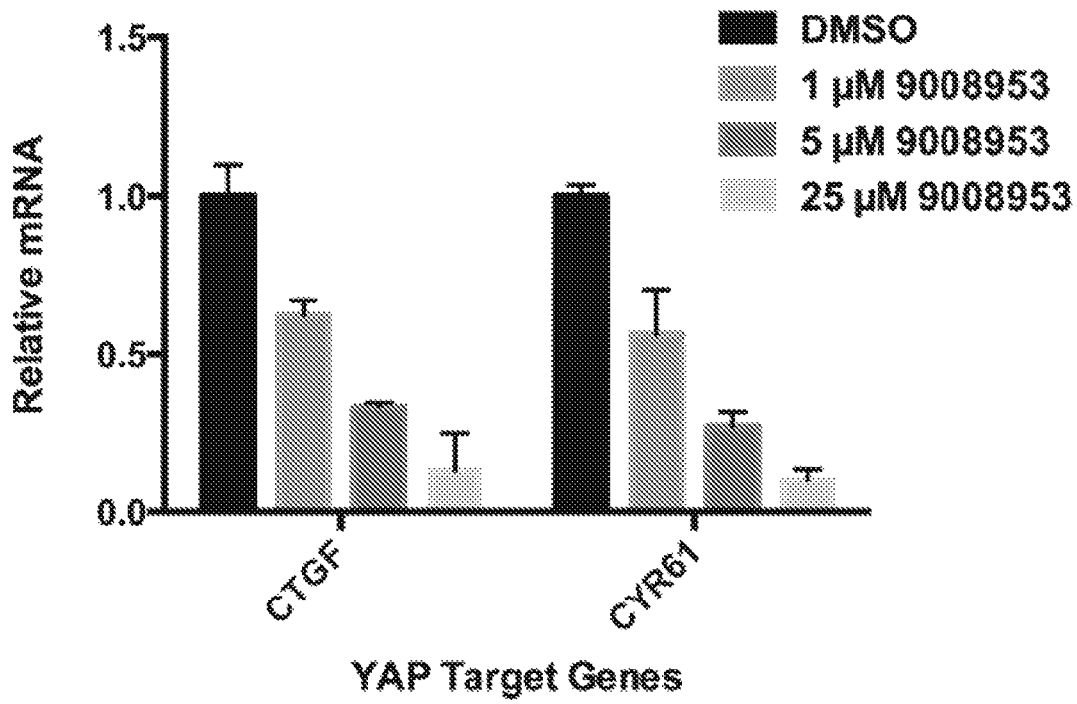
FIG. 14 is graph showing compound 4 inhibits YAP-TEAD target gene expression in cancer cell line (HeLa).
Figure 15:
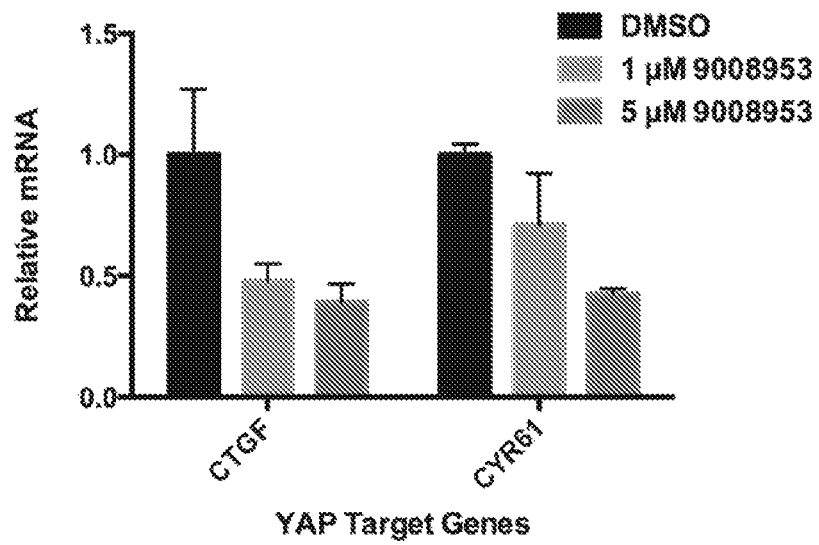
FIG. 15 is a graph showing compound 4 inhibits TEAD-YAP target gene expression in liver cancer cell line (JHH7).
Figure 16:
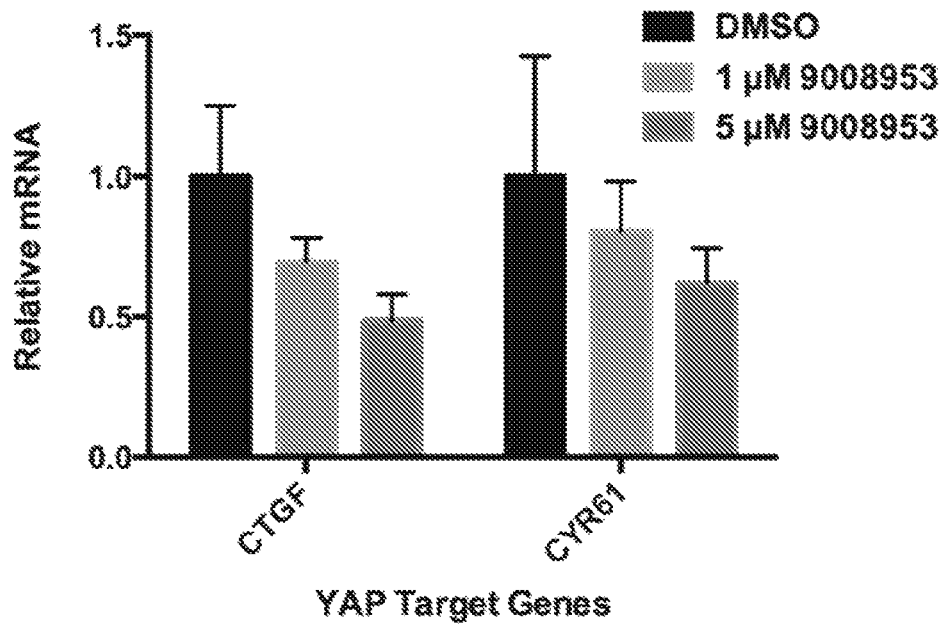
FIG. 16 is a graph showing compound 4 inhibits TEAD-YAP target genes in human liver cancer cell line (HuH7).
Figure 17:
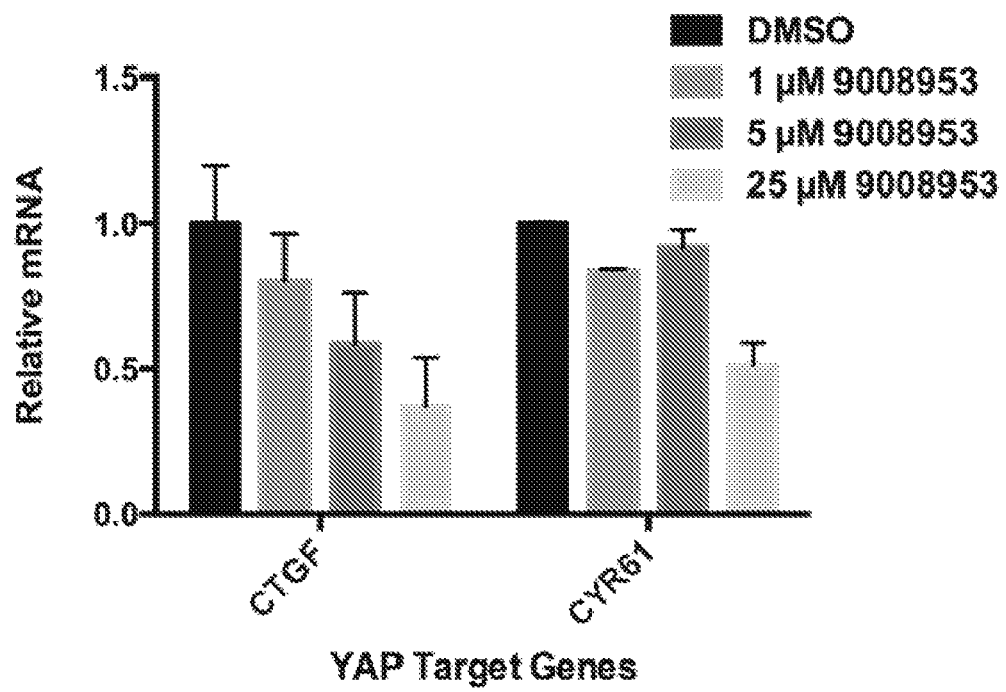
FIG. 17 is a graph showing compound 4 inhibits YAP transformed MCF10A cell target gene expression.

To test whether compound 4 can inhibit TEAD's functions, inhibition of the TEAD YAP interaction using the Gal4-TEAD1 reporter system was evaluated. It was found that MGH-CP1 dose-dependently inhibited TEAD-YAP interaction, with an $IC_{50}$ of 83 nM in this assay (FIG. 13).

In cancer cell lines, loss-of-function of the upstream tumor suppressors in Hippo pathways often lead to hyperactivation of TEAD-YAP transcriptional complex. Compound 4 was tested in cell lines with hyperactivated YAP, including HeLa (LKB1 mutation), and hepatocellular carcinoma cells JHH7 and HuH7 (Mst1/2 loss of functions and YAP amplification)(Fitamant et al., 2015; Mohseni et al., 2014; Nguyen et al., 2012; Zhou et al., 2009). It was found that compound 4 could inhibit TEAD-YAP target genes expression (CTGF and Cyr61)—in all these cells (FIGS. 14-17), suggesting that inhibition of TEAD palmitoylation by compound 4 could functionally inhibit TEAD-YAP transcriptional activities.

Figure 18:
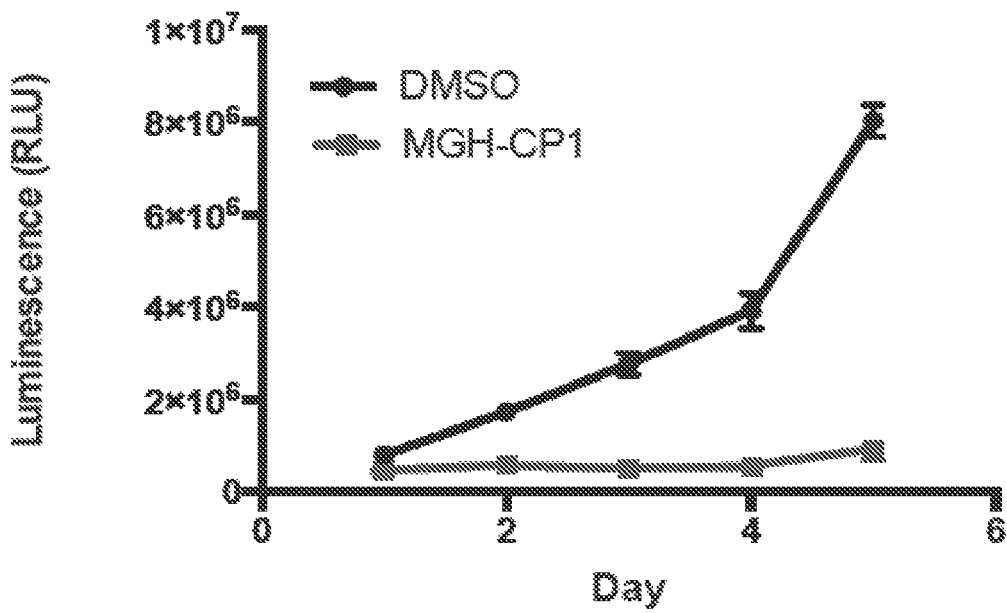
FIG. 18 is a graph showing compound 4 (10 µM) inhibits YAP-dependent cancer cell proliferation in JHH 500 cells/well.
Figure 19:
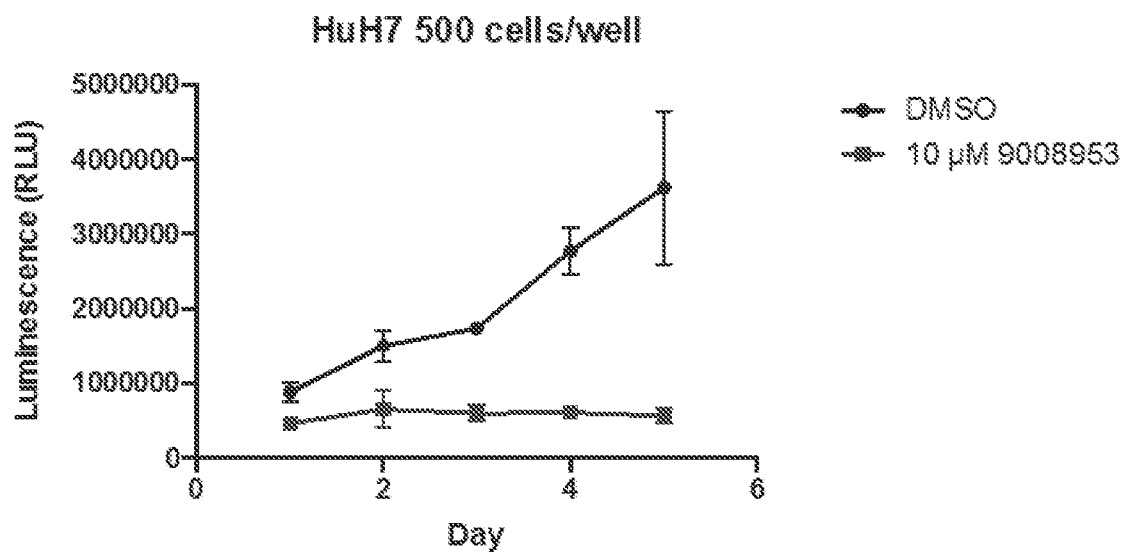
FIG. 19 is a graph showing compound 4 ("9008953") inhibits YAP-dependent cancer cell proliferation in HuH7 500 cells/well.
Figure 20:
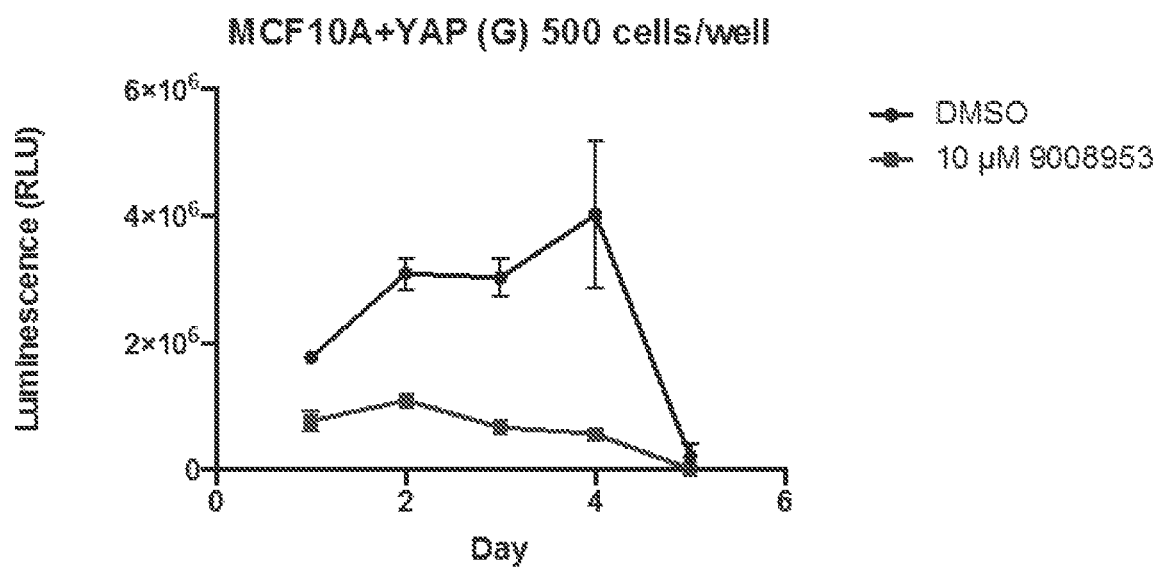
FIG. 20 is a graph showing that compound 4 inhibits YAP-dependent cancer cell proliferation in MCF10A+YAP (G) 500 cells/well.

In addition, the cells were treated with compound 4 (10 μM) or DMSO controls to evaluate cell viability. It was found that compound 4 can effectively block cell proliferation of YAP-dependent cancer cell lines in vitro (FIGS. 18-20).

Figure 21:
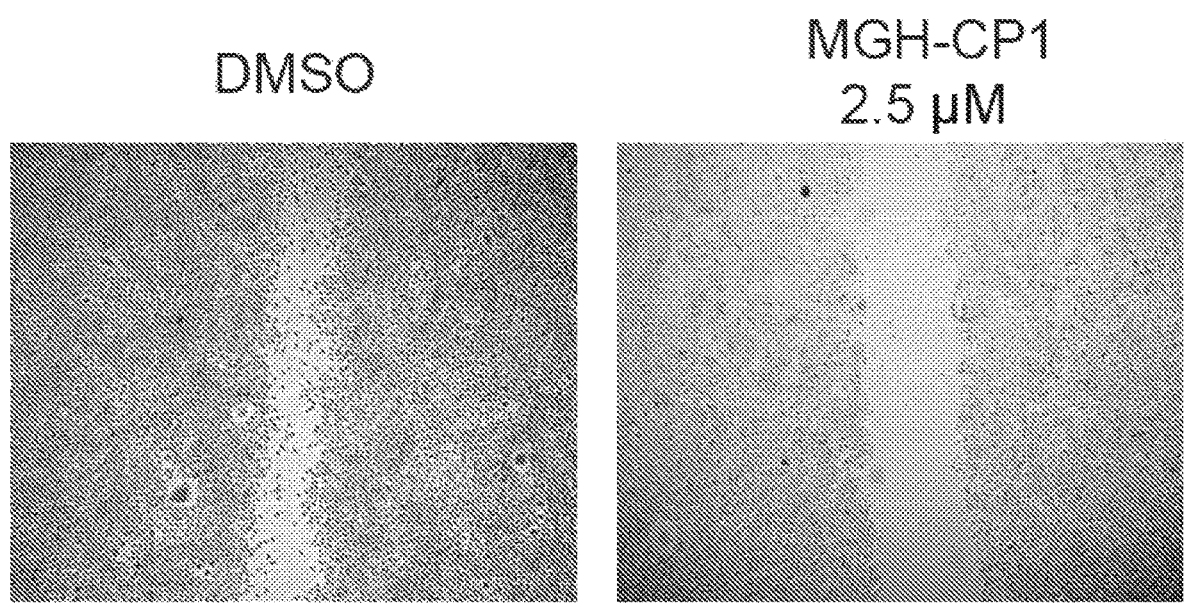
FIG. 21 is a pair of images showing cell migration of Lats1/2 double knock-out MEF cells, showing that compound 4 inhibits cell migration.

It has been reported that YAP/TAZ could promote cell invasion and migration (Chan et al., 2008). To test whether compound 4 can functionally inhibit YAP/TAZ-dependent cell invasion, Lats1/2 double knock-out (Lats1/2 DKO) MEF cells were used in a scratch assay (Kim et al., 2013). Cells were treated with DMSO control or 2.5 μM of MGH-CP1, and the activities of the compound in blocking the closure of the scratched area was measured. Cells treated with DMSO control migrated fast and closed the gap within 16-24 hs. In contrast, cells treated with compound 4 did not migrate (FIG. 21). Taken together, we have demonstrated that small molecules could indeed bind to the conserved lipid-binding pocket in TEADs, and inhibit TEAD-YAP activities. It is noted that MGH-CP1 does not have optimal properties for in vivo testing. Therefore, further optimization of MGH-CP1 is needed to develop potent and specific inhibitors as chemical tools or "lead" compounds for drug discovery. Nevertheless, we have demonstrated that TEADs are indeed "druggable".

In addition to compound 4, compounds 5-53 were investigated as additional TEAD inhibitors—assay data are provided in Example 15:

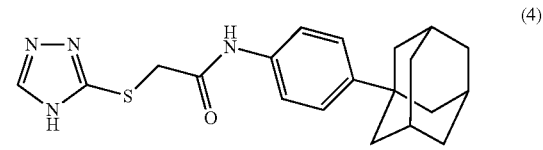

(4)

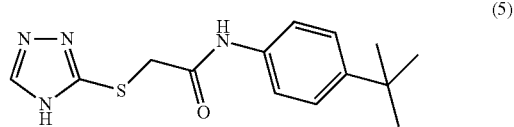

(5)

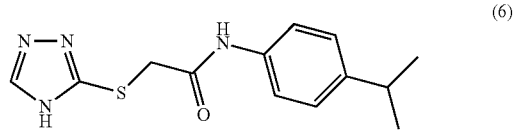

(6)

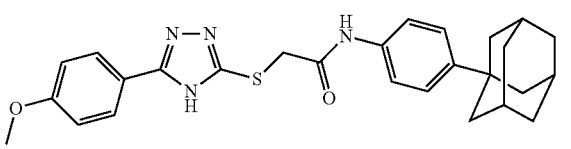

(7)

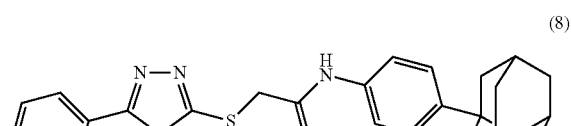

(8)

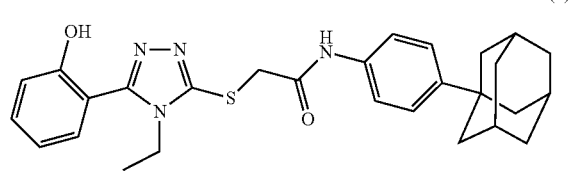

(9)

(10)
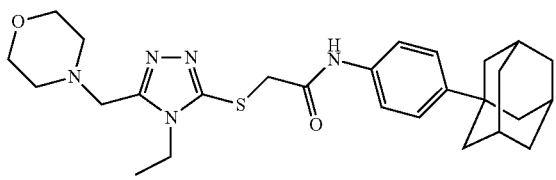
(11)
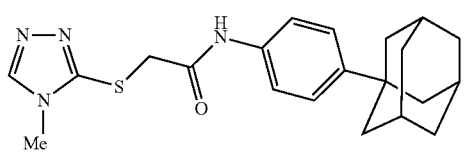
(12)
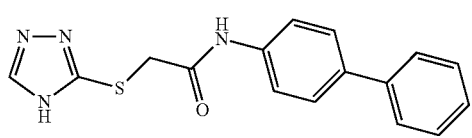
(13)
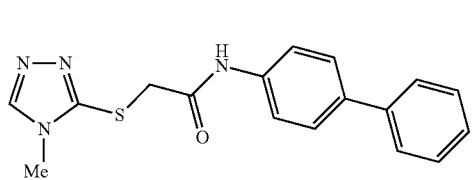
(14)
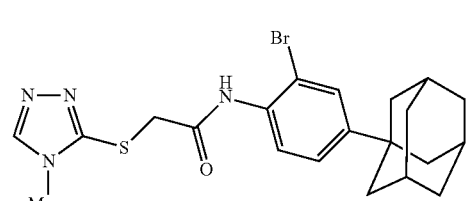
(15)
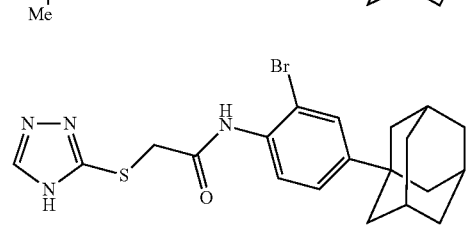
(16)
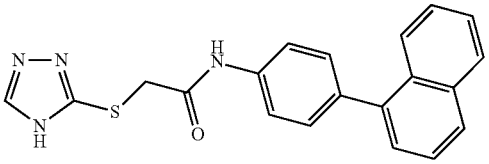
(17)
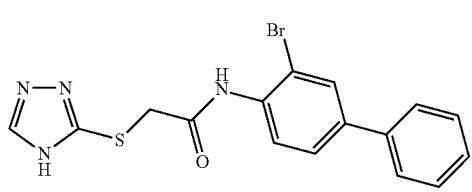
(18)
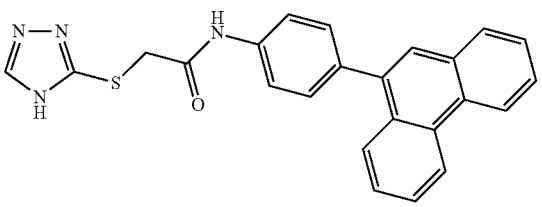
(19)
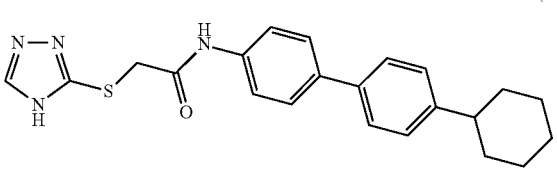
(20)
(21)
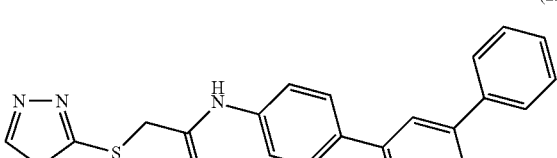
(22)
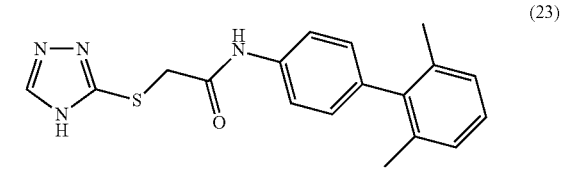
(23)
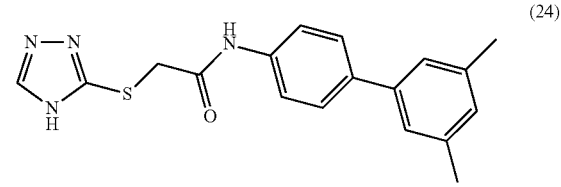
(24)

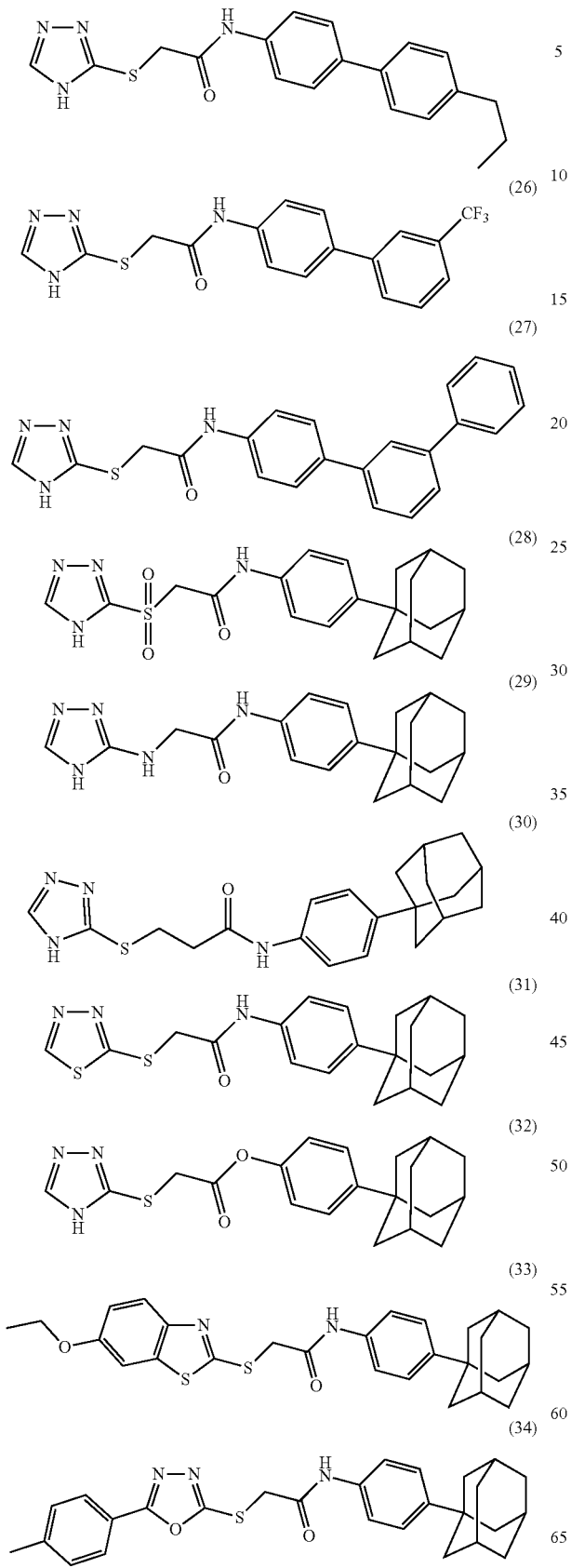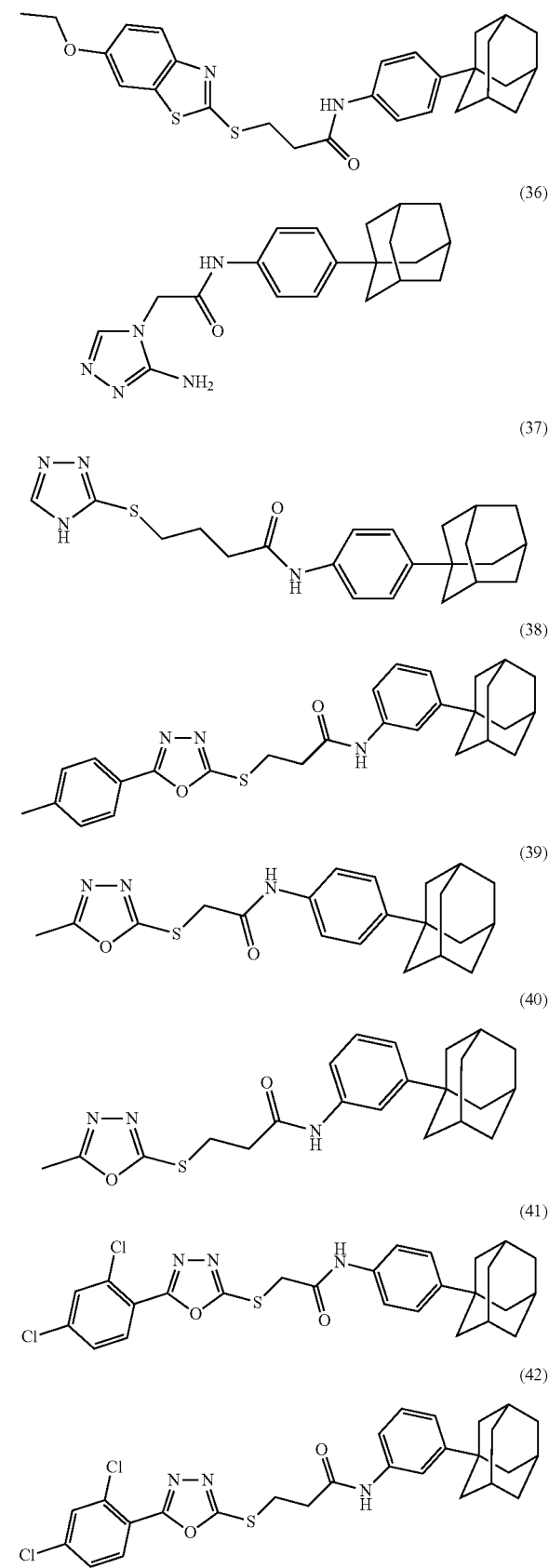

(43) 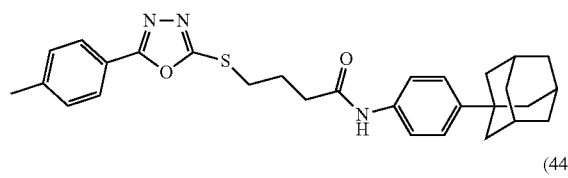

(44) 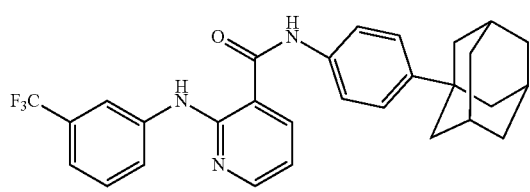

(45) 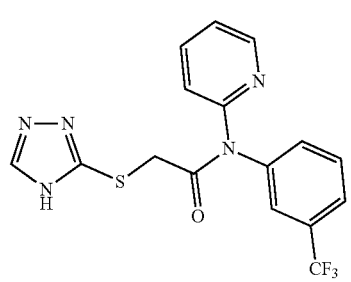

(46) 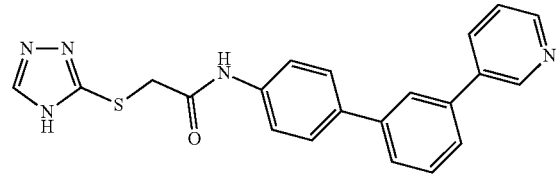

(47) 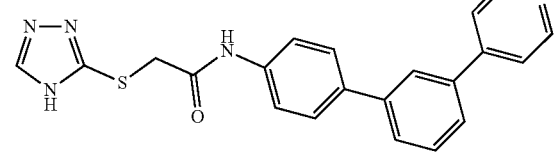

(48) 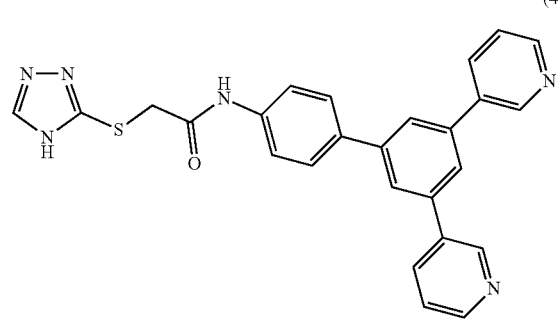

(49) 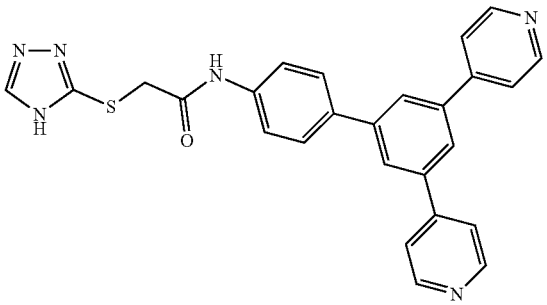

(50) 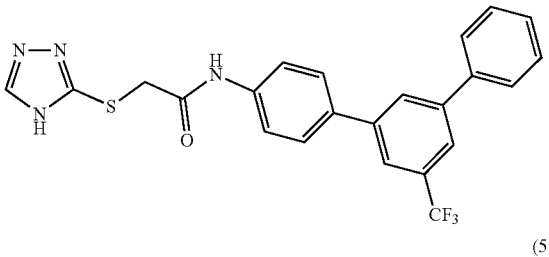

(51) 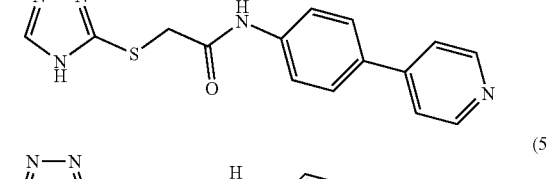

(52) 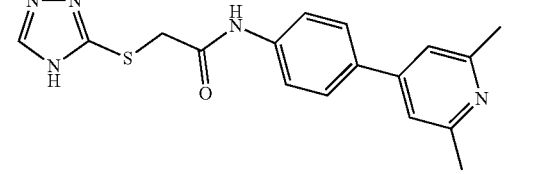

(53) 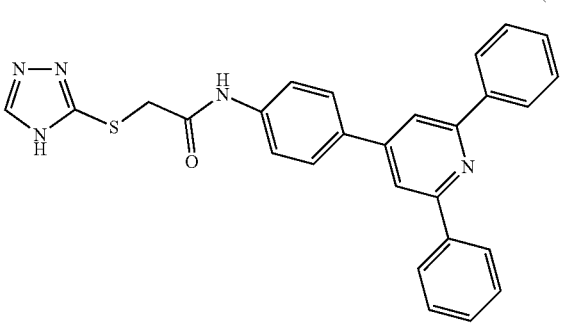

H. Discussion

In summary, chemical approaches have revealed that TEADs are specifically autopalmitoylated at evolutionarily conserved cysteine residues. Autopalmitoylation has been considered as a non-specific reaction of surface cysteine residues with high concentration of palmitoyl-CoA. The present studies, together with the studies of yeast Bet3 protein, have shown that autopalmitoylation could happen under physiological conditions, with specific cysteine residues being modified. As there are only 23 DHHC-PATs, it is unlikely that they are responsible for all the palmitoylation activities in cells (more than 1000 protein substrates are S-palmitoylated). Therefore, it is possible that many S-palmitoylated proteins are modified through PAT-independent processes, and autopalmitoylation could be an important regulation for protein functions. The present studies have demonstrated for the first time to systematically identify autopalmitoylated proteins using chemical tools.

Palmitoylation has been commonly linked to membrane attachment and protein trafficking. The present results have shown that palmitate binds to a hydrophobic pocket in the core of the protein, and does not regulate protein membrane binding. It has been noted that in the crystal structures of yeast Bet3 protein, the covalently attached palmitate also binds into a hydrophobic pocket in the protein. Palmitoylation of Bet3 stabilizes the protein and is involved in regulating Bet3 degradation and co-factor binding. Therefore, in addition to acting as a membrane-binding moiety, palmitoylation of proteins indeed has other important functions.

It has been observed that TEAD1 C359 is the major and stable site of modification, which is located at the opening of the lipid-binding pocket. Since palmitate-free TEAD2 could not be purified and crystallized, it is likely that binding of palmitate stabilized the conformation of TEAD, allowing the protein to be crystallized. Nevertheless, TEAD proteins may exist as palmitoylated and non-palmitoylated species in cells. It has been observed that TEAD2 C380S remains autopalmitoylated, but not the C348/380S mutant, consistent with the observation that TEAD 2CS/3CS mutant has more significant loss of activity than C380S. Although the lipid modification of C348 was not observed in the crystal structures, which are only snapshots of the most stable conformations of the protein, both C348 and C380 should be involved in palmitoylation. It is possible that C348-palmitoylated TEAD2 has a different conformation, allowing palmitate to bind to the conserved deep pocket. In addition, another hydrophobic pocket near the surface is close to C348 in TEAD2 structure, which could accommodate the binding of hydrophobic ligands, such as bromofenamic acid (BFA). Further studies may reveal more detailed structures of C348-palmitoylated TEAD2.

The levels of TEAD autopalmitoylation are highly relevant to the palmitoyl-CoA concentrations in cells. The cellular palmitoyl-CoA pool might be an upstream regulator of TEAD's activities and Hippo pathway. Fatty acid synthase (FASN) is the key enzyme that synthesizes palmitoyl-CoA from acetyl-CoA and malonyl-CoA. FASN has been proposed as a potential oncogene, which is upregulated in breast cancers and its expression is associated with poor prognosis. High level of FASN might lead to high intracellular palmitoyl-CoA, thus promoting TEAD-YAP mediated oncogenic processes. Further studies may reveal that TEAD-YAP activities are responsible for tumorigenesis in FASN-overexpressed cancer cells.

The present studies have also shown that it is possible to develop potent and selective small molecule inhibitors to disrupt TEAD-YAP interaction, as the interaction interface is shallow and spans over a large area on the surface. The palmitate-binding pocket of TEADs is deep and hydrophobic, and can provide a site for inhibitor binding. The pocket is accessible by small molecules allowing discovery of drug candidates that inhibit TEAD autopalmitoylation.

II. Compounds

The present disclosure provides, inter alia, a compound of Formula (I):

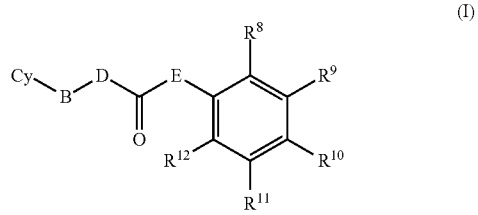

or a pharmaceutically acceptable salt thereof, wherein:
Cy is a group of Formula (Cy-A) or (Cy-B):

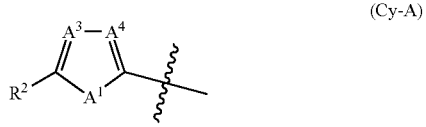

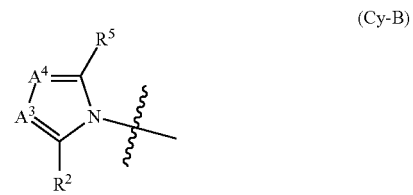

or Cy is Cy-C, wherein Cy-C is phenyl optionally substituted by zero or 1 substituents selected from $C_{6-10}$ aryl, $C_{3-10}$ cycloalkyl, 5-10 membered heteroaryl and 4-10 membered heterocycloalkyl, and 0, 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$, wherein said $C_{6-10}$ aryl, $C_{3-10}$ cycloalkyl, 5-10 membered heteroaryl or 4-10 membered heterocycloalkyl substituent of Cy-C is optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

$A^1$ is $NR^1$, O or S;

$R^1$ is H or $C_{1-6}$ alkyl;

$R^2$ is H, $C_{1-6}$ alkyl, $C_{2-6}$ alkenyl, $C_{2-6}$ alkynyl, halogen, $C_{1-6}$ haloalkyl, $C_{6-10}$ aryl, $C_{3-10}$ cycloalkyl, 5-10 membered heteroaryl, 4-10 membered heterocycloalkyl, ($C_{6-10}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl, (4-10 membered heterocycloalkyl)$C_{1-3}$ alkylenyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$, wherein each of said $C_{1-6}$ alkyl, $C_{6-10}$ aryl, $C_{3-10}$ cycloalkyl, 5-10 membered heteroaryl or 4-10 membered heterocycloalkyl, ($C_{6-10}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl or (4-10 membered heterocycloalkyl)$C_{1-3}$ alkylenyl forming $R^2$ is optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, C(=O)$R^{b1}$, C(=O)$NR^{c1}R^{d1}$, C(=O)$OR^{a1}$, OC(=O)$R^{b1}$, OC(=O)$NR^{c1}R^{d1}$, $NR^{c1}R^{d1}$, $NR^{c1}$C(=O)$R^{b1}$, $NR^{c1}$C(=O)$NR^{c1}R^{d1}$, $NR^{c1}$C(=O)$OR^{a1}$, C(=$NR^{e1}$)$NR^{c1}R^{d1}$, $NR^{c1}$C(=$NR^{e1}$)$NR^{c1}R^{d1}$, S(=O)$R^{b1}$, S(=O)$NR^{c1}R^{d1}$, S(=O)$_2R^{b1}$, $NR^{c1}$S(=O)$_2R^{b1}$ and S(=O)$_2NR^{c1}R^{d1}$;

$A^3$ is N or $CR^3$;

$R^3$ is selected from H, $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, C(=O)$R^{b1}$, C(=O)$NR^{c1}R^{d1}$, C(=O)$OR^{a1}$, OC(=O)$R^{b1}$, OC(=O)$NR^{c1}R^{d1}$, $NR^{c1}R^{d1}$, $NR^{c1}$C(=O)$R^{b1}$, $NR^{c1}$C(=O)$NR^{c1}R^{d1}$, $NR^{c1}$C(=O)$OR^{a1}$, C(=$NR^{e1}$)$NR^{c1}R^{d1}$, $NR^{c1}$C(=$NR^{e1}$)$NR^{c1}R^{d1}$, S(=O)$R^{b1}$, S(=O)$NR^{c1}R^{d1}$, S(=O)$_2R^{b1}$, $NR^{c1}$S(=O)$_2R^{b1}$ and S(=O)$_2NR^{c1}R^{d1}$; or $R^2$ and $R^3$, together with the atoms to which $R^2$ and $R^3$ are attached, together form a fused benzo ring that is optionally substituted with 1, 2, 3 or 4 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, C(=O)$R^{b1}$, C(=O)$NR^{c1}R^{d1}$, C(=O)$OR^{a1}$, OC(=O)$R^{b1}$, OC(=O)$NR^{c1}R^{d1}$, $NR^{c1}R^{d1}$, $NR^{c1}$C(=O)$R^{b1}$, $NR^{c1}$C(=O)$NR^{c1}R^{d1}$, $NR^{c1}$C(=O)$OR^{a1}$, C(=$NR^{e1}$)$NR^{c1}R^{d1}$, $NR^{c1}$C(=$NR^{e1}$)$NR^{c1}R^{d1}$, S(=O)$R^{b1}$, S(=O)$NR^{c1}R^{d1}$, S(=O)$_2R^{b1}$, $NR^{c1}$S(=O)$_2R^{b1}$ and S(=O)$_2NR^{c1}R^{d1}$;

$A^4$ is N or $CR^4$;

$R^4$ is selected from H, $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, C(=O)$R^{b1}$, C(=O)$NR^{c1}R^{d1}$, C(=O)$OR^{a1}$, OC(=O)$R^{b1}$, OC(=O)$NR^{c1}R^{d1}$, $NR^{c1}R^{d1}$, $NR^{c1}$C(=O)$R^{b1}$, $NR^{c1}$C(=O)$NR^{c1}R^{d1}$, $NR^{c1}$C(=O)$OR^{a1}$, C(=$NR^{e1}$)$NR^{c1}R^{d1}$, $NR^{c1}$C(=$NR^{e1}$)$NR^{c1}R^{d1}$, S(=O)$R^{b1}$, S(=O)$NR^{c1}R^{d1}$, S(=O)$_2R^{b1}$, $NR^{c1}$S(=O)$_2R^{b1}$ and S(=O)$_2NR^{c1}R^{d1}$;

$R^5$ is selected from H, $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, C(=O)$R^{b1}$, C(=O)$NR^{c1}R^{d1}$, C(=O)$OR^{a1}$, OC(=O)$R^{b1}$, OC(=O)$NR^{c1}R^{d1}$, $NR^{c1}R^{d1}$, $NR^{c1}$C(=O)$R^{b1}$, $NR^{c1}$C(=O)$NR^{c1}R^{d1}$, $NR^{c1}$C(=O)$OR^{a1}$, C(=$NR^{e1}$)$NR^{c1}R^{d1}$, $NR^{c1}$C(=$NR^{e1}$)$NR^{c1}R^{d1}$, S(=O)$R^{b1}$, S(=O)$NR^{c1}R^{d1}$, S(=O)$_2R^{b1}$, $NR^{c1}$S(=O)$_2R^{b1}$ and S(=O)$_2NR^{c1}R^{d1}$;

B is absent (a bond), or is selected from $NR^6$, O, S, S(O) and S(O)$_2$;

$R^6$ is H or $C_{1-6}$ alkyl;

D is $C_{1-4}$ alkylene optionally substituted by 1, 2, 3, 4 or 5 substituents selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, C(=O)$R^{b1}$, C(=O)$NR^{c1}R^{d1}$, C(=O)$OR^{a1}$, OC(=O)$R^{b1}$, OC(=O)$NR^{c1}R^{d1}$, $NR^{c1}R^{d1}$, $NR^{c1}$C(=O)$R^{b1}$, $NR^{c1}$C(=O)$NR^{c1}R^{d1}$, $NR^{c1}$C(=O)$OR^{a1}$, C(=$NR^{e1}$)$NR^{c1}R^{d1}$, $NR^{c1}$C(=$NR^{e1}$)$NR^{c1}R^{d1}$, S(=O)$R^{b1}$, S(=O)$NR^{c1}R^{d1}$, S(=O)$_2R^{b1}$, $NR^{c1}$S(=O)$_2R^{b1}$ and S(=O)$_2NR^{c1}R^{d1}$;

or D is phenylene or 5-6-membered heteroarylene, wherein said phenylene or 5-6 membered heteroarylene forming D is optionally substituted by 1, 2, 3 or 4 substituents independently selected from $C_{1-6}$ alkyl, $C_{2-6}$ alkenyl, $C_{2-6}$ alkynyl, halogen, $C_{1-6}$ haloalkyl, $OR^{a1}$, $SR^{a1}$, C(=O)$R^{b1}$, C(=O)$NR^{c1}R^{d1}$, C(=O)$OR^{a1}$, OC(=O)$R^{b1}$, OC(=O)$NR^{c1}R^{d1}$, $NR^{c1}R^{d1}$, $NR^{c1}$C(=O)$R^{b1}$, $NR^{c1}$C(=O)$NR^{c1}R^{d1}$, $NR^{c1}$C(=O)$OR^{a1}$, C(=$NR^{e1}$)$NR^{c1}R^{d1}$, $NR^{c1}$C(=$NR^{e1}$)$NR^{c1}R^{d1}$, S(=O)$R^{b1}$, S(=O)$NR^{c1}R^{d1}$, S(=O)$_2R^{b1}$, $NR^{c1}$S(=O)$_2R^{b1}$ and S(=O)$_2NR^{c1}R^{d1}$;

E is $NR^7$ or O;

$R^7$ is H or $C_{1-6}$ alkyl;

or $R^7$ is phenyl or 5-6-membered heteroaryl, wherein said phenyl or 5-6 membered heteroaryl forming $R^7$ is optionally substituted by 1, 2, 3 or 4 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, C(=O)$R^{b1}$, C(=O)$NR^{c1}R^{d1}$, C(=O)$OR^{a1}$, OC(=O)$R^{b1}$, OC(=O)$NR^{c1}R^{d1}$, $NR^{c1}R^{d1}$, $NR^{c1}$C(=O)$R^{b1}$, $NR^{c1}$C(=O)$NR^{c1}R^{d1}$, $NR^{c1}$C(=O)$OR^{a1}$, C(=$NR^{e1}$)$NR^{c1}R^{d1}$, $NR^{c1}$C(=$NR^{e1}$)$NR^{c1}R^{d1}$, S(=O)$R^{b1}$, S(=O)$NR^{c1}R^{d1}$, S(=O)$_2R^{b1}$, $NR^{c1}$S(=O)$_2R^{b1}$ and S(=O)$_2NR^{c1}R^{d1}$;

$R^8$, $R^9$, $R^{10}$, $R^{11}$ and $R^{12}$ are each independently selected from H, $C_{1-6}$ alkyl, $Cy^1$, $C_{2-6}$ alkenyl, $C_{2-6}$ alkynyl, halogen, $C_{1-6}$ haloalkyl, CN, $OR^{a1}$, $SR^{a1}$, C(=O)$R^{b1}$, C(=O)$NR^{c1}R^{d1}$, C(=O)$OR^{a1}$, OC(=O)$R^{b1}$, OC(=O)$NR^{c1}R^{d1}$, $NR^{c1}R^{d1}$, $NR^{c1}$C(=O)$R^{b1}$, $NR^{c1}$C(=O)$NR^{c1}R^{d1}$, $NR^{c1}$C(=O)$OR^{a1}$, C(=$NR^{e1}$)$NR^{c1}R^{d1}$, $NR^{c1}$C(=$NR^{e1}$)$NR^{c1}R^{d1}$, S(=O)$R^{b1}$, S(=O)$NR^{c1}R^{d1}$, S(=O)$_2R^{b1}$, $NR^{c1}$S(=O)$_2R^{b1}$ and S(=O)$_2NR^{c1}R^{d1}$;

provided that no more than two of $R^8$, $R^9$, $R^{10}$, $R^{11}$ and $R^{12}$ is $Cy^1$;

each $Cy^1$ is independently selected from $C_{6-14}$ aryl, $C_{3-10}$ cycloalkyl, 5-10 membered heteroaryl, 4-10 membered heterocycloalkyl, ($C_{6-14}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl, (4-10 membered heterocycloalkyl)$C_{1-3}$ alkylenyl, wherein each of said $C_{6-14}$ aryl, $C_{3-10}$ cycloalkyl, 5-10 membered heteroaryl, 4-10 membered heterocycloalkyl, ($C_{6-14}$ aryl) $C_{1-3}$ alkylenyl, ($C_{3-10}$ cycloalkyl)$C_{1-3}$ alkylenyl, (5-10 membered heteroaryl)$C_{1-3}$ alkylenyl and (4-10 membered heterocycloalkyl)$C_{1-3}$ alkylenyl forming $Cy^1$ is optionally substituted by 1, 2, 3, 4 or 5 substituents independently selected from $Cy^2$, $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, C(=O)$R^{b1}$, C(=O)$NR^{c1}R^{d1}$, C(=O)$OR^{a1}$, OC(=O)$R^{b1}$, OC(=O)$NR^{c1}R^{d1}$, $NR^{c1}R^{d1}$, $NR^{c1}$C(=O)$R^{b1}$, $NR^{c1}$C(=O)$NR^{c1}R^{d1}$, $NR^{c1}$C(=O)$OR^{a1}$, C(=$NR^{e1}$)$NR^{c1}R^{d1}$, $NR^{c1}$C(=$NR^{e1}$)$NR^{c1}R^{d1}$, S(=O)$R^{b1}$, S(=O)$NR^{c1}R^{d1}$, S(=O)$_2R^{b1}$, $NR^{c1}$S(=O)$_2R^{b1}$ and S(=O)$_2NR^{c1}R^{d1}$;

each $Cy^2$ is independently selected from $C_{6-10}$ aryl, $C_{3-10}$ cycloalkyl, 5-10 membered heteroaryl, 4-10 membered heterocycloalkyl, ($C_{6-10}$ aryl)$C_{1-3}$ alkylenyl, ($C_{3-10}$ cycloalkyl) $C_{1-3}$ alkylenyl, (5-10 membered heteroaryl)$C_{1-3}$ alkylenyl, (4-10 membered heterocycloalkyl)$C_{1-3}$ alkylenyl, wherein each of said $C_{6-10}$ aryl, $C_{3-10}$ cycloalkyl, 5-10 membered heteroaryl, 4-10 membered heterocycloalkyl, ($C_{6-10}$ aryl) $C_{1-3}$ alkylenyl, ($C_{3-10}$ cycloalkyl)$C_{1-3}$ alkylenyl, (5-10 membered heteroaryl($C_{1-3}$ alkylenyl and (4-10 membered heterocycloalkyl)$C_{1-3}$ alkylenyl forming $Cy^2$ is optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, C(=O)$R^{b1}$, C(=O)$NR^{c1}R^{d1}$, C(=O)$OR^{a1}$, OC(=O)$R^{b1}$, OC(=O)$NR^{c1}R^{d1}$, $NR^{c1}R^{d1}$, $NR^{c1}$C(=O)$R^{b1}$, $NR^{c1}$C(=O)$NR^{c1}R^{d1}$, $NR^{c1}$C(=O)$OR^{a1}$, C(=$NR^{e1}$)$NR^{c1}R^{d1}$, $NR^{c1}$C(=$NR^{e1}$)$NR^{c1}R^{d1}$, S(=O)$R^{b1}$, S(=O)$NR^{c1}R^{d1}$, S(=O)$_2R^{1b}$, $NR^{c1}$S(=O)$_2R^{b1}$ and S(=O)$_2NR^{c1}R^{d1}$;

$R^{a1}$, $R^{b1}R^{c1}$ and $R^{d1}$ are each independently selected from H, $C_{1-6}$ alkyl, $C_{2-6}$ alkenyl and $C_{2-6}$ alkynyl; and each $R^{e1}$ is, independently, H, $C_{1-4}$ alkyl, CN or NO$_2$.

The present disclosure further provides a compound of Formula (I):

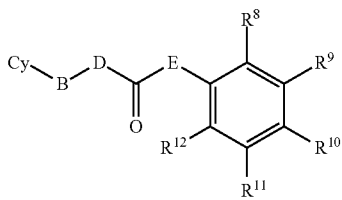

(I)

or a pharmaceutically acceptable salt thereof, wherein:
Cy is a group of Formula (Cy-A) or (Cy-B):

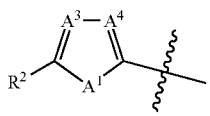

(Cy-A)

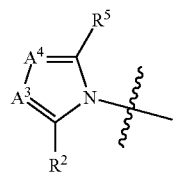

(Cy-B)

$A^1$ is $NR^1$, O or S;

$R^1$ is H or $C_{1-6}$ alkyl;

$R^2$ is H, $C_{1-6}$ alkyl, $C_{2-6}$ alkenyl, $C_{2-6}$ alkynyl, halogen, $C_{1-6}$ haloalkyl, $C_{6-10}$ aryl, $C_{3-10}$ cycloalkyl, 5-10 membered heteroaryl, 4-10 membered heterocycloalkyl, ($C_{6-10}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl, (4-10 membered heterocycloalkyl)$C_{1-3}$ alkylenyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=C)NR^{c1}R^{d1}$, $S(=O)_2R^{b1}$, $NR^{c1}S(=O)_2R^{b1}$ and $S(=O)_2NR^{c1}R^{d1}$, wherein each of said $C_{1-6}$ alkyl, $C_{6-10}$ aryl, $C_{3-10}$ cycloalkyl, 5-10 membered heteroaryl or 4-10 membered heterocycloalkyl, ($C_{6-10}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl or (4-10 membered heterocycloalkyl)$C_{1-3}$ alkylenyl forming $R^2$ is optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

$A^3$ is N or $CR^3$;

$R^3$ is selected from H, $C_{1-6}$ alkyl, $C_{2-6}$ alkenyl, $C_{2-6}$ alkynyl, halogen, $C_{1-6}$ haloalkyl, CN, $OR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$; or $R^2$ and $R^3$, together with the atoms to which $R^2$ and $R^3$ are attached, together form a fused benzo ring that is optionally substituted with 1, 2, 3 or 4 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

$A^4$ is N or $CR^4$;

$R^4$ is selected from H, $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

$R^5$ is selected from H, $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

B is absent (a bond), or is selected from $NR^6$, O, S, $S(O)$ and $S(O)_2$;

$R^6$ is H or $C_{1-6}$ alkyl;

D is $C_{1-4}$ alkylene optionally substituted by 1, 2, 3, 4 or 5 substituents selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

E is $NR^7$ or O;

$R^7$ is H or $C_{1-6}$ alkyl;

$R^8$, $R^9$, $R^{10}$, $R^{11}$ and $R^{12}$ are each independently selected from H, $C_{1-6}$ alkyl, $Cy^1$, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

provided that no more than two of $R^8$, $R^9$, $R^{10}$, $R^{11}$ and $R^{12}$ is $Cy^1$;

each $Cy^1$ is independently selected from $C_{6-14}$ aryl, $C_{3-10}$ cycloalkyl, 5-10 membered heteroaryl, 4-10 membered heterocycloalkyl, ($C_{6-14}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl, (4-10 membered heterocycloalkyl)$C_{1-3}$ alkylenyl, wherein each of said $C_{6-14}$ aryl, $C_{3-10}$ cycloalkyl, 5-10 membered heteroaryl, 4-10 membered heterocycloalkyl, ($C_{6-14}$ aryl)$C_{1-3}$ alkylenyl, ($C_{3-10}$ cycloalkyl)$C_{1-3}$ alkylenyl, (5-10 membered heteroaryl($C_{1-3}$ alkylenyl and (4-10 membered heterocycloalkyl)$C_{1-3}$ alkylenyl forming $Cy^1$ is optionally substituted by 1, 2, 3, 4 or 5 substituents independently selected from $Cy^2$, $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

each $Cy^2$ is independently selected from $C_{6-10}$ aryl, $C_{3-10}$ cycloalkyl, 5-10 membered heteroaryl, 4-10 membered heterocycloalkyl, ($C_{6-10}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl, (4-10 membered heterocycloalkyl)$C_{1-3}$ alkylenyl, wherein each of said $C_{6-10}$ aryl, $C_{3-10}$ cycloalkyl, 5-10 membered heteroaryl, 4-10 membered heterocycloalkyl, ($C_{6-10}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl and (4-10 membered heterocycloalkyl)$C_{1-3}$ alkylenyl forming $Cy^2$ is optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

$R^{a1}$, $R^{b1}$, $R^{c1}$ and $R^{d1}$ are each independently selected from H, $C_{1-6}$ alkyl, $C_{2-6}$ alkenyl and $C_{2-6}$ alkynyl; and each $Re'$ is, independently, H, $C_{1-4}$ alkyl, CN or $NO_2$.

In some embodiments, Cy is a group of Formula (Cy-A).
In some embodiments, Cy is a group of Formula (Cy-B).
In some embodiments, Cy is Cy-C.
In some embodiments, $A^1$ is $NR^{c1}$. In some such embodiments, $R^1$ is H. In some such embodiments, $R^1$ is $C_{1-6}$ alkyl, such as methyl or ethyl.
In some embodiments, $A^1$ is O.
In some embodiments, $A^1$ is S.
In some embodiments, $R^2$ is H, $C_{1-6}$ alkyl, $C_{2-6}$ alkenyl, $C_{2-6}$ alkynyl, halogen, $C_{1-6}$ haloalkyl, $C_{6-10}$ aryl, $C_{3-10}$ cycloalkyl, 5-10 membered heteroaryl, 4-10 membered heterocycloalkyl, ($C_{6-10}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl, (4-10 membered heterocycloalkyl)$C_{1-3}$ alkylenyl, CN, $OR^{a1}$, SW', $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=C)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$, wherein each of said $C_{1-6}$ alkyl, $C_{6-10}$ aryl, $C_{3-10}$ cycloalkyl, 5-10 membered heteroaryl or 4-10 membered heterocycloalkyl, ($C_{6-10}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl or (4-10 membered heterocycloalkyl)$C_{1-3}$ alkylenyl forming $R^2$ is optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, $R^2$ is H, $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, ($C_{6-10}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl, or (4-10 membered heterocycloalkyl)$C_{1-3}$ alkylenyl, wherein each of said $C_{1-6}$ alkyl, $C_{6-10}$ aryl, $C_{3-10}$ cycloalkyl, 5-10 membered heteroaryl or 4-10 membered heterocycloalkyl, ($C_{6-10}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl or (4-10 membered heterocycloalkyl)$C_{1-3}$ alkylenyl forming $R^2$ is optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, $R^2$ is H.
In some embodiments, $R^2$ is $C_{1-6}$ alkyl, such as methyl.
In some embodiments, $R^2$ is $C_{6-10}$ aryl, $C_{3-10}$ cycloalkyl, 5-10 membered heteroaryl, 4-10 membered heterocycloalkyl, ($C_{6-10}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl, or (4-10 membered heterocycloalkyl)$C_{1-3}$ alkylenyl, wherein each of said $C_{6-10}$ aryl, $C_{3-10}$ cycloalkyl, 5-10 membered heteroaryl or 4-10 membered heterocycloalkyl, ($C_{6-10}$ aryl)$C_{1-3}$ alkylenyl, ($C_{3-10}$ cycloalkyl)$C_{1-3}$ alkylenyl, (5-10 membered heteroaryl)$C_{1-3}$ alkylenyl or (4-10 membered heterocycloalkyl)$C_{1-3}$ alkylenyl forming $R^2$ is optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=C)OR^{a1}$, $C(=NR^{e1})NR^{c1}R^{d1}$, $NR^{c1}C(=NR^{e1})NR^{c1}R^{d1}$, $S(=O)R^{b1}$, $S(=C)NR^{c1}R^{d1}$, $S(=O)_2R^{b1}$, $NR^{c1}S(=O)_2R^{b1}$ and $S(=O)_2NR^{c1}R^{d1}$.

In some embodiments, $R^2$ is $C_{6-10}$ aryl, such as phenyl, that is optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, $R^2$ is phenyl, 4-methylphenyl, 2,4-dichlorophenyl, 4-methoxyphenyl, or 2-hydroxyphenyl.

In some embodiments, $R^2$ is 5-10 membered heteroaryl, $R^2$ is optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, $R^2$ is 4-10 membered heterocycloalkyl, ($C_{6-10}$ aryl)$C_{1-3}$ alkylenyl, or (4-10 membered heterocycloalkyl)$C_{1-3}$ alkylenyl, wherein each of 4-10 membered heterocycloalkyl, or (4-10 membered heterocycloalkyl)$C_{1-3}$ alkylenyl forming $R^2$ is optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2 NR^{c1}R^{d1}$.

In some embodiments, $R^2$ is 4-morpholinylmethyl.

In some embodiments, $R^2$ is selected from H, $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, n $R^2$ is $NR^{c1}R^{d1}$, such as $NH_2$.
In some embodiments, $A^3$ is N.
In some embodiments, $A^3$ is $CR^3$.
In some embodiments, $R^3$ is selected from H, $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, $A^3$ is $CR^3$ and $R^2$ and $R^3$, together with the atoms to which $R^2$ and $R^3$ are attached, together form a fused benzo ring that is optionally substituted with 1, 2, 3 or 4 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, $A^4$ is N.

In some embodiments, $A^4$ is $CR^4$.

In some embodiments, $R^4$ is H.

In some embodiments, $R^5$ is H.

In some embodiments, Cy-C is phenyl optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, Cy-C is 3-trifluoromethylphenyl.

In some embodiments, B is absent (a bond).

In some embodiments, B is S.

In some embodiments, B is S(O).

In some embodiments, B is $S(O)_2$.

In some embodiments, B is O.

In some embodiments, B is $NR^6$.

In some embodiments, $R^6$ is H.

In some embodiments, $R^6$ is $C_{1-6}$ alkyl, such as methyl.

In some embodiments, D is $C_{1-4}$ alkylene, such as $CH_2$, $CH_2CH_2$, $CH_2CH_2CH_2$ or $CH_2CH_2CH_2CH_2$.

In some embodiments, D is $C_1$ alkylene, such as $CH_2$.

In some embodiments, D is $C_2$ alkylene, such as $CH_2CH_2$.

In some embodiments, D is phenylene that is optionally substituted by 1, 2, 3 or 4 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$. In some embodiments, E is $NR^7$. D can be 1,2-phenylene, 1,3-phenylene, or 1,4-phenylene. D can be unsubstituted phenylene.

In some embodiments, D is heteroarylene that is optionally substituted by 1, 2, 3 or 4 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$. In some embodiments, E is $NR^7$. D can be 2,3-, 2,4-, 2,5-, 2,6- or 3,5-pyridylene. D can be unsubstituted pyridylene.

In some embodiments, $R^7$ is H.

In some embodiments, $R^7$ is $C_{1-6}$ alkyl, such as methyl.

In some embodiments, $R^7$ is $R^7$ is phenyl that is optionally substituted by 1, 2, 3 or 4 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$. $R^7$ can be, e.g., unsubstituted phenyl.

In some embodiments, $R^7$ is 5-6 membered heteroaryl that is optionally substituted by 1, 2, 3 or 4 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$. $R^7$ can be, e.g., unsubstituted pyridyl. $R^7$ can be, e.g., 2-pyridyl, 3-pyridyl or 4-pyridyl.

In some embodiments, E is O.

In some embodiments, $R^8$ is selected from H, $C_{1-6}$ alkyl, such as methyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $Q=NR^{c1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2 NR^{c1}R^{d1}$.

In some embodiments, $R^8$ is H.

In some embodiments, $R^8$ is halogen, such as F, Cl or Br.

In some embodiments, $R^9$ is selected from H, $C_{1-6}$ alkyl, such as methyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2 NR^{c1}R^{d1}$.

In some embodiments, $R^9$ is H.

In some embodiments, $R^9$ is $Cy^1$.

In some embodiments, $R^{10}$ is selected from H, $C_{1-6}$ alkyl, such as methyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2 NR^{c1}R^{d1}$.

In some embodiments, $R^{10}$ is H.

In some embodiments, $R^{10}$ is $Cy^1$.

In some embodiments, $Cy^1$ is $C_{6-14}$ aryl, $C_{3-10}$ cycloalkyl, $(C_{6-14}$ aryl)$C_{1-3}$ alkylenyl, or $(C_{3-10}$ cycloalkyl)$C_{1-3}$ alkylenyl, wherein each of said $C_{6-14}$ aryl, $C_{3-10}$ cycloalkyl, $(C_{6-14}$ aryl)$C_{1-3}$ alkylenyl or $(C_{3-10}$ cycloalkyl)$C_{1-3}$ alkylenyl forming $Cy^1$ is optionally substituted by 1, 2, 3, 4 or 5 substituents independently selected from $Cy^2$, $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, $Cy^1$ is $C_{6-14}$ aryl, such as phenyl, optionally substituted by 1, 2, 3, 4 or 5 substituents independently selected from $Cy^2$, $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)$ $R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, $Cy^1$ is phenyl, 1- or 2-naphthyl, 1-, 2-, 3-, 4- or 9-phenanthrenyl, or 1-, 2- or 9-anthracenyl.

In some embodiments, $Cy^1$ is phenyl, 4-cyclohexylphenyl, 3-trifluoromethylphenyl, 3,5-trifluoromethylphenyl, 4-methylphenyl, 4-ethylphenyl, 4-n-propylphenyl, 4-i-propylphenyl, 4-n-butylphenyl, 4-t-butylphenyl, 2,6-dimethylphenyl, 3,5-dimethylphenyl, 1,1'-biphenyl-3-yl, 1,1'-biphenyl-4-yl, 3,5-diphenylphenyl.

In some embodiments, $Cy^1$ is $C_{3-10}$ cycloalkyl, optionally substituted by 1, 2, 3, 4 or 5 substituents independently selected from $Cy^2$, $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, $Cy^1$ is adamantyl.

In some embodiments, each $Cy^2$ is independently selected from $C_{6-10}$ aryl, $C_{3-10}$ cycloalkyl, $(C_{6-10}$ aryl)$C_{1-3}$ alkylenyl, and $(C_{3-10}$ cycloalkyl)$C_{1-3}$ alkylenyl, wherein each of said $C_{6-10}$ aryl, $C_{3-10}$ cycloalkyl, $(C_{6-10}$ aryl)$C_{1-3}$ alkylenyl, or $(C_{3-10}$ cycloalkyl)$C_{1-3}$ alkylenyl, forming $Cy^2$ is optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, each $Cy^2$ is independently selected from $C_{6-10}$ aryl, such as phenyl, optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, each $Cy^2$ is phenyl.

In some embodiments, each $Cy^2$ is independently selected from $C_{3-10}$ cycloalkyl optionally substituted by 1, 2, 3, 4 or 5 substituents independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, each $Cy^2$ is cyclohexyl.

In some embodiments, $R^{11}$ is selected from H, $C_{1-6}$ alkyl, such as methyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, $R^{11}$ is H.

In some embodiments, $R^{12}$ is selected from H, $C_{1-6}$ alkyl, such as methyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=C)NR^{c1}R^{d1}$, $S(=O)_2R^{b1}$, $NR^{c1}S(=O)_2R^{b1}$ and $S(=O)_2 NR^{c1}R^{d1}$.

In some embodiments, $R^{12}$ is H.

In some embodiments, no more than one of $R^8$, $R^9$, $R^{10}$, $R^{11}$ and $R^{12}$ is $Cy^1$.

In some embodiments, one and only one of $R^8$, $R^9$, $R^{10}$, $R^{11}$ and $R^{12}$ $R^7$, $R^8$, $R^9$, $R^{10}$ and $R^{11}$ is $Cy^1$.

In some embodiments, $R^{a1}$, $R^{b1}$, $R^{c1}$ and $R^{d1}$ are each independently selected from H and $C_{1-6}$ alkyl, such as methyl.

In some embodiments, each $R^{12}$ is H or $C_{1-6}$ alkyl, such as methyl, preferably H.

In some embodiments, the compound is a compound of one of the following formulae (I-1) to (I-24), and the variables can be as defined above for formula (I), or any of the embodiments thereof:

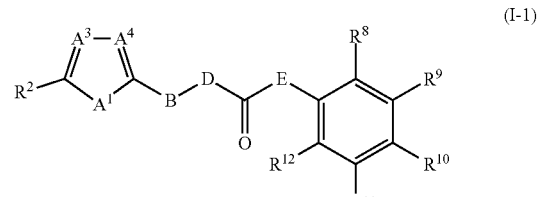

(I-1)

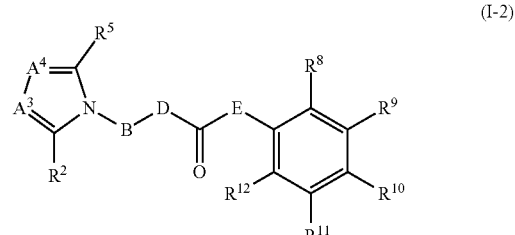

(I-2)

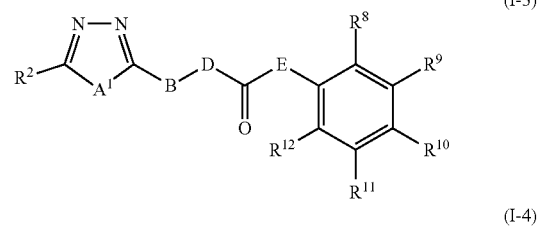

(I-3)

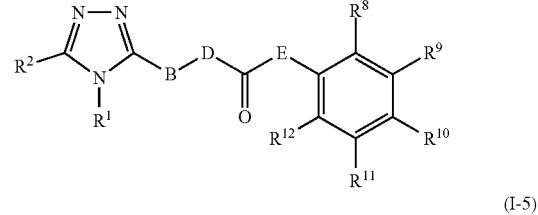

(I-4)

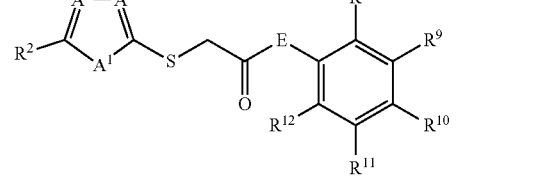

(I-5)

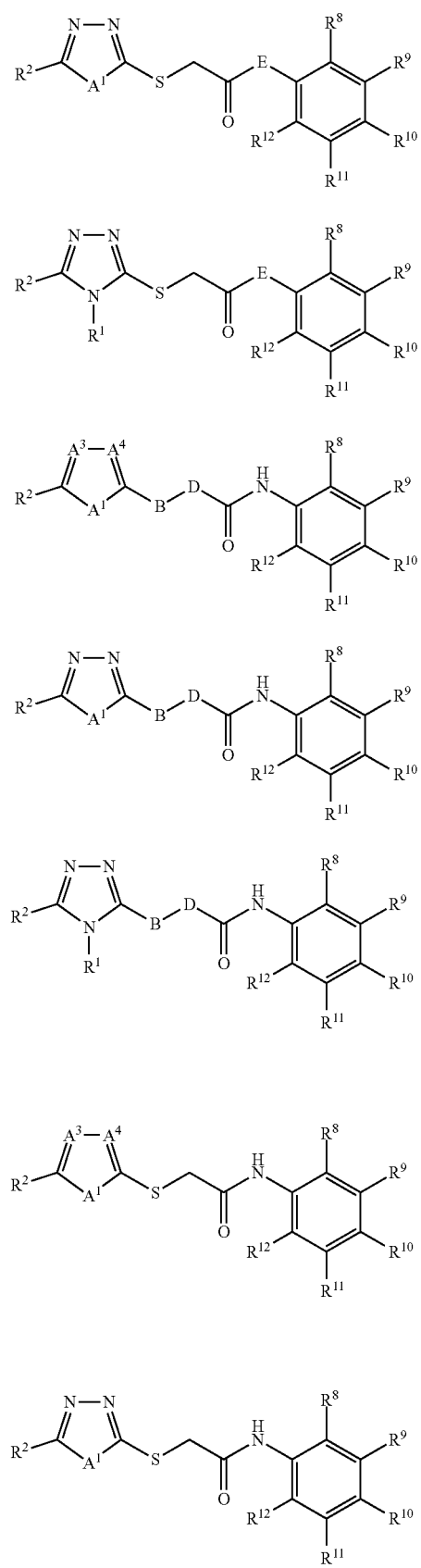
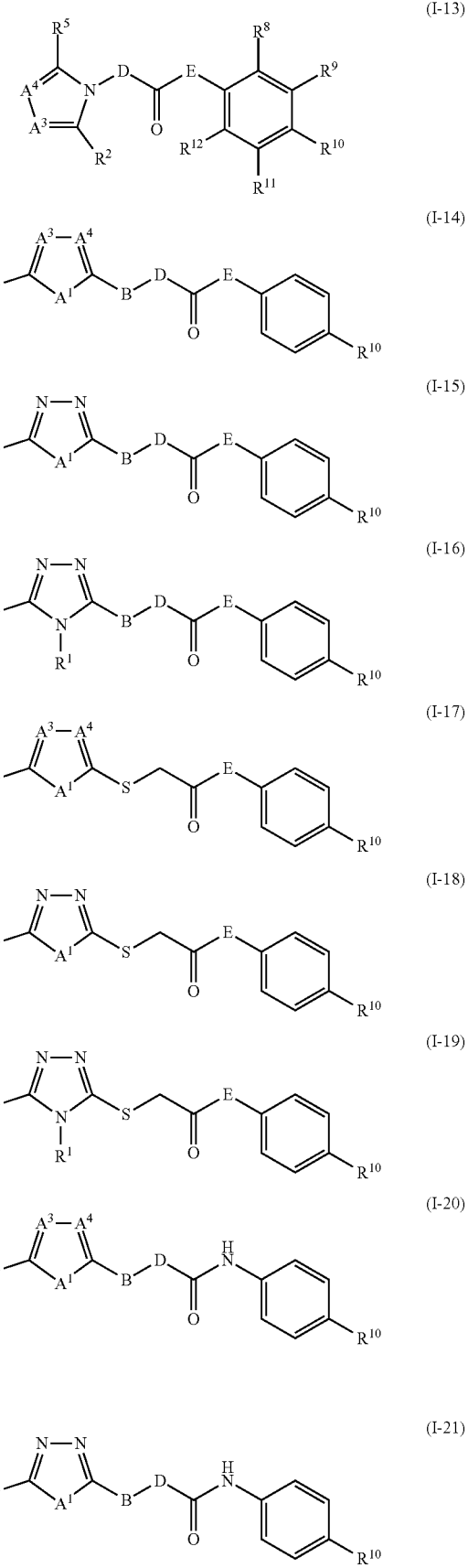

(I-22)
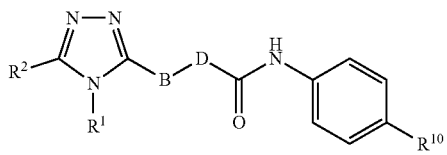

(I-23)
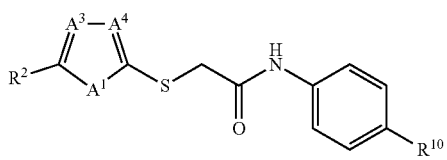

(I-24)
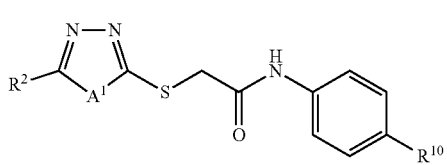

In some embodiments, the compound is a compound of one of the following formulae (I-25) to (I-30), and the variables can be as defined above for formula (I), or any of the embodiments thereof:

(I-25)
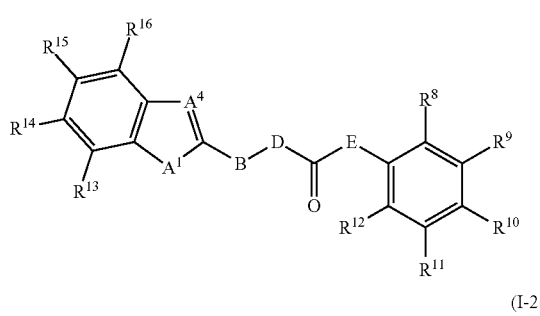

(I-26)
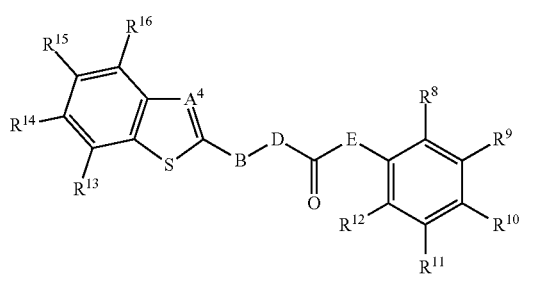

(I-27)
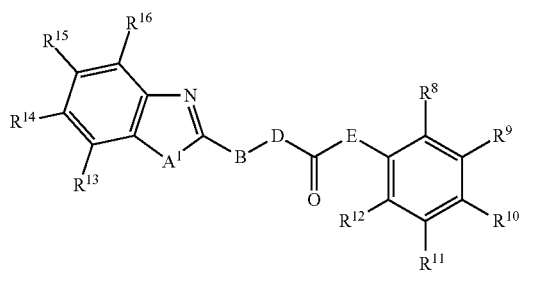

(I-28)
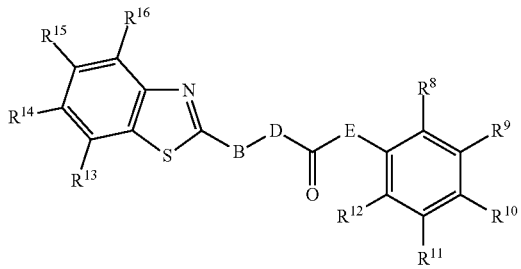

(I-29)
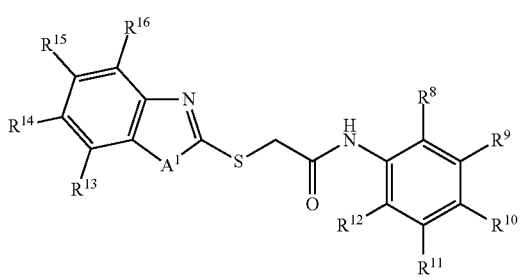

(I-30)

and wherein $R^{13}$, $R^{14}$, $R^{15}$ and $R^{16}$ are each independently selected from $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=C)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

In some embodiments, the compound is a compound of one of the following formula (4) to (53) as described above.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated that features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups are described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The term "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chain or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The terms "halo" or "halogen", used alone or in combination with other terms, refers to fluoro, chloro, bromo and iodo.

The term "haloalkyl" refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "amino" refers to a group of formula —$NH_2$.

The term "carbamyl" refers to a group of formula —C(=O)$NH_2$.

The term "carbonyl", employed alone or in combination with other terms, refers to a —C(=O)— group, which also may be written as C(O).

The term "carbonyl", employed alone or in combination with other terms, refers to a —C(=O)— group.

The term "carboxy" refers to a group of formula —C(=O)OH.

The term "oxo" refers to oxygen as a divalent substituent, forming a carbonyl group, or attached to a heteroatom forming a sulfoxide or sulfone group, or an N-oxide group.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, indenyl and the like. In some embodiments, aryl groups have from 6 to 10 carbon atoms. In some embodiments, the aryl group is phenyl.

The term "arylalkylenyl," employed alone or in combination with other terms, refers to an aryl group, as defined herein, attached to an alkylene group, as defined herein. The term "$C_{n-m}$ aryl $C_{o-p}$ alkylenyl" refers to an arylalkylenyl group with an aryl group having from n to m ring carbon atoms attached to an alkylene group having from o to p carbon atoms. Arylalkylenyl groups include, e.g., benzyl, phenethyl and the like.

The term "heteroaryl" or "heteroaromatic" employed alone or in combination with other terms, refers to a monocyclic or polycyclic aromatic heterocycle having at least one heteroatom ring member selected from sulfur, oxygen and nitrogen. In some embodiments, the heteroaryl is 5- to 10-membered $C_{1-9}$ heteroaryl, which is monocyclic or bicyclic and which has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1, 2, 3, or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, imidazo[1,2-b]pyridazine, purine, furopyridine (e.g., furo[3,2-b]pyridine), thienopyridine (e.g. thieno[3,2-b]pyridine) or the like.

A five-membered heteroaryl ring is a heteroaryl group having five ring atoms wherein one or more (e.g., 1, 2, 3 or 4) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "heteroarylalkylenyl," employed alone or in combination with other terms, refers to heteroaryl group, as defined herein, attached to an alkylene group, as defined herein. The term "n-m membered heteroaryl $C_{o-p}$ alkylenyl" refers to a heteroaryl group having from n to m ring atoms attached to an alkylene group having from o to p carbon atoms. Heteroarylalkylenyl groups include, e.g., pyridylmethyl, pyridylethyl and the like.

The term "cycloalkyl", employed alone or in combination with other terms, refers to a non-aromatic, saturated, monocyclic, bicyclic or polycyclic hydrocarbon ring system, including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have, e.g., 3, 4, 5, 6, 7, 8, 9 or 10 ring-forming carbons ($C_{3-10}$) or 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally substituted by oxo or sulfido.

Cycloalkyl groups also include cycloalkylidenes. Example cycloalkyl groups include cyclopropyl, cyclobutyl, cyclopentyl, cyclohexyl, cyclopentenyl, cyclohexenyl, cyclohexadienyl, norbornyl, norpinyl, bicyclo[2.1.1]hexanyl, bicyclo[1.1.1]pentanyl, adamantyl and the like. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like, for example indanyl or tetrahydronaphthyl. A cycloalkyl group containing a fused aromatic ring can be attached through any ring-forming atom including a ring-forming atom of the fused aromatic ring.

The term "arylalkylenyl," employed alone or in combination with other terms, refers to a cycloalkyl group, as defined herein, attached to an alkylene group, as defined herein. The term "$C_{n-m}$ cycloalkyl $C_{o-p}$ alkylenyl" refers to an cycloalkylalkylenyl group with a cycloalkyl group having from n to m ring carbon atoms attached to an alkylene group having from o to p carbon atoms. Cycloalkylalkylenyl groups include, e.g., cyclopropylmethyl, cyclopropylethyl, cyclobutylmethyl, cyclohexylmethyl, and the like.

The term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4-10 ring members, 4-7 ring members or 4-6 ring members. Included in heterocycloalkyl are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Examples of heterocycloalkyl groups include azetidine, pyrrolidine, piperidine, piperazine, morpholine, thiomorpholine, pyran, azepane, tetrahydropyran, tetrahydrofuran, dihydropyran, dihydrofuran and the like. Ring-forming carbon atoms and heteroatoms of a heterocycloalkyl group can be optionally substituted by oxo or sulfido (e.g., $C(=O)$, $S(=O)$, $C(S)$ or $S(=O)_2$, etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 1,2,3,4-tetrahydroquinoline, dihydrobenzofuran, azetidine, azepane, diazepan (e.g., 1,4-diazepan), pyrrolidine, piperidine, piperazine, morpholine, thiomorpholine, pyran, tetrahydrofuran and di- and tetra-hydropyran.

The term "heterocycloalkylalkylenyl," employed alone or in combination with other terms, refers to heterocycloalkyl group, as defined herein, attached to an alkylene group, as defined herein. The term "n-m membered heterocycloalkyl $C_{o-p}$ alkylenyl" refers to a heterocycloalkyl group having from n to m ring atoms attached to an alkylene group having from o to p carbon atoms. Heteroarylalkylenyl groups include, e.g., tetrahydrofurylmethyl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," is meant to include all stereoisomers, geometric isomers, tautomers and isotopes of the structures depicted.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature" are understood in the art, and refer generally to a temperature, e.g., a reaction temperature, that is about the temperature of the room in which the reaction is carried out, e.g., a temperature from about 20° C. to about 30° C.

The present invention also includes salts, particularly pharmaceutically acceptable salts, of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences,* 17th Ed., (Mack Publishing Company, Easton, 1985), p. 1418, Berge et al., *J. Pharm. Sci.,* 1977, 66(1), 1-19 and in Stahl et al., *Handbook of Pharmaceutical Salts: Properties, Selection, and Use,* (Wiley, 2002). In some embodiments, the compounds described herein include the N-oxide forms.

The following abbreviations may be used herein: AcOH (acetic acid); $Ac_2O$ (acetic anhydride); $Al_2O_3$ (aluminium oxide); aq. (aqueous); atm. (atmosphere(s)); Boc (t-butoxycarbonyl); Boc2O (di-tert-butyldicarbonate); BOP ((benzotriazol-1-yloxy)tris(dimethylamino)phosphonium hexafluorophosphate); br (broad); c-Pr (cyclopropyl); Cbz (carboxybenzyl); calc. (calculated); $CeCl_3 \cdot 7H_2O$ (cerium (III) chloride heptahydrate); $Cs_2CO_3$ (cesium carbonate); CuI (copper (I) iodide); d (doublet); dd (doublet of doublets); DCM (dichloromethane); DIPEA (N,N-diisopropylethylamine); DMAP (4-dimethylaminopyridine); DMF (N,N-dimethylformamide); DMSO (dimethylsulfoxide); Et (ethyl); EtOAc (ethyl acetate); EtOH (ethanol); Fmoc (9-fluorenylmethylmethoxycarbonyl); g (gram(s)); h (hour(s)); $H_2$ (hydrogen gas); $H_2O_2$ (hydrogen peroxide); HATU (N,N,N',N'-tetramethyl-O-(7-azabenzotriazol-1-yl) uronium hexafluorophosphate); HBr (hydrogen bromide); HCl (hydrochloric acid or hydrogen chloride); HPLC (high performance liquid chromatography); Hz (hertz); i-Pr (isopropyl); i-PrOH (isopropyl alcohol); J (coupling constant); KOAc (potassium acetate); $K_3PO_4$ (potassium phosphate); $K_3PO_4 \cdot H_2O$ (tripotassium phosphate hydrate); LCMS (liquid chromatography mass spectrometry); $LiAlH_4$ (lithium tetrahydroaluminate); $LiBH_4$ (lithium tetrahydroborate); LiOH (lithium hydroxide); $LiOH \cdot H_2O$ (lithium hydroxide monohydrate); m (multiplet); M (molar); mCPBA (m-chloroperbenzoic acid); Me (methyl); MeCN (acetonitrile); MeOH (methanol); $MgSO_4$ (magnesium sulfate); MS (mass spectrometry); mg (milligram(s)); min. (minutes(s)); mL (milliliter(s)); mmol (millimole(s)); N (normal); $N_2$ (nitrogen gas); $NaHCO_3$ (sodium bicarbonate); $NaIO_4$ (sodium metaperiodate); $NaN_3$ (sodium azide); NaOH (sodium hydroxide); $Na_2SO_4$ (sodium sulfate); n-Bu (n-butyl); n-BuLi (n-butyllithium); $NH_4Cl$ (ammonium chloride); $NH_4OH$ (ammonium hydroxide); nM (nanomolar); NMR (nuclear magnetic resonance spectroscopy); Pd (palladium); $Pd(dppf)Cl_2$ ([1,1'-bis(diphenylphosphino)ferrocene]palladium(II) dichloride); $Pd(OAc)_2$ (palladium acetate); $Pd(tBu_3P)_2$ (bis(tri-tert-butylphosphine)palladium); pM (picomolar); $Pd(PPh_3)_4$ (tetrakis(triphenylphosphine)palladium(O)); $PPh_3$ (triphenylphosphine); psi (pounds per square inch); PTFE (polytetrafluoroethylene); RP-HPLC (reverse phase high performance liquid chromatography); s (singlet); t (triplet or tertiary); tert (tertiary); tt (triplet of triplets); TBAF (tetra-n-butylammoniumfluoride); t-Bu (tert-butyl); TEA (triethylamine); TFA (trifluoroacetic acid); THF (tetrahydrofuran); µg (microgram(s)); µL (microliter(s)); µm (micromolar); wt % (weight percent).

III. Synthesis

Compounds of the invention, including salts thereof, can be prepared using known organic synthesis techniques and can be synthesized according to any of numerous possible synthetic routes, such as shown in the Scheme below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups,* (Thieme, 2007); Robertson, *Protecting Group Chemistry,* (Oxford University Press, 2000); Smith et al., *March's Advanced Organic Chemistry: Reactions, Mechanisms, and Structure,* $6^{th}$ Ed. (Wiley, 2007); Peturssion et al., "Protecting Groups in Carbohydrate Chemistry," *J. Chem. Educ.,* 1997, 74(11), 1297; and Wuts et al., *Protective Groups in Organic Synthesis,* 4th Ed., (Wiley, 2006).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared as shown in Scheme 1 by coupling a carboxylic acid derivative of Formula (II) with an aniline of Formula (III) or a phenol of Formula (IV). In the compound of Formula (II), L is a suitable leaving group, which can include: OH, halogen, Oalkyl, Oaryl, OCOalkyl, or OCOaryl. A suitable or ester or amide-forming procedure involves treatment of a compound of Formula (II) with a compound of Formula (III) at 0-120° C. in a suitable solvent. The presence of a base, or, when Y=OH, a coupling agent, may also be necessary for the reaction to occur. Suitable bases for the reaction include: 4-(NN-dimethylamino)pyridine, pyridine, triethylamine, N,N-diisopropylethylamine. Suitable coupling agents when L=OH include: carbodiimides, for example 1,3-dicyclohexylcarbodiimide or 1-(3-dimethylaminopropyl-3-ethylcarbodiimide hydrochloride; phosphonium reagents, for example benzotriazol-1-yloxytris(dimethylamino)phosphonium hexafluorophosphate or benzotriazol-1-yloxytripyrrolidino-phosphonium hexafluorophosphate; and uronium reagents, for example 0-benzotriazol-1-yl-N,N,N',N'-tetramethyluronium tetrafluoroborate. Suitable solvents for the reaction include N,N-dimethylformamide, dimethylsulfoxide, tetrahydrofuran, or chloroform. The preferred solvent is N,N-dimethylformamide. The reaction can typically be performed at a temperature of 0-50° C., e.g., a temperature of 20-30° C.

SCHEME 1

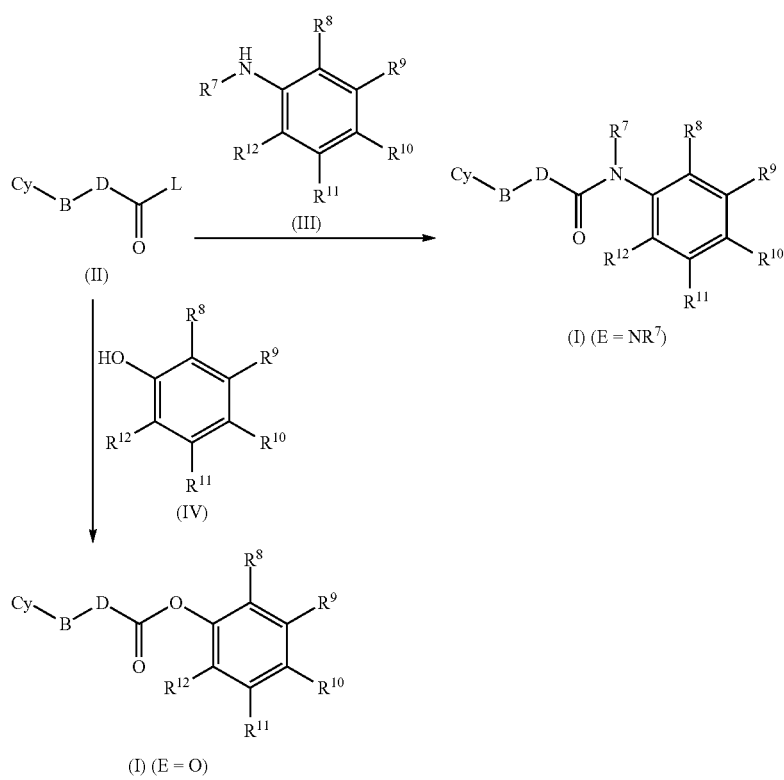

Compounds of Formula (I) can be alternatively prepared as shown in Scheme 2 by coupling a compound of formula (V), wherein L is a suitable L is a suitable leaving group, which can include: halogen or a sulfonategroup (alkyl or aryl sulfonate, such as methanesulfonate, trifluoromethanesulfonate, benzenesulfonate, p-toluenesulfonate, or naphthalenesulfonate) with a suitable hydroxy (BH=OH), mercapto (BH=SH) or amino compound (BH=NHR$^6$) of Formula (VI). A suitable procedure involves treatment of a compound of Formula (V) with a compound of Formula (VI) at 0-120° C. in a suitable solvent. The presence of a base may also be necessary for the reaction to occur. Suitable bases for the reaction include: 4-(NN-dimethylamino)pyridine, pyridine, triethylamine, N,N-diisopropylethylamine, sodium hydride, sodium methoxide, sodium ethoxide, or sodium hydroxide. Suitable solvents for the reaction include N,N-dimethylformamide, dimethylsulfoxide, tetrahydrofuran, or chloroform. The preferred solvent is N,N-dimethylformamide. The reaction can typically be performed at a temperature of 0-50° C., e.g., a temperature of 20-30° C.

SCHEME 2

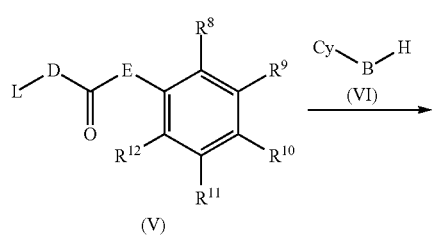

-continued

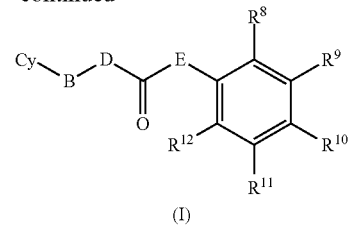

Compounds of Formula (II), (III), (IV), (V) and (VI) are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (*Journal of Heterocyclic Chemistry*, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

IV. Uses of the Compounds

Compounds of the invention can inhibit the autopalmitoylation of TEAD-transcription factors and, thus, are useful in treating diseases and disorders associated with activity of TEAD-transcription factors. For the uses described herein, any of the compounds of the invention, including any of the embodiments thereof, may be used.

Thus, the present disclosure provides methods of treating a TEAD-transcription factor-associated disease or disorder in an individual (e.g., patient) by administering to the individual in need of such treatment a therapeutically effective amount or dose of a compound of Formula (I), or any of the embodiments thereof, or a pharmaceutical composition thereof. The present disclosure also provides a compound of Formula (I), or any of the embodiments thereof, or a pharmaceutical composition thereof, for use in treating a TEAD-transcription factor associated disease or disorder. Also provided is the use of a compound of Formula (I), or any of the embodiments thereof, or a pharmaceutical composition thereof, in the manufacture of a medicament for treating a TEAD-transcription factor-associated disease or disorder. The disease or disorder can be one that is associated with TEAD1, TEAD2, TEAD3, or TEAD4.

A TEAD-transcription factor-associated disease can include any disease, disorder or condition that is directly or indirectly linked to expression or activity of TEAD-transcription factors, including over-expression and/or abnormal activity levels. Abnormal activity levels can be determined by comparing activity level in normal, healthy tissue or cells with activity level in diseased cells. A TEAD-transcription factor-associated disease can also include any disease, disorder or condition that can be prevented, ameliorated, inhibited or cured by modulating TEAD-transcription factor activity. In some embodiments, the disease is characterized by the abnormal activity or expression (e.g., overexpression) of TEAD-transcription factor. A TEAD-transcription factor-associated disease can also refer to any disease, disorder or condition wherein modulating the expression or activity TEAD-transcription factor is beneficial.

TEAD-transcription factor associated diseases that can be treated using the compounds of the invention include cancer. The cancers include solid tumors, e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head or neck, thyroid cancer, glioblastoma, sarcoma, bladder cancer, etc. Other TEAD-transcription factor associated diseases include hepatocellular carcinoma, medulloblastoma, cutaneous squamous cell carcinoma, lung cancer, pancreatic cancer, esophagus cancer, liver cancer, colon cancer, melanoma, or uveal melanoma. TEAD-transcription factor associated diseases also include hematological cancers, e.g., lymphoma, leukemia such as acute lymphoblastic leukemia (ALL), acute myelogenous leukemia (AML), chronic lymphocytic leukemia (CLL), chronic myelogenous leukemia (CML), diffuse large B-cell lymphoma (DLBCL), mantle cell lymphoma, non-Hodgkin lymphoma (including relapsed non-Hodgkin lymphoma, refractory non-Hodgkin lymphoma and recurrent follicular non-Hodgkin lymphoma), Hodgkin lymphoma and multiple myeloma.

The cancer can be a cancer in which abnormally proliferating cells of the cancer express one or more TEADs, for example, a cancer that expresses one or more of TEAD1, TEAD2, TEAD3, and/or TEAD4. The method can include testing cancer cells of the individual for expression of one or more TEADs, e.g., one or more of TEAD1, TEAD2, TEAD3, and/or TEAD4, and treating the cancer according to the methods described herein based on the determination that the cancer expresses TEAD1, TEAD2, TEAD3, and/or TEAD4.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different chemotherapeutic agents treat such conditions. Use of combination therapy may reduce the likelihood of drug-resistance arising in a cell population, and/or reduce the toxicity of treatment.

The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

When more than one pharmaceutical agent is administered to a patient, they can be administered simultaneously, sequentially, or in combination (e.g., for more than two agents).

VI. Formulation, Dosage Forms and Administration

When employed as pharmaceuticals, the compounds of the invention can be administered in the form of pharmaceutical compositions. Thus the present disclosure provides a composition comprising a compound Formula (I), or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™) In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

V. Labeled Compounds and Assay Methods

The compounds of the invention can further be useful in investigations of biological processes in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating TEAD transcription factor in tissue samples, including human, and for identifying TEAD transcription factor ligands by inhibition binding of a labeled compound. Accordingly, the present invention includes assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, the compound incorporates 1, 2 or 3 deuterium atoms. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a TEAD transcription factor by monitoring its concentration variation when contacting with the TEAD transcription factor, through tracking of the labeling. For example, a test compound (labeled) can be evaluated for its ability to reduce binding of another compound which is known to bind to a TEAD transcription factor (i.e., standard compound). Accordingly, the ability of a test compound to compete with the standard compound for binding to the TEAD transcription factor directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VII. Kits

The present disclosure also includes pharmaceutical kits useful, e.g., in the treatment or prevention of TEAD transcription factor-associated diseases or disorders, such as cancer, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

HEK293A, Phoenix, MCF10A and C2C12 cell lines used herein (obtained from ATCC, Manassas, Va.) were grown at 37° C. with 5% $CO_2$. HEK293A, Phoenix, and C2C12 cell lines were cultured in Dulbecco's modified Eagles media (DMEM) (Life technologies) supplemented with 10% fetal bovine serum (FBS) (Thermo/Hyclone, Waltham, Mass.) and 50 µg/mL penicillin/streptomycin. MCF10A cells were cultured in DMEM/$F_{12}$ (Life technologies) supplemented with 5% horse serum, 20 ng/mL EGF, 0.5 µg/mL hydrocortisone, 100 ng/mL cholera toxin, 10 µg/mL insulin and 50 µg/mL penicillin/streptomycin. None of cell lines used herein are listed in the database of commonly misidentified cell lines maintained by ICLAC. All cell lines are free of *mycoplasma* contamination.

Plasmids were transfected with jetPRIME (Polyplus transfection) or XtremeGene HP (Roche) according to the manufacturer's instructions. For retrovirus production, Phoenix cells were transfected with VSV-G and empty pBabe hygro or pBabe hygro containing TEAD1 wild type or 3CS mutant cDNA. Supernatants were collected by centrifugation and filtered through a 0.45 µm syringe filter (Corning) 48 h post-transfection. Cells were infected with 2 mL viral supernatant in the presence of 10 µg/mL polybrene (Millipore). Cells were incubated for 24-48 h before splitting into selection medium.

No statistical method was used to predetermine sample size. The experiments were not randomized. For biochemical experiments we performed the experiments at least three independent times. Experiments for which we showed representative images were performed successfully at least 3 independent times. No samples or animal were excluded from the analysis. The investigators were not blinded to allocation during experiments and outcome assessment. All P values were determined using two-tailed t-tests and statistical significance was set at P=0.05. The variance was similar between groups that we compared.

Example 1: Labeling, Click Reactions and Streptavidin Pull-Down

HEK293A or MCF10A cells were labeled with DMSO or probe 1, 2 or 3 overnight:

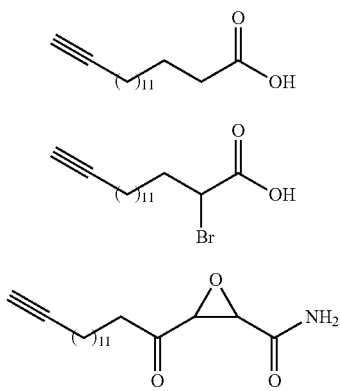

Cells were lysed in lysis buffer (50 mM TEA-HCl, pH 7.4, 150 mM NaCl, 1% Triton X-100, 0.2% SDS, cOmplete EDTA-free protease inhibitors) followed by Click reaction with biotin-azide. Zheng, B. et al. *J. Am. Chem. Soc.*, 2013, 135, 7082-7085. Proteins were precipitated with 9 volumes of 100% methanol for 2 h or overnight at −20° C. Proteins were recovered by centrifugation at 14,000×g for 10 min and the precipitants were suspended in suspension buffer (50 mM Tris-HCl, pH 7.7, 150 mM NaCl, 10 mM EDTA, 1% SDS, 0.5% NP-40). Labeled cellular proteins were enriched using streptavidin agarose (Life technologies) at room temperature with rotation overnight. Protein-bound streptavidin agarose beads were washed three times with suspension buffer without NP-40 and bound proteins were eluted with elution buffer (30 mM D-Biotin, 2% SDS, 6M Urea). Samples were processed with SDS-PAGE sample buffer and proteins were resolved by SDS-PAGE.

TEAD 1-4 in these samples were detected using TEAD-specific antibodies and streptavidin HRP. See FIG. 1A, FIG. 1B, and FIG. 1C. FIG. 1A is a streptavidin blot of probe 1 and 2 labeled myc-TEAD1 and myc-TEAD4 in HEK293A cells, showing the palmitoylation of TEADs. FIG. 1B are Western blots of TEAD1-4, showing endogenous human TEAD1-4 are all palmitoylated. The palmitoylated proteome of HEK293A and MCF10A cells was labeled by 1, and enriched by streptavidin beads. Western blots of TEAD1-4 were carried out in the pull-down samples using anti-TEAD1, 2, 3, 4 antibodies. FIG. 1C is streptavidin blot, showing S-palmitoylated and hydroxylamine treatment dramatically decreased TEAD1 palmitoylation levels. Blots were probes with anti-TEAD1 (#8526, 1:1000, Cell Signaling), anti-TEAD2 (#8870, 1:1000, Cell Signaling), anti-TEAD3 (#13224, 1:1000, Cell Signaling), anti-TEAD4 (ab58310, 1:1000, Abcam) and Streptavidin HRP (1:5000, Life technologies).

Example 2: Co-Immunoprecipitation

HEK293A cells were transfected with the indicated above. After 48 h, cells were lysed with lysis buffer (50 mM Tris-HCl, pH 7.3, 150 mM NaCl, 0.5 mM EDTA, 1% Triton X-100, PhosSTOP phosphatase inhibitor cocktail, cOmplete EDTA-free protease inhibitors cocktail). Flag-YAP or Myc-TEAD1 was immunoprecipitated with anti-FLAG M2 magnetic beads (Sigma Aldrich) or anti-c-Myc antibody (M4439, Sigma Aldrich), respectively, overnight with rotation at 4° C. TEAD1 was captured using Protein A/G magnetic resins (Life technologies). Protein-bound resins were washed three times with lysis buffer and processed with SDS-PAGE sample buffer. Blots were probed with anti-c-Myc (Sigma Aldrich), anti-HA (Sigma Aldrich), anti-FLAG M2 (F1804, Sigma Aldrich).

Example 3: FRET-Based Alpha Screen Binding Assay

Myc-TEAD1 and Flag-YAP or Flag-VGLL4 were transfected into HEK293A cells and 24-48 h post-transfection, cells were lysed with lysis buffer (20 mM Tris-HCl, pH 7.5, 150 mM NaCl, 1 mM EDTA, 1 mM EGTA, 1% Triton X-100, PhosSTOP phosphatase inhibitor cocktail, cOmplete EDTA-free protease inhibitor). Anti-c-myc acceptor beads (Perkin Elmer) were added to each well and incubated for 2 h prior to addition of anti-FLAG donor beads (Perkin Elmer). Samples were incubated overnight in darkness and Alpha signals were recorded using Perkin Elmer EnVision plate reader.

Example 4: Luciferase Assay

Gal-UAS-Luc, YAP, Gal4-TEAD1, Gal4-DBD or Myc-TEAD1 and *Renilla* luciferase control constructs were transfected into 293T cells and 48 h post-transfection, cells were processed using the Dual-Glo luciferase assay system (Promega) following manufacturer's instructions. Luminescence of Firefly and *Renilla* luciferase activities were quantified using Perkin Elmer EnVision plate reader.

Example 5: Ni-NTA Pull-Down and Acyl-Biotin Exchange

Recombinant $His_6$TEAD2 was incubated with Ni-NTA resin (Life technologies) in PBS for 1 h at 4° C. Protein-bound resins were washed and then incubated with 50 μM alkyne palmitoyl-CoA for 2 h at 25° C. Resins were split into two equivalent reactions, washed with PBS and treated with 50 mM NEM (Thermo Scientific) overnight at 4° C. Samples were incubated with or without 0.5 M hydroxylamine (Sigma Aldrich) for 1 h at room temperature and then incubated with 1 μM Biotin-BMCC (Pierce Biotechnology, Inc.) for 1 h at room temperature. Samples were washed and processed with SDS-sample buffer. Proteins were resolved by SDS-PAGE and visualized by immunoblotting with streptavidin HRP, anti-His antibody (SAB1306085, Sigma Aldrich) or Coomassie blue staining.

Example 6: C2C12 Cells Differentiation

C2C12 cells were transduced using retrovirus containing vector control (pBabe hygro), wild type or 3CS TEAD1.

Stable expression was selected initially using 600 μg/mL Hygromycin B (Life technologies) and then decreased to 300 μg/mL for 2 weeks. To induce differentiation, the culture condition was replaced by differentiation medium (DMEM+ 2% horse serum+50 μg/mL penicillin/streptomycin) with medium change everyday.

Example 7: Immunofluorescence

Cells were fixed with 4% paraformaldehyde and then permeabilized and blocked with 3% (w/v) BSA/PBS+0.1% Triton X-100 at room temperature for 30 min. Cells were immunostained with anti-myosin (skeletal, fast) chain (M4276, 1:400, Sigma Aldrich), anti-Yap (1:1000, Abgent) or anti-c-myc (1:500, Sigma Aldrich) antibody overnight at 4° C. Cells were washed three times with PBS+0.1% Triton X-100 followed by incubation with Alexafluor 488 conjugated anti-mouse secondary antibody (1:500, Life technologies) and Hoechst 33258 (1:2500, Life technologies) at room temperature for 2 h. Cells were washed again and images were captured using Nikon Digital Sight microscope.

Example 8: *Drosophila* Genetics

UAS-yki$^{PD}$ construct was generated by cloning the yki single WW domain isoform (Yki-PD) cDNA into the pUAST vector. UAS-sd$^{WT}$ and UAS-sd$^{2CS}$ constructs were generated by cloning wild-type scalloped (sd) or sd palmitoylation-deficient (2CS) mutant cDNA into the pUAST-attB vectors. UAS-yki$^{PD}$ transgenic fly was created by conventional transposon-mediated transformation. UAS-sd$^{WT}$ and UAS-sd$^{2CS}$ transgenic flies were created by phiC31-mediated site-specific transformation, using the attP2 site at 51 C. GMR-Gal4 was used for overexpression analysis. All crosses were done at 25° C. The quantification of fly eyes were carried out by analyzing the eye area in the images, and normalized to the control wild type flies. n=10 for each genotypes. The qRT-PCR analysis of Diap-1 and Expanded was carried out using primer sequences previously reported. See Sorrentino, G. et al., *Nat. Cell. Biol.* 2014, 16, 357-366.

Example 9: Protein Purification and Crystallization

The cDNA encoding human TEAD2 (residues 217-447, TEAD2$^{217-447}$) was cloned into a pET29 vector (EMD Biosciences) that included a C-terminal His$_6$-tag. The construct was verified by DNA sequencing. The pET29-TEAD2$^{217-447}$ plasmid was transformed into the *E. coli* strain BL21(DE3)-T1$^R$ cells (Sigma) for protein expression. His$_6$-tagged TEAD2$^{217-447}$ was purified with Ni$^{2+}$-NTA agarose resin (Qiagen) and then purified by anion exchange chromatography with a resource-Q column followed by size exclusion chromatography with a Superdex 75 column (GE Healthcare). Purified TEAD2$^{217-447}$ was concentrated to 4 mg/ml in a buffer containing 20 mM Tris (pH 8.0), 100 mM NaCl, 2 mM MgCl$_2$, 1 mM TCEP and 5% glycerol.

Crystals of TEAD2$^{217-447}$ were grown at 20° C. using the hanging-drop vapor-diffusion method with a reservoir solution containing 0.1 M Hepes (pH 7.2) and 2.4 M sodium formate. The crystals were cryo-protected with reservoir solution supplemented with 25% glycerol and then flash-cooled in liquid nitrogen.

Example 10: In Vitro Palmitoylation

Recombinant GST-TEAD2 or His$_6$TEAD2 (500 ng) protein was incubated with the indicated concentrations of alkyne palmitoyl-CoA (Cayman Chemical) for 2 h or the indicated time in 50 mM MES, pH 6.4. The reaction was quenched with 1% SDS followed by Click reaction as described previously. Samples were analyzed by SDS-PAGE and streptavidin HRP. Bands intensity obtained from streptavidin blot were quantified using Image J (NIH) and the rate of palmitoylation in arbitrary unit was plotted against the concentration of palmitoyl-CoA. The data was fitted to the Michaelis-Menten equation using Prism v.6.0 (GraphPad). For mass spectrometry analysis, recombinant TEAD2 YBD (1 mg/ml) was incubated with 1 eq. of palmitoyl-CoA for 30 min at room temperature in a buffer containing 50 mM MES, pH 6.4.

Example 11: In Vitro Palmitoylation Assay to Measure the Potency of Compounds as TEAD Palmitoylation Inhibitors Recombinant His$_6$TEAD2 (500 ng) protein was incubated with DMSO control or TEAD inhibitors (MGH-CP1 and its analogues) at 5 μM for 30 min. 3 μM of alkyne palmitoyl-CoA (Cayman Chemical) were then added into the reaction mixture and incubated for 2 h in 50 mM MES, pH 6.4. The reaction was quenched with 1% SDS followed by Click reaction with biotin-azide. Samples were analyzed by SDS-PAGE and streptavidin HRP. Bands intensity obtained from streptavidin blot were quantified using Image J (NIH), and normalized to DMSO control. The percentage of inhibition was determined by comparing to DMSO control and non-palmitoylated TEAD2. To determine the dose-dependency of the inhibitors, various concentrations of the compounds (10 nM to 20 μM) were incubated with TEAD2 protein for 30 min, and then 3 μM of alkyne palmitoyl-CoA (Cayman Chemical) were then added into the reaction mixture and incubated for 2 h in 50 mM MES, pH 6.4. The reaction was then quenched and analyzed similarly as descried above. The level of palmitoylation was then determined by the streptavidin blot, and plotted by Prism to determine the IC$_{50}$ values.

Example 12: Cell Proliferation Assay

Human cancer cell lines (HuH7, JHH7), transformed MCF10A-YAP and mouse Lats1/2 DKO cells were cultured in 5% FBS containing media. The cells were seeded into 96-well plate with 500 cells/well. Various concentrations of compounds (10 nM to 20 μM) or DMSO control were added into the wells. The cells were further incubated for 2-5 days. The cell viability is determined by using CellTiter Glo (Promega). The data were then normalized with DMSO control and plotted in Prism software Human melanoma cell A375 and dermal fibroblasts are control cells and are tested similarly.

Example 13: Cell Based YAP-Reporter Assay

HEK293A cells stably transfected with TEAD-binding element reporter construct (8xGTIIC-Luc) and YAP were used in the assay. Cells are seeded in 384-well plates at 1000 cells/well density. Various concentrations of compounds (10 nM to 20 μM) or DMSO control were added into the wells. The luciferase signal is measured using BrightGlo. The data were then normalized with DMSO control and plotted in Prism software.

Example 14: Data Collection and *Structure* Determination

Diffraction data were collected at beamline 19-ID (SBC-CAT) at the Advanced Photon Source (Argonne National Laboratory) at the wavelength of 0.9791 Å at 100 K and processed with HKL3000. Phases were obtained by molecular replacement with Phaser using the crystal structure of human TEAD2 (PDB code: 3L15) as the search model. Iterative model building and refinements were carried out with COOT and Phenix, respectively. MolProbity was used for structure validation to show that all models have good geometry. Data collection and structure refinement statistics are summarized in Table 1 below. Ramachandran statistics (Favored/allowed/outlier (%)) are 97.4/2.6/0.0. The crystal structure of palmitate-bound TEAD1-YAP was obtained by building two thioester-linked palmitate molecules into TEAD1-YAP (PDB code: 3KYS) with COOT using the electron density map calculated from 3KYS structure factor. The final model was refined with Phenix.

TABLE 1

Data collection and refinement statistics (molecular replacement).

| | TEAD2$^{217\text{-}447}$-PLM | TEAD2$^{217\text{-}447}$-Compound 4 |
|---|---|---|
| Data collection | | |
| Space group | C2 | |
| Wavelength (Å) | 0.97915 | 0.97929 |
| Unit cell dimensions | | |
| a, b, c (Å) | 122.49, 61.15, 80.31 | 122.46, 61.64, 80.42 |
| α, β, γ (°) | 90.00, 117.17, 90.00 | 90.00, 117.17, 90.00 |
| Resolution (Å)* | 40.00-2.04 (2.08-2.04) | 40.00-2.32 (2.36-2.32) |
| $R_{merge}$ (%)* | 5.5 (50.8) | 6.1 (78.7) |
| I/σI* | 26.3 (2.36) | 21.1 (1.7) |
| Completeness (%)* | 95.9 (87.0) | 98.3 (100.0) |
| Redundancy* | 4.0 (3.6) | 4.1 (4.2) |

TABLE 1-continued

Data collection and refinement statistics (molecular replacement).

| | TEAD2$^{217\text{-}447}$-PLM | TEAD2$^{217\text{-}447}$-Compound 4 |
|---|---|---|
| Refinement statistics | | |
| Resolution (Å)* | 36.1-2.05 (2.12-2.05) | 38.85-2.32 (2.44-2.32) |
| No. reflections | 28795 | 19627 |
| $R_{work}/R_{free}$ | 18.2/22.8 | 19.8 (21.9) |
| No. atoms | | |
| Protein | 3308 | 3294 |
| Ligand/ion | 36 | 66 |
| Water | 155 | 52 |
| B-factors (Å$^2$) | | |
| Protein | 38.4 | 41.3 |
| Ligand/ion | 27.1 | 34.7 |
| Water | 41.6 | 74.3 |
| R.m.s. deviations | | |
| Bond lengths (Å) | 0.014 | 0.003 |
| Bond angles (°) | 1.41 | 0.79 |

Figure 22:
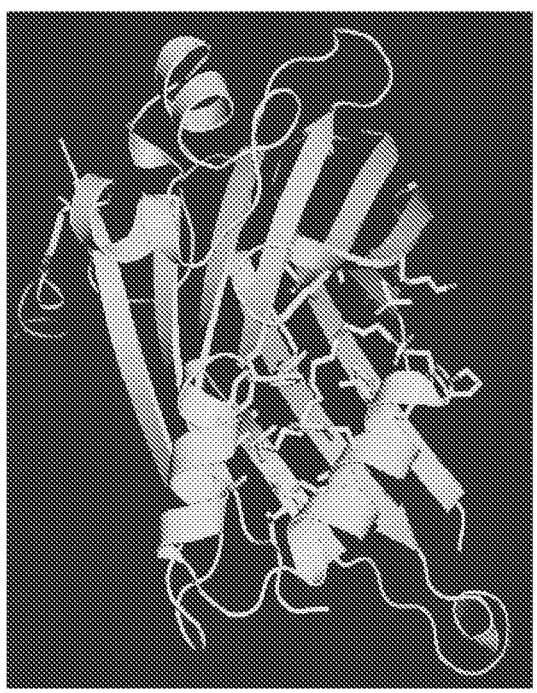
FIG. 22 is a pair of ribbon diagrams showing the co-crystal structures of palmitate and compound (4) ("MGH-CP-1") bound to TEAD-2.
Figure 22:
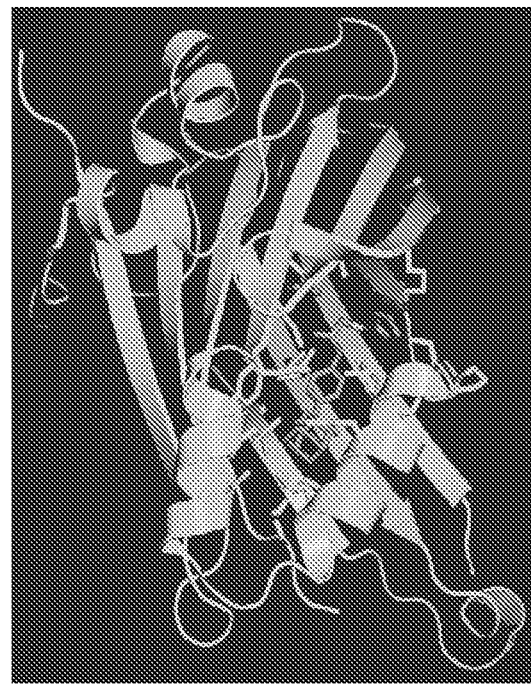

*Highest-resolution shell is shown in parentheses.
A co-crystal structure shows that compound (4) ("MGH-CP-1") binds to TEAD2 in the lipid binding pocket that would be occupied by palimitate (FIG. 22).

Example 15: Compounds Active as TEAD Palmitoylation Inhibitors

Compounds (4) to (53) were tested for activity in inhibiting TEAD palmitoylation in the assay of Example 11. The data for the compounds provided in Table 2 as a percentage of inhibition of TEAD2 palmitoylation by the compound at a concentration of 5 μM.

TABLE 2

Activity of Compounds as TEAD Palmitoylation Inhibitors

| Compound structure | Molecular Weight | % of inhibition of TEAD2 palmitoylation at 5 μM |
|---|---|---|
| (4) | 368.5 | 85 |
| (5) | 366.5 | 30 |
| (6) | 276.4 | 24 |

TABLE 2-continued

Activity of Compounds as TEAD Palmitoylation Inhibitors

| Compound structure | Molecular Weight | % of inhibition of TEAD2 palmitoylation at 5 μM |
|---|---|---|
| (7) | 553.5 | 80 |
| (8) | 537.5 | 70 |
| (9) | 567.5 | 10 |
| (10) | 574.5 | 10 |
| (11) | 382.5 | 10 |
| (12) | 310.3 | 89 |
| (13) | 324.4 | 23 |

TABLE 2-continued

Activity of Compounds as TEAD Palmitoylation Inhibitors

| Compound structure | Molecular Weight | % of inhibition of TEAD2 palmitoylation at 5 μM |
|---|---|---|
| (14) | 461.4 | 12 |
| (15) | 447.3 | 87 |
| (16) | 360.4 | 90 |
| (17) | 389.2 | 89 |
| (18) | 410.5 | 56 |
| (19) | 392.5 | 93 |
| (20) | 446.3 | 95 |

TABLE 2-continued
Activity of Compounds as TEAD Palmitoylation Inhibitors
| Compound structure | Molecular Weight | % of inhibition of TEAD2 palmitoylation at 5 μM |
|---|---|---|
| 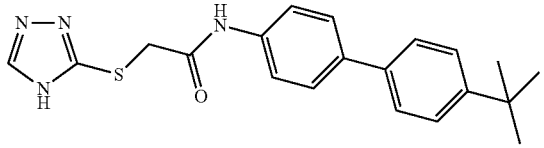 (21) | 366.5 | 100 |
| 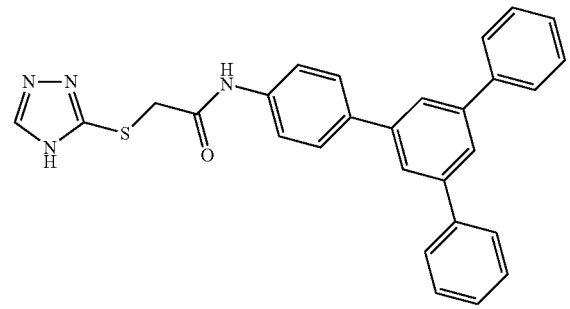 (22) | 462.5 | 68 |
| 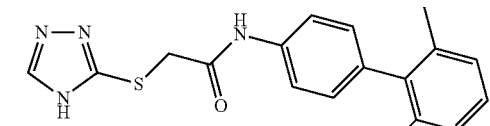 (23) | 338.4 | 100 |
| 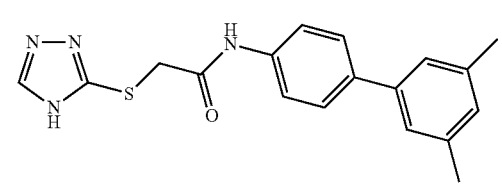 (24) | 338.4 | 100 |
| 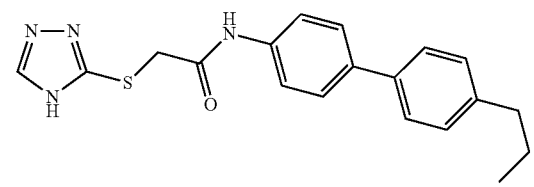 (25) | 352.4 | 97 |
| 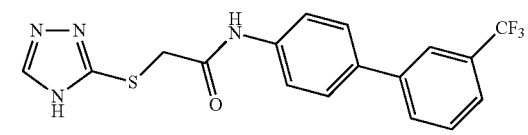 (26) | 378.3 | 88 |

TABLE 2-continued

Activity of Compounds as TEAD Palmitoylation Inhibitors

| Compound structure | Molecular Weight | % of inhibition of TEAD2 palmitoylation at 5 μM |
|---|---|---|
| (27) | 386.4 | 70 |
| (28) | 400.1 | <10 |
| (29) | 351.4 | 45 |
| (30) | 382.5 | 100 |
| (31) | 385.5 | 68 |
| (32) | 369.5 | 39 |
| (33) | 478 | 40 |
| (34) | 459.2 | 53 |

TABLE 2-continued

Activity of Compounds as TEAD Palmitoylation Inhibitors

| Compound structure | Molecular Weight | % of inhibition of TEAD2 palmitoylation at 5 µM |
|---|---|---|
| (35) | 508 | 47 |
| (36) | 351 | 38 |
| (37) | 396 | 100 |
| (38) | 473 | 80 |
| (39) | 383 | 76 |
| (40) | 397 | 80 |
| (41) | 513 | 56 |

TABLE 2-continued
Activity of Compounds as TEAD Palmitoylation Inhibitors
| Compound structure | Molecular Weight | % of inhibition of TEAD2 palmitoylation at 5 μM |
|---|---|---|
| 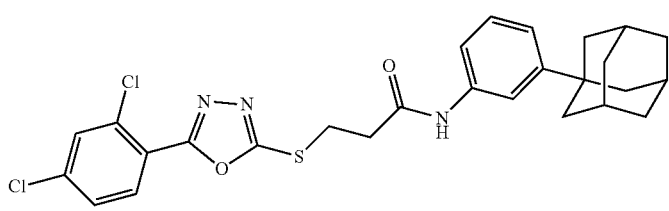 (42) | 528 | 63 |
| 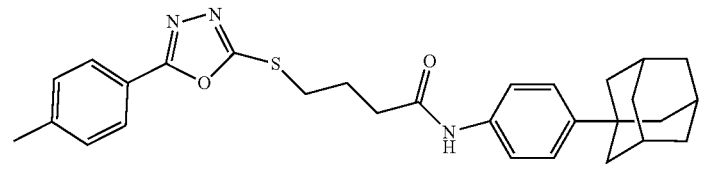 (43) | 487 | 58 |
| 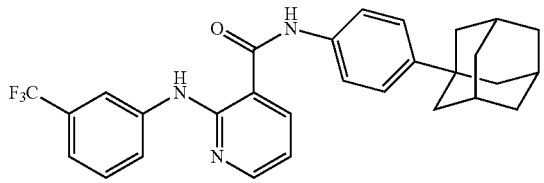 (44) | 491 | <10 |
| 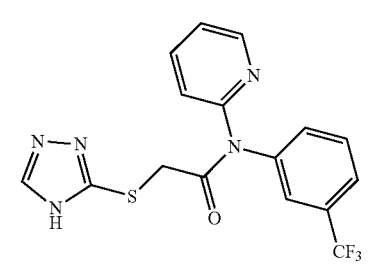 (45) | 379 | <10 |
| 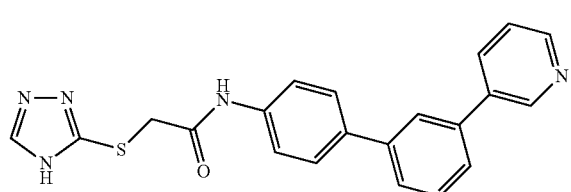 (46) | 387 | 100 |
| 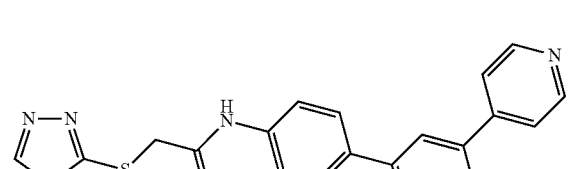 (47) | 387 | 100 |

TABLE 2-continued
Activity of Compounds as TEAD Palmitoylation Inhibitors
| Compound structure | Molecular Weight | % of inhibition of TEAD2 palmitoylation at 5 μM |
|---|---|---|
| 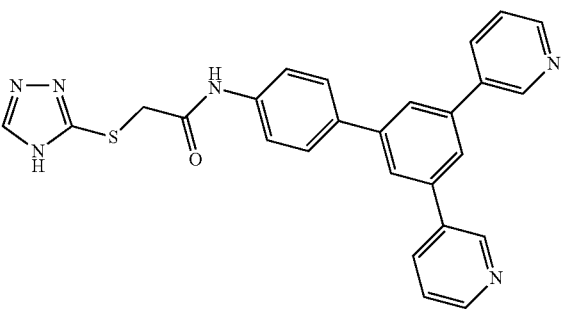<br>(48) | 464 | 95 |
| 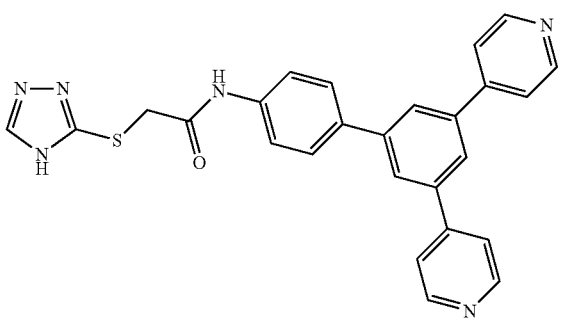<br>(49) | 464 | 90 |
| 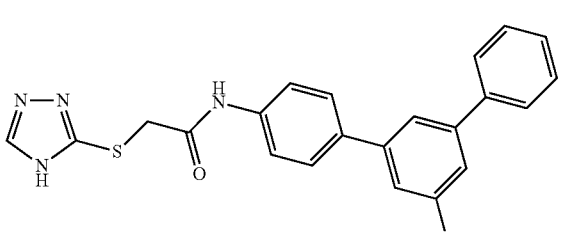<br>(50) | 454 | 90 |
| 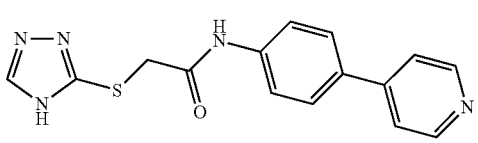<br>(51) | 311 | 90 |
| 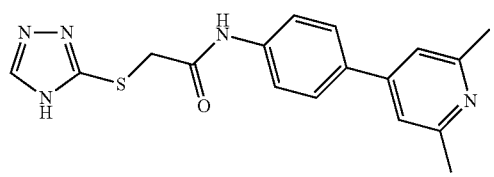<br>(52) | | 95 |

TABLE 2-continued

Activity of Compounds as TEAD Palmitoylation Inhibitors

| Compound structure | Molecular Weight | % of inhibition of TEAD2 palmitoylation at 5 µM |
|---|---|---|
| 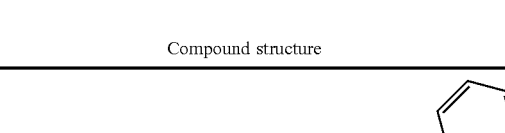 (53) | 463 | 78 |

Figure 23:
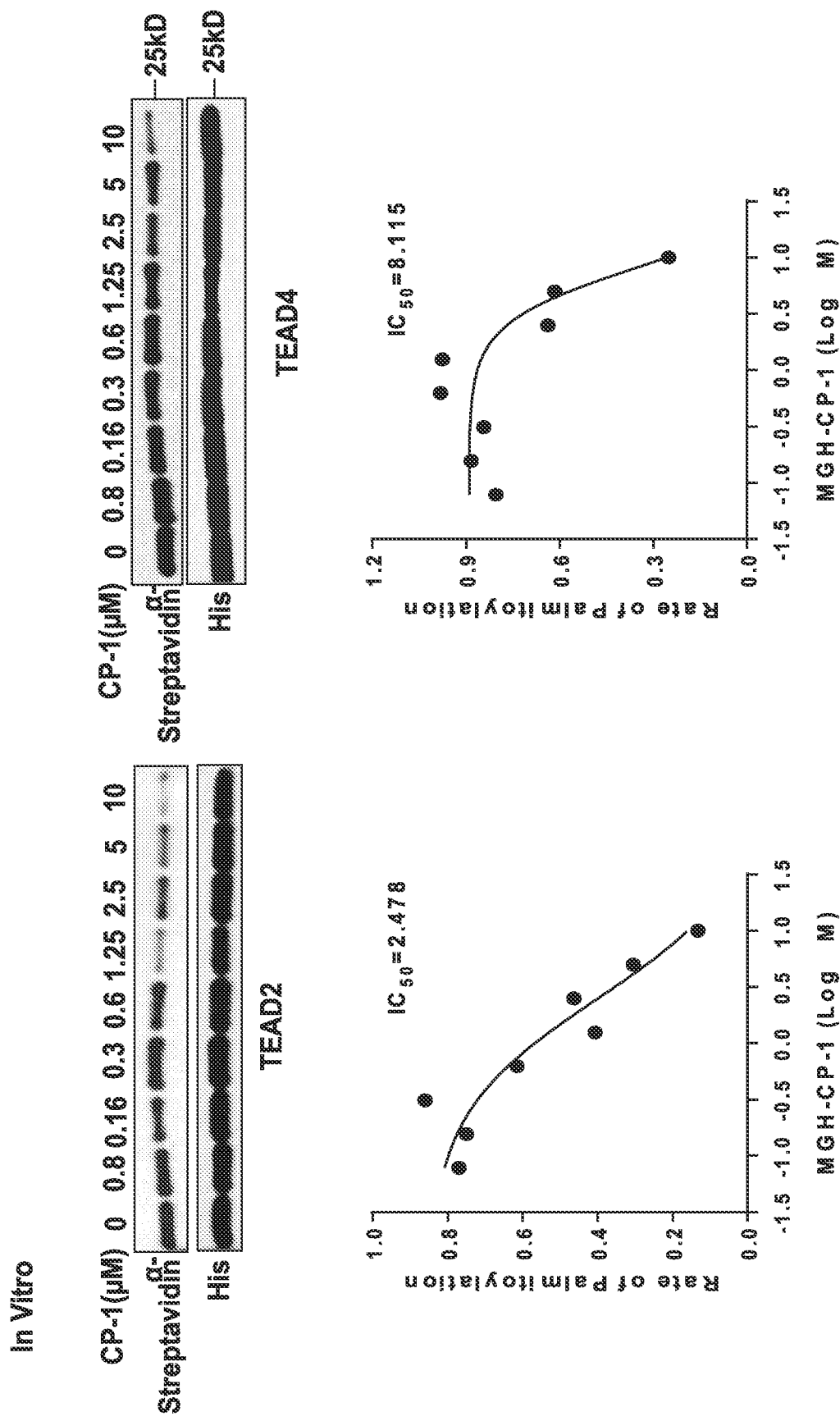
FIG. 23 is a set of blots and corresponding plots showing inhibition of TEAD2 and TEAD4 palmitoylation by compound (4) ("CP-1").

Example 16: Inhibition of Palmitoylation of TEAD2 and TEAD4 by Compound (4) In Vitro Assays were performed to measure inhibition of TEAD2 and TEAD4 palmitoylation in vitro using purified TEAD2 and TEAD4 proteins and 1 µM of alkyne-palmitoyl-CoA. Compound (4) ("CP-1") was tested at concentrations in the range from 0 to 10 µM and the amount of palmitoylation was quantified. The results are shown in FIG. 23 and show that compound (4) dose-dependently inhibited palmitoylation of both TEAD2 and TEAD4 in vitro.

Figure 24:
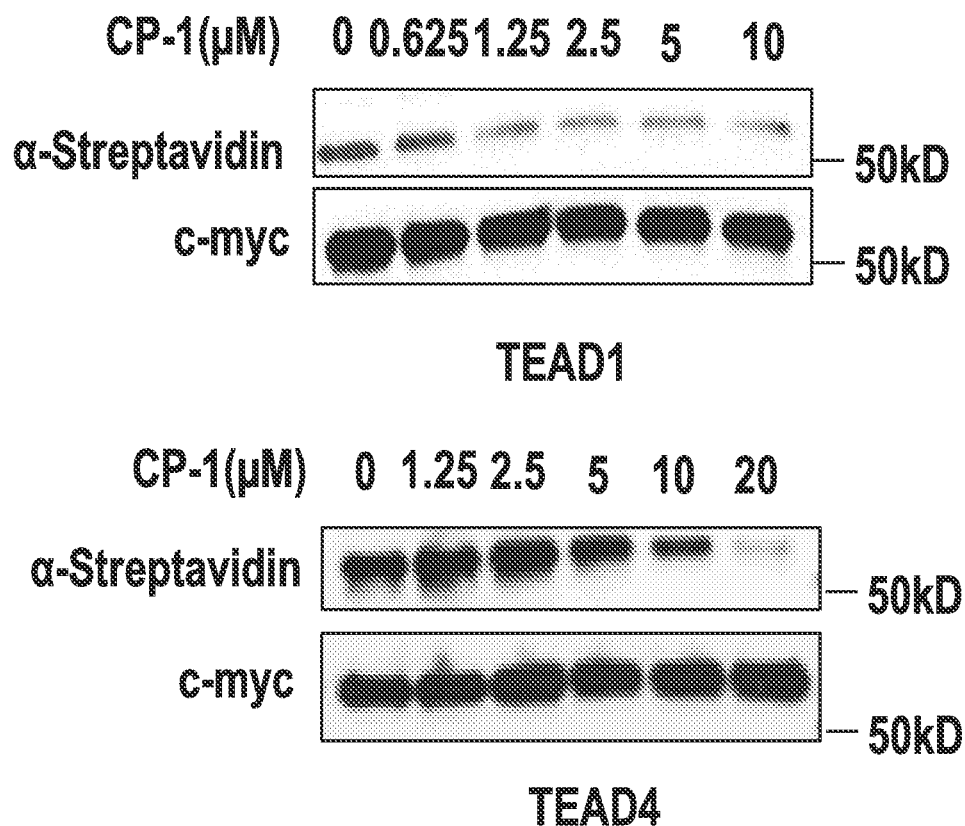
FIG. 24 is a set of blots showing inhibition of TEAD1 and TEAD4 palmitoylation in cells by compound (4) ("CP-1").

Example 17: Inhibition of Palmitoylation of TEAD2 and TEAD4 by Compound (4) in Cells Assays were performed to measure inhibition of TEAD1 and TEAD4 palmitoylation in cells that were transfected with TEAD1 and TEAD4 proteins and labelled with 1 µM of alkyne-palmitic acid probe. The ability of compound (4) ("CP-1") to inhibit palmitoylation was tested at concentrations in the range from 0 to 10 µM and the amount of palmitoylation was quantified. The results are shown in FIG. 24 and show that compound (4) dose-dependently inhibited palmitoylation of both TEAD1 and TEAD4 in cells.

Example 18: Co-Immunoprecipitation of TEAD4 and YAP

Figure 25:
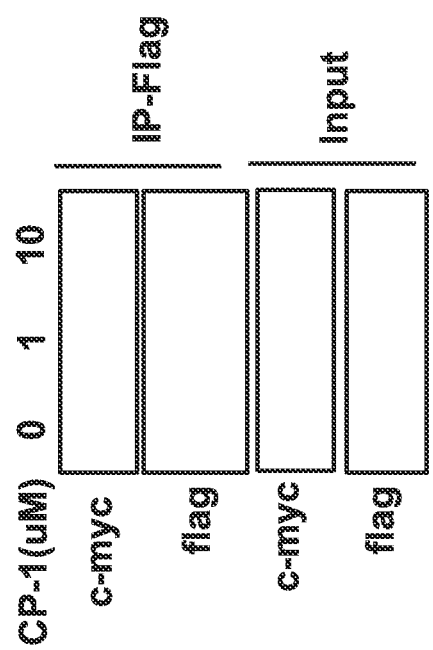
FIG. 25 is a set of blots showing inhibition of the TEAD4-YAP interaction by compound (4) ("CP-1") in a co-immunoprecipitation assay.

Co-immunoprecipitation assays of TEAD4 and YAP were performed. The ability of compound (4) ("CP-1") to inhibit to inhibit the TEAD4-YAP interaction was tested at concentrations in the range from 0 to 10 µM. The results are shown in FIG. 25 and show that compound (4) dose-dependently inhibited the interaction of TEAD4 with YAP.

Example 19: Co-Immunoprecipitation of TEAD1 and Vgll4

Figure 26:
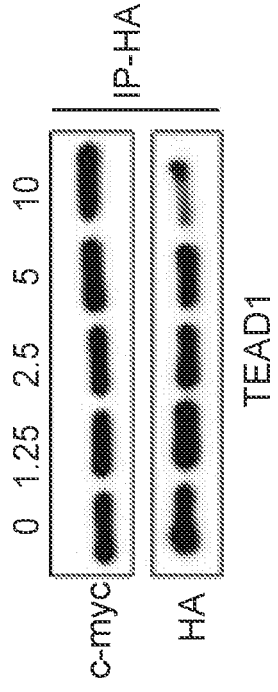
FIG. 26 is a set of blots showing that the TEAD4-Vgll4 interaction is not inhibited by compound (4) ("CP-1").

Co-immunoprecipitation assays of TEAD1 and Vgll4 were performed. The ability of compound (4) ("CP-1") to inhibit to inhibit the TEAD1-Vgll4 interaction was tested at concentrations in the range from 0 to 10 µM. The results are shown in FIG. 26 and show that compound (4) did not affect the interaction of TEAD1 with Vgll4.

Figure 27:
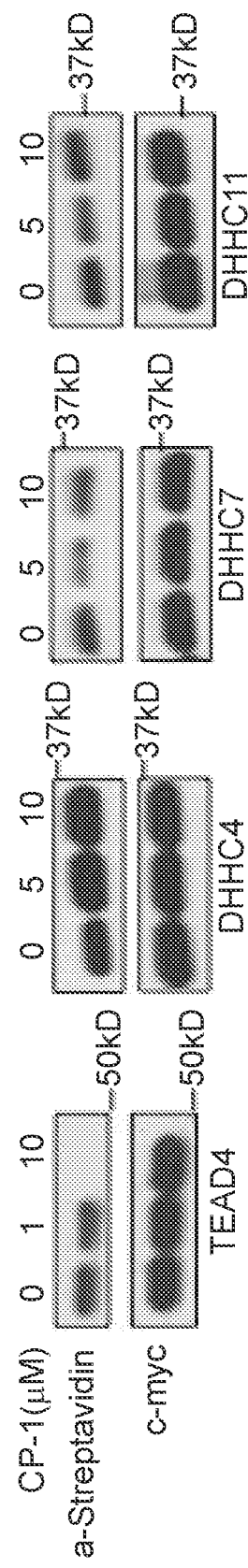
FIG. 27 is a set of blots showing that compound (4) ("CP-1") is effective to inhibit TEAD4 but does not inhibit other palmitoyl acyltransferases (ZDHHC proteins).

Example 20: Selectivity of Compound (4) in Inhibiting TEAD4 Palmitoylation Versus Other Palmitoyl Acyltransferases Assays were performed to measure inhibition of TEAD4 palmitoylation compared with other palmitoyl acyltransferses, DHHC4, DHHC7 and DHHC11. The ability of compound (4) ("CP-1") to inhibit palmitoylation was tested at concentrations in the range from 0 to 10 µM and the amount of palmitoylation was quantified. The results are shown in FIG. 27 and show that compound (4) dose-dependently inhibited palmitoylation of both TEAD4 but did not inhibit palmitoylation with the other palmitoyl acyltransferses.

Example 21: Inhibition of Cancer Cell Proliferation and Colony Formation by Compound (4)

Assays were performed to measure inhibition of cancer cell proliferation by compound (4). The ability of compound (4) ("CP-1") to inhibit proliferation cell proliferation in the human hepatocellular carcinoma cell lines HuH7 and JHH7, and in the breast cancer cell line MDA-MB-453. The compound was also tested against the SK-HEP-1 (adenocarcinoma), BT-474 (breast tumor), OCUB-M (breast carcinoma), HCC1143 (ductal carcinoma), EVSA-T (ductal carcinoma) and BT-20 (breast carcinoma) cell lines.

Figure 28:
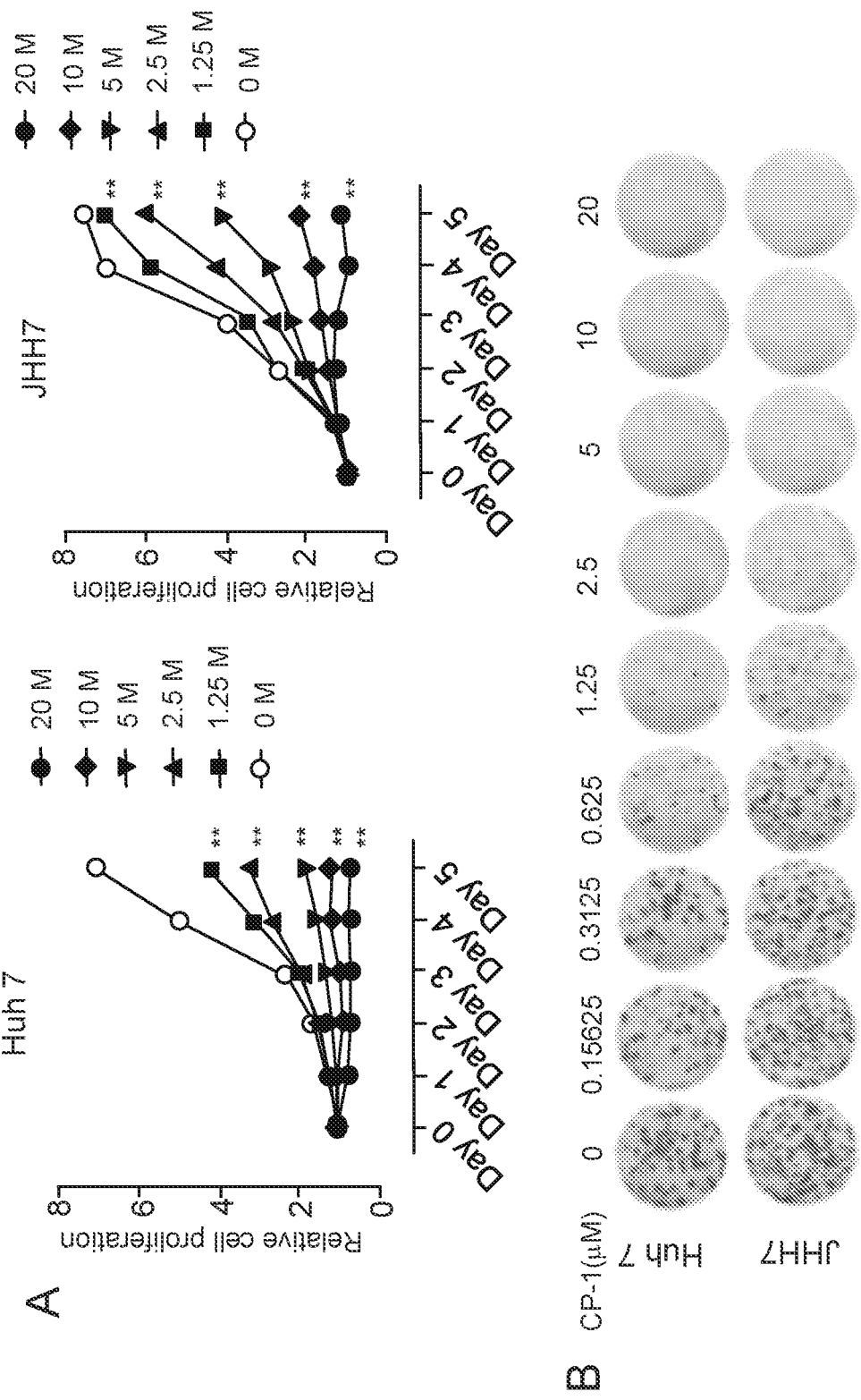
FIG. 28 is a set of blots and photographs. Panel A: plots showing that compound (4) ("CP-1") dose-dependently inhibits human hepatocellular carcinoma cell line HuH7 and JHH7 proliferation. Panel B: photographs showing that compound (4) inhibits colony formation of HuH7 and JHH7 cells. Panel C: plots showing that compound (4) inhibits HuH7 cell proliferation with an $IC_{50}$ of 1.6 µM; Panel D: plots showing that compound (4) inhibits breast cancer cell line MDA-MB-453 with IC50 of 0.4 µM. Panel E: plots showing that compound (4) inhibits YAP target gene expression in HuH7 cells. Panel F: plots showing that compound (4) inhibits YAP target genes in MDA-MB-453 cells. Panels G and H: plots showing that compound (4) inhibits proliferation of YAP dependent cell lines but is less effective at inhibiting proliferation of YAP-independent HCC and breast cancer cell lines.
Figure 28:
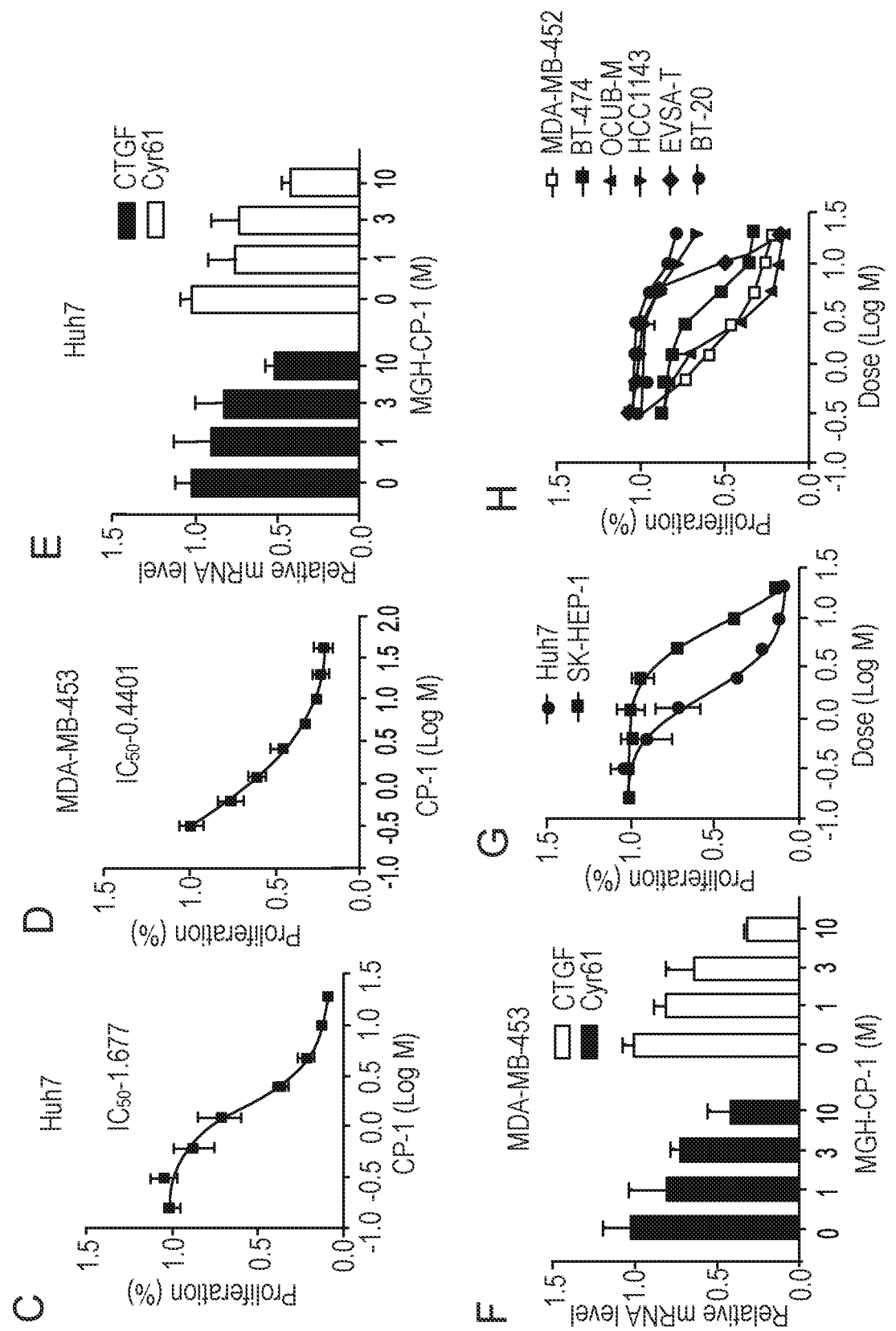

Results are shown in FIG. 28. The plots in Panel A show that compound (4) ("CP-1") dose-dependently inhibits human hepatocellular carcinoma cell line HuH7 and JHH7 proliferation. The photographs in Panel B shows that compound (4) inhibits colony formation of HuH7 and JHH7 cells. The plots in panels C to H show that: (C) compound (4) inhibits HuH7 cell proliferation with an $IC_{50}$ of 1.6 µM; (D) compound (4) inhibits breast cancer cell line MDA-MB-453 with IC50 of 0.4 µM; (E) compound (4) inhibits YAP target gene expression in HuH7 cells; (F) compound (4) inhibits YAP target genes in MDA-MB-453 cells. (G)-(H) compound (4) inhibits proliferation of YAP dependent cell lines but is less effective at inhibiting proliferation of YAP-independent HCC and breast cancer cell lines.

Example 21: Inhibition of Cancer Cell Colony Formation by Compounds (4), (22) and (36)

Assays were performed to measure inhibition of cancer cell proliferation in HuH7 cells by compounds (4), (22) and (36), which were each tested at 0-20 µM.

Figure 29:
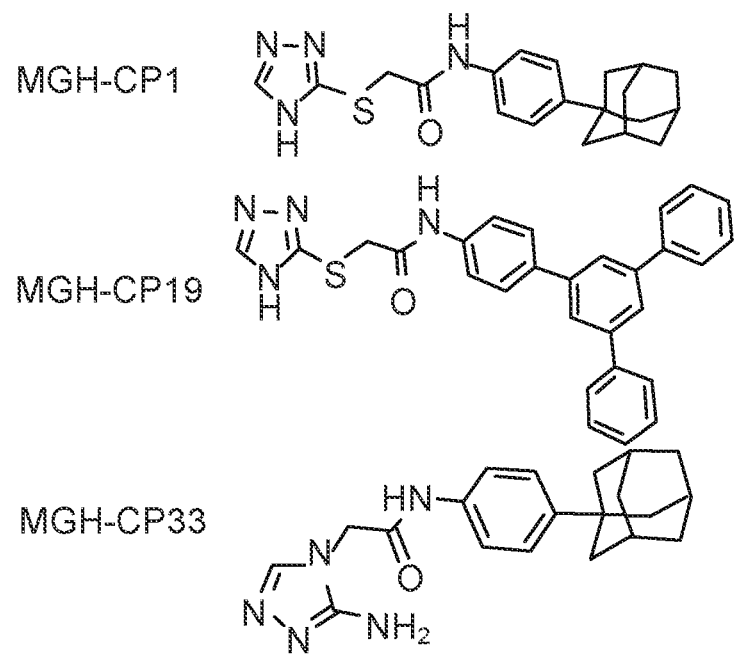
FIG. 29 is a set of photographs showing inhibition of HuH7 cancer cell colony formation by compounds (4), (22) and (36).
Figure 29:
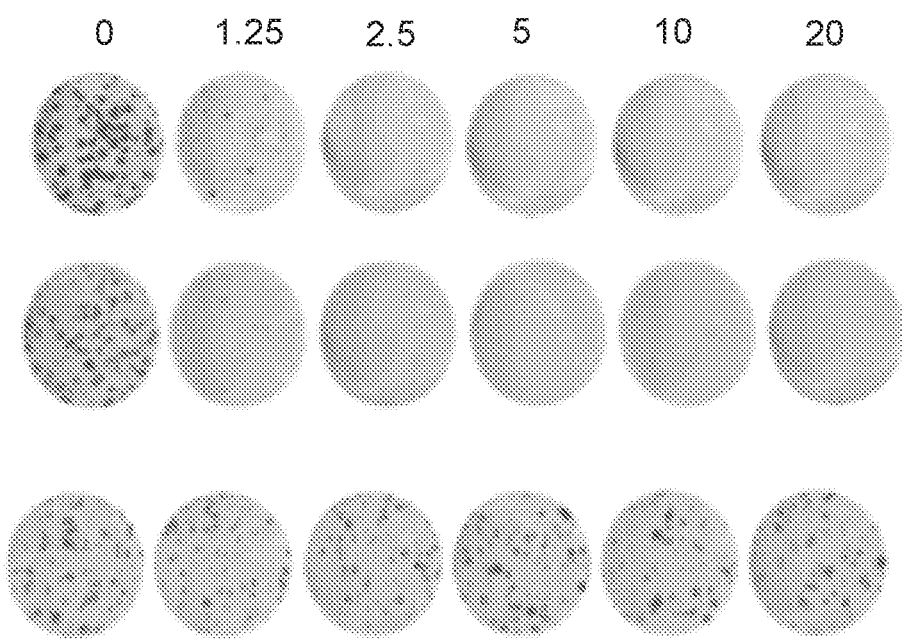

Results are shown in FIG. 29. The results show that compounds (4) ("MGH-CP1") and (23) ("MGH-CP19") are effective to inhibit cancer cell proliferation in HuH7 cells. Compound (36) ("MGH-CP33"), which displays lower inhibition of TEAD2 palmitoylation, is less effective.

REFERENCES

1. Harvey, K. F., Zhang, X. & Thomas, D. M. The Hippo pathway and human cancer. *Nature reviews. Cancer* 13, 246-257 (2013).
2. Pan, D. Hippo signaling in organ size control. *Genes Dev* 21, 886-897 (2007).
3. Pan, D. The hippo signaling pathway in development and cancer. *Dev Cell* 19, 491-505 (2010).
4. Ota, M. & Sasaki, H. Mammalian Tead proteins regulate cell proliferation and contact inhibition as transcriptional mediators of Hippo signaling. *Development* 135, 4059-4069 (2008).
5. Wu, S., Liu, Y., Zheng, Y., Dong, J. & Pan, D. The TEAD/TEF family protein Scalloped mediates transcriptional output of the Hippo growth-regulatory pathway. *Dev Cell* 14, 388-398 (2008).
6. Zhao, B. et al. TEAD mediates YAP-dependent gene induction and growth control. *Genes & development* 22, 1962-1971 (2008).
7. Zhang, W. et al. VGLL4 functions as a new tumor suppressor in lung cancer by negatively regulating the YAP-TEAD transcriptional complex. *Cell Res* 24, 331-343 (2014).
8. Jiao, S. et al. A peptide mimicking VGLL4 function acts as a YAP antagonist therapy against gastric cancer. *Cancer Cell* 25, 166-180 (2014).
9. Johnson, R. & Halder, G. The two faces of Hippo: targeting the Hippo pathway for regenerative medicine and cancer treatment. *Nature reviews. Drug discovery* 13, 63-79 (2014).
10. Smotrys, J. E. & Linder, M. E. Palmitoylation of intracellular signaling proteins: regulation and function. *Annu Rev Biochem* 73, 559-587 (2004).
11. Roth, A. F. et al. Global analysis of protein palmitoylation in yeast. *Cell* 125, 1003-1013 (2006).
12. Wan, J., Roth, A. F., Bailey, A. O. & Davis, N. G. Palmitoylated proteins: purification and identification. *Nat Protoc* 2, 1573-1584 (2007).
13. Martin, B. R. & Cravat, B. F. Large-scale profiling of protein palmitoylation in mammalian cells. *Nat Methods* 6, 135-138 (2009).
14. Yount, J. S. et al. Palmitoylome profiling reveals S-palmitoylation-dependent antiviral activity of IFITM3. *Nat Chem Biol* 6, 610-614 (2010).
15. Resh, M. D. Trafficking and signaling by fatty-acylated and prenylated proteins. *Nat Chem Biol* 2, 584-590 (2006).
16. Fukata, Y. & Fukata, M. Protein palmitoylation in neuronal development and synaptic plasticity. *Nat Rev Neurosci* 11, 161-175 (2010).
17. Greaves, J. & Chamberlain, L. H. DHHC palmitoyl transferases: substrate interactions and (patho)physiology. *Trends Biochem Sci* 36, 245-253 (2011).
18. Kummel, D., Heinemann, U. & Veit, M. Unique self-palmitoylation activity of the transport protein particle component Bet3: a mechanism required for protein stability. *Proc Natl Acad Sci USA* 103, 12701-12706 (2006).
19. Duncan, J. A. & Gilman, A. G. Autoacylation of G protein alpha subunits. *J Biol Chem* 271, 23594-23600 (1996).
20. Yang, J. et al. Submicromolar concentrations of palmitoyl-CoA specifically thioesterify cysteine 244 in glyceraldehyde-3-phosphate dehydrogenase inhibiting enzyme activity: a novel mechanism potentially underlying fatty acid induced insulin resistance. *Biochemistry* 44, 11903-11912 (2005).
21. Resh, M. D. Use of analogs and inhibitors to study the functional significance of protein palmitoylation. *Methods* 40, 191-197 (2006).
22. Zheng, B. et al. 2-Bromopalmitate analogues as activity-based probes to explore palmitoyl acyltransferases. *J Am Chem Soc* 135, 7082-7085 (2013).
23. Zheng, B., Zhu, S. & Wu, X. Clickable analogue of cerulenin as chemical probe to explore protein palmitoylation. *ACS Chem Biol* 10, 115-121 (2015).
24. Hannoush, R. N. Profiling cellular myristoylation and palmitoylation using omega-alkynyl fatty acids. *Methods Mol Biol* 800, 85-94 (2012).
25. Hang, H. C. & Linder, M. E. Exploring protein lipidation with chemical biology. *Chem Rev* 111, 6341-6358 (2011).
26. Liu-Chittenden, Y. et al. Genetic and pharmacological disruption of the TEAD-YAP complex suppresses the oncogenic activity of YAP. *Genes & development* 26, 1300-1305 (2012).
27. Tian, W., Yu, J., Tomchick, D. R., Pan, D. & Luo, X. Structural and functional analysis of the YAP-binding domain of human TEAD2. *Proc Natl Acad Sci USA* 107, 7293-7298 (2010).
28. Jennings, B. C. & Linder, M. E. DIAIIC protein S-acyltransferases use similar ping-pong kinetic mechanisms but display different acyl-CoA specificities. *J Biol Chem* 287, 7236-7245 (2012).
29. Faergeman, N. J. & Knudsen, J. Role of long-chain fatty acyl-CoA esters in the regulation of metabolism and in cell signalling. *Biochem J* 323 (Pt1), 1-12 (1997).
30. Noland, C. L. et al. Palmitoylation of TEAD Transcription Factors Is Required for Their Stability and Function in Hippo Pathway Signaling. *Structure* 24, 1-8 (2016).
31. Li, Z. et al. Structural insights into the YAP and TEAD complex. *Genes & development* 24, 235-240 (2010).
32. Chen, L. et al. Structural basis of YAP recognition by TEAD4 in the hippo pathway. *Genes Dev* 24, 290-300 (2010).
33. Zhou, Z. et al. Targeting Hippo pathway by specific interruption of YAP-TEAD interaction using cyclic YAP-like peptides. *Faseb J* 29, 724-732 (2015).
34. Ismail, S. A. et al. Arl2-GTP and Arl3-GTP regulate a GDI-like transport system for farnesylated cargo. *Nat Chem Biol* 7, 942-949 (2011).
35. Zhang, H. et al. Photoreceptor cGMP phosphodiesterase delta subunit (PDEdelta) functions as a prenyl-binding protein. *J Biol Chem* 279, 407-413 (2004).
36. Chandra, A. et al. The GDI-like solubilizing factor PDEdelta sustains the spatial organization and signalling of Ras family proteins. *Nat Cell Biol* 14, 148-158 (2012).
37. Dupont, S. et al. Role of YAP/TAZ in mechanotransduction. *Nature* 474, 179-183 (2011).
38. Nagar, B. et al. Structural basis for the autoinhibition of c-Abl tyrosine kinase. *Cell* 112, 859-871 (2003).
39. Hantschel, O. et al. A myristoyl/phosphotyrosine switch regulates c-Abl. *Cell* 112, 845-857 (2003).
40. Benhaddou, A. et al. Transcription factor TEAD4 regulates expression of myogenin and the unfolded protein response genes during C2C12 cell differentiation. *Cell Death Differ* 19, 220-231 (2012).
41. Yang, Z. et al. Screening with a novel cell-based assay for TAZ activators identifies a compound that enhances myogenesis in C2C12 cells and facilitates muscle repair in a muscle injury model. *Mol Cell Biol* 34, 1607-1621 (2014).
42 Park, G. H. et al. Novel TAZ modulators enhance myogenic differentiation and muscle regeneration. *Br J Pharmacol* 171, 4051-4061 (2014).
43 Koontz, L. M. et al. The Hippo effector Yorkie controls normal tissue growth by antagonizing scalloped-mediated default repression. *Dev Cell* 25, 388-401 (2013).
44 Turnbull, A. P. et al. Structure of palmitoylated BET3: insights into TRAPP complex assembly and membrane localization. *Embo J* 24, 875-884 (2005).
45 Pobbati, A. V. et al. Targeting the Central Pocket in Human Transcription Factor TEAD as a Potential Cancer Therapeutic Strategy. *Structure* 23, 2076-2086 (2015).
46 Menendez, J. A. & Lupu, R. Fatty acid synthase and the lipogenic phenotype in cancer pathogenesis. *Nat Rev Cancer* 7, 763-777 (2007).
47 Chan, S. W., Lim, C. J., Guo, K., Ng, C. P., Lee, I., Hunziker, W., Zeng, Q., and Hong, W. (2008). A role for TAZ in migration, invasion, and tumorigenesis of breast cancer cells. Cancer Res 68, 2592-2598.
48. Fitamant, J., Kottakis, F., Benhamouche, S., Tian, H. S., Chuvin, N., Parachoniak, C. A., Nagle, J. M., Perera, R. M., Lapouge, M., Deshpande, V., et al. (2015). YAP Inhibition Restores Hepatocyte Differentiation in Advanced HCC, Leading to Tumor Regression. *Cell reports*.
49. Kim, M., Kim, M., Lee, S., Kuninaka, S., Saya, H., Lee, H., Lee, S., and Lim, D. S. (2013). cAMP/PKA signalling reinforces the LATS-YAP pathway to fully suppress YAP in response to actin cytoskeletal changes. Embo J 32, 1543-1555.
50. Mohseni, M., Sun, J., Lau, A., Curtis, S., Goldsmith, J., Fox, V. L., Wei, C., Frazier, M., Samson, O., Wong, K. K., et al. (2014). A genetic screen identifies an LKB1-MARK signalling axis controlling the Hippo-YAP pathway. Nat Cell Biol 16, 108-117.
51. Nguyen, H. B., Babcock, J. T., Wells, C. D., and Quilliam, L. A. (2012). LKB1 tumor suppressor regulates AMP kinase/mTOR-independent cell growth and proliferation via the phosphorylation of Yap. Oncogene Published online October 3rd, 10.1038/onc.2012.1431.
52. Zhou, D., Conrad, C., Xia, F., Park, J. S., Payer, B., Yin, Y., Lauwers, G. Y., Thasler, W., Lee, J. T., Avruch, J., et al. (2009). Mst1 and Mst2 maintain hepatocyte quiescence and suppress hepatocellular carcinoma development through inactivation of the Yap1 oncogene. Cancer Cell 16, 425-438.
53. Sorrentino, G. et al., Metabolic control of YAP and TAZ by the mevalonate pathway. Nat. Cell. Biol., 2014, 16, 357-366.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A compound of one of the following formulae:

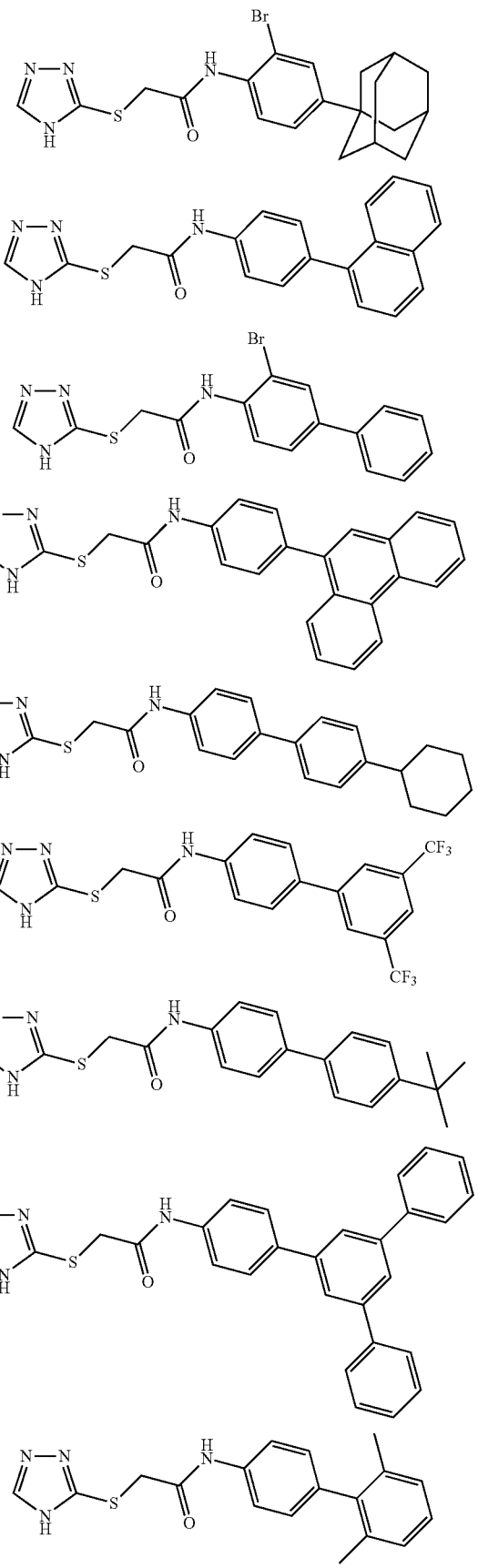

-continued

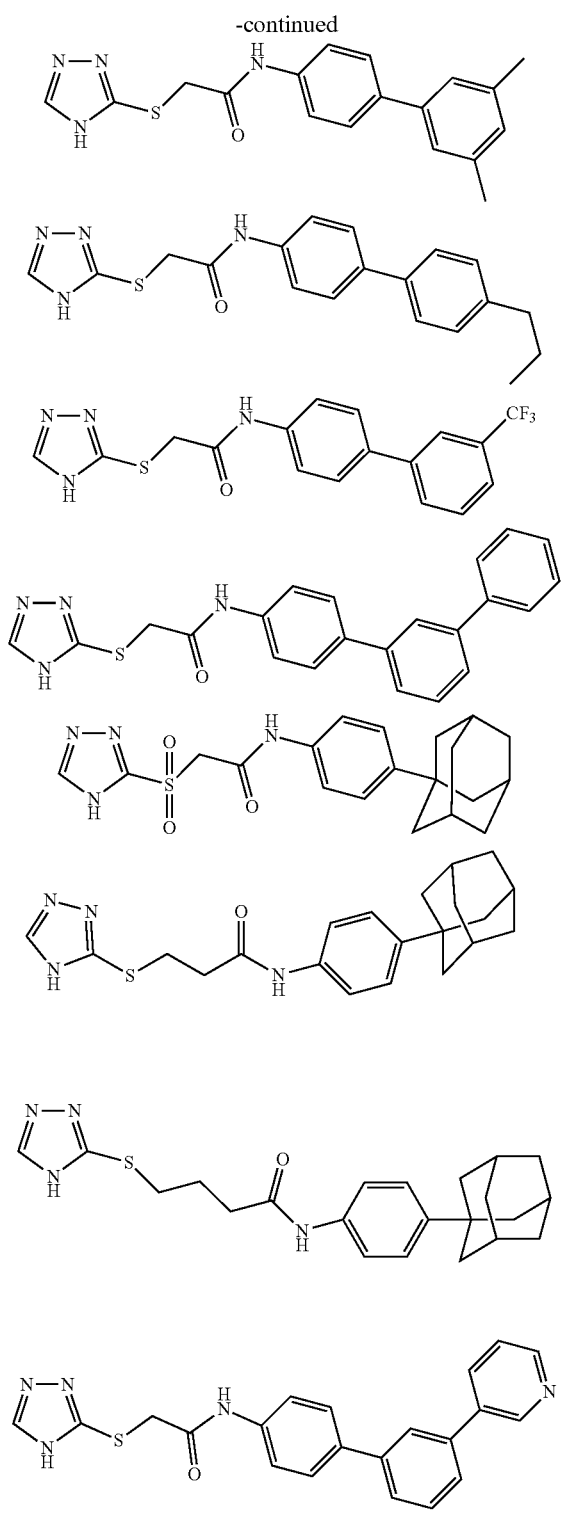

-continued

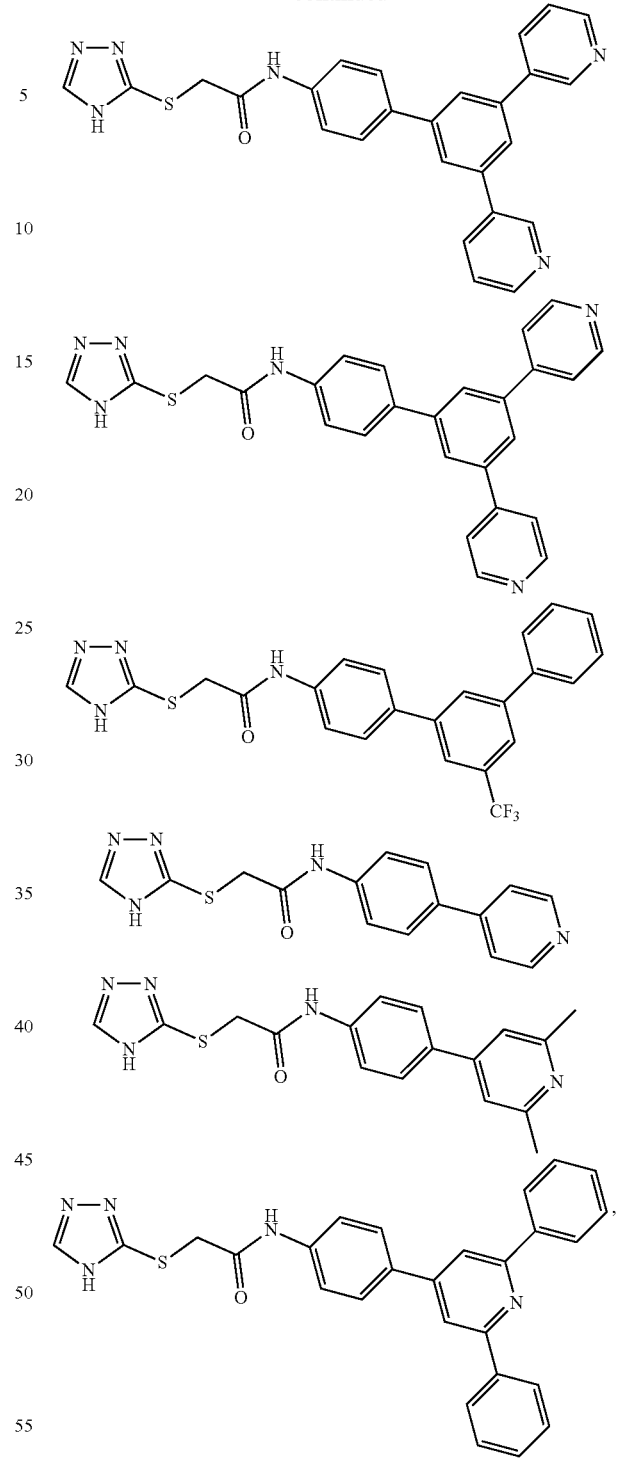

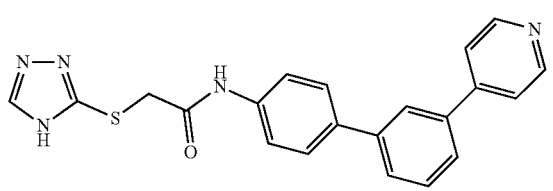

or a pharmaceutically acceptable salt thereof.

2. A composition comprising a compound of claim 1, or a pharmaceutically acceptable salt thereof, and at least one pharmaceutically acceptable carrier.

3. A method of therapeutically treating a cancer that is associated with activity of a TEAD-transcription factor, the method comprising administering to a patient in need of such treatment a therapeutically effective amount of a compound of claim 1, or a pharmaceutically acceptable salt thereof.

4. The method of claim 3, wherein the cancer is a solid tumor or a hematological cancer.

5. The method of claim 3, wherein the cancer is prostate cancer, colon cancer, esophageal cancer, endometrial cancer, ovarian cancer, uterine cancer, renal cancer, hepatic cancer, pancreatic cancer, gastric cancer, breast cancer, lung cancer, cancer of the head or neck, thyroid cancer, glioblastoma, sarcoma, bladder cancer, lymphoma, leukemia, acute lymphoblastic leukemia, acute myelogenous leukemia, chronic lymphocytic leukemia, chronic myelogenous leukemia, diffuse large-B cell lymphoma, mantle cell lymphoma, non-Hodgkin lymphoma, Hodgkin lymphoma or multiple myeloma.

6. The method of claim 3, wherein the cancer is hepatocellular carcinoma, medulloblastoma, cutaneous squamous cell carcinoma, lung cancer, pancreatic cancer, esophagus cancer, liver cancer, colon cancer, melanoma, or uveal melanoma.

7. A compound having formula:

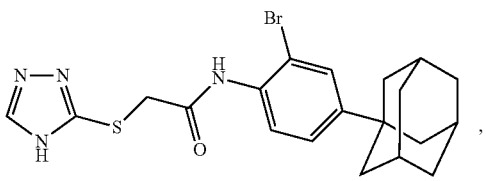 [SMILES: O=C(CSc1nnc[nH]1)Nc1ccc(C23CC4CC(CC(C4)C2)C3)cc1Br]

or a pharmaceutically acceptable salt thereof.

8. A composition comprising a compound of claim 7, or a pharmaceutically acceptable salt thereof, and at least one pharmaceutically acceptable carrier.

9. A method of therapeutically treating a cancer that is associated with activity of a TEAD-transcription factor, the method comprising administering to a patient in need of such treatment a therapeutically effective amount of a compound of claim 7, or a pharmaceutically acceptable salt thereof.

10. The method of claim 9, wherein the cancer is a solid tumor or a hematological cancer.

11. The method of claim 9, wherein the cancer is prostate cancer, colon cancer, esophageal cancer, endometrial cancer, ovarian cancer, uterine cancer, renal cancer, hepatic cancer, pancreatic cancer, gastric cancer, breast cancer, lung cancer, cancer of the head or neck, thyroid cancer, glioblastoma, sarcoma, bladder cancer, lymphoma, leukemia, acute lymphoblastic leukemia, acute myelogenous leukemia, chronic lymphocytic leukemia, chronic myelogenous leukemia, diffuse large-B cell lymphoma, mantle cell lymphoma, non-Hodgkin lymphoma, Hodgkin lymphoma or multiple myeloma.

12. The method of claim 9, wherein the cancer is hepatocellular carcinoma, medulloblastoma, cutaneous squamous cell carcinoma, lung cancer, pancreatic cancer, esophagus cancer, liver cancer, colon cancer, melanoma, or uveal melanoma.

13. A compound selected from:

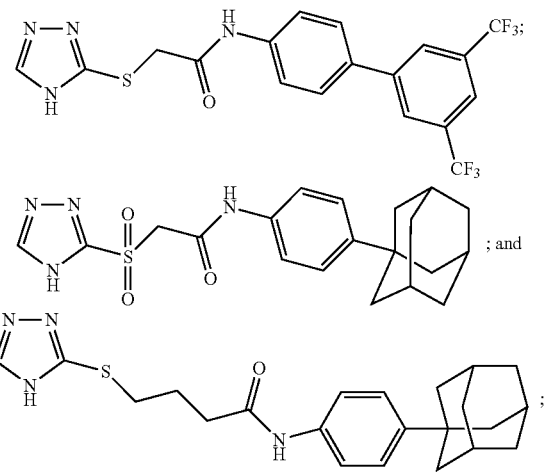

or a pharmaceutically acceptable salt thereof.

14. A composition comprising a compound of claim 13, or a pharmaceutically acceptable salt thereof, and at least one pharmaceutically acceptable carrier.

15. A method of therapeutically treating a cancer that is associated with activity of a TEAD-transcription factor, the method comprising administering to a patient in need of such treatment a therapeutically effective amount of a compound of claim 13, or a pharmaceutically acceptable salt thereof.

16. The method of claim 13, wherein the cancer is a solid tumor or a hematological cancer.

17. The method of claim 13, wherein the cancer is prostate cancer, colon cancer, esophageal cancer, endometrial cancer, ovarian cancer, uterine cancer, renal cancer, hepatic cancer, pancreatic cancer, gastric cancer, breast cancer, lung cancer, cancer of the head or neck, thyroid cancer, glioblastoma, sarcoma, bladder cancer, lymphoma, leukemia, acute lymphoblastic leukemia, acute myelogenous leukemia, chronic lymphocytic leukemia, chronic myelogenous leukemia, diffuse large-B cell lymphoma, mantle cell lymphoma, non-Hodgkin lymphoma, Hodgkin lymphoma or multiple myeloma.

18. The method of claim 13, wherein the cancer is hepatocellular carcinoma, medulloblastoma, cutaneous squamous cell carcinoma, lung cancer, pancreatic cancer, esophagus cancer, liver cancer, colon cancer, melanoma, or uveal melanoma.

* * * * *

UNITED STATES PATENT AND TRADEMARK OFFICE
CERTIFICATE OF CORRECTION

PATENT NO. : 10,696,642 B2
APPLICATION NO. : 15/762993
DATED : June 30, 2020
INVENTOR(S) : Xu Wu Page 1 of 1

It is certified that error appears in the above-identified patent and that said Letters Patent is hereby corrected as shown below:

On the Title Page

Item (56), Column 2 (Other Publications), Line 7, delete "TEA.D4" and insert -- TEAD4 --

Signed and Sealed this
Thirteenth Day of October, 2020

Andrei Iancu
*Director of the United States Patent and Trademark Office*